US012275797B2

(12) United States Patent
Oostindie et al.

(10) Patent No.: US 12,275,797 B2
(45) Date of Patent: Apr. 15, 2025

(54) ANTI-CD37 ANTIBODIES AND ANTI-CD20 ANTIBODIES, COMPOSITIONS AND METHODS OF USE THEREOF

(71) Applicant: GENMAB HOLDING B.V., Utrecht (NL)

(72) Inventors: Simone Oostindie, Utrecht (NL); Frank Beurskens, Utrecht (NL); Ronald Taylor, Keswick, VA (US); Margaret Lindorfer, Keswick, VA (US); Hilma Van Der Horst, Utrecht (NL); Martine E. D. Chamuleau, Amsterdam (NL); Tuna Mutis, Amsterdam (NL); Paul Parren, Odijk (NL); Esther Breij, Utrecht (NL)

(73) Assignee: GENMAB HOLDING B.V., Utrecht (NL)

( * ) Notice: Subject to any disclaimer, the term of this patent is extended or adjusted under 35 U.S.C. 154(b) by 1061 days.

(21) Appl. No.: 17/253,276

(22) PCT Filed: Jun. 24, 2019

(86) PCT No.: PCT/EP2019/066700
§ 371 (c)(1),
(2) Date: Dec. 17, 2020

(87) PCT Pub. No.: WO2019/243636
PCT Pub. Date: Dec. 26, 2019

(65) Prior Publication Data
US 2021/0371539 A1 Dec. 2, 2021

Related U.S. Application Data

(60) Provisional application No. 62/688,921, filed on Jun. 22, 2018.

(51) Int. Cl.
*A61K 39/395* (2006.01)
*A61K 45/06* (2006.01)
*C07K 16/28* (2006.01)

(52) U.S. Cl.
CPC .......... *C07K 16/2896* (2013.01); *A61K 45/06* (2013.01); *C07K 16/2887* (2013.01); *C07K 2317/24* (2013.01); *C07K 2317/565* (2013.01); *C07K 2317/72* (2013.01)

(58) Field of Classification Search
None
See application file for complete search history.

(56) References Cited

U.S. PATENT DOCUMENTS

| 10,759,867 | B2 | 9/2020 | Parren et al. |
|---|---|---|---|
| 11,034,772 | B2 | 6/2021 | Oostindie et al. |
| 11,180,572 | B2 | 11/2021 | De Jong et al. |
| 11,396,553 | B2 | 7/2022 | Oostindie et al. |
| 11,512,137 | B2 | 11/2022 | Oostindie et al. |
| 12,049,512 | B2 | 7/2024 | Parren et al. |
| 2014/0242075 | A1 | 8/2014 | Parren et al. |
| 2015/0175707 | A1 | 6/2015 | De Jong et al. |
| 2020/0270359 | A1 | 8/2020 | Oostindie et al. |
| 2020/0291124 | A1 | 9/2020 | Oostindie et al. |
| 2021/0024647 | A1 | 1/2021 | Oostindie et al. |
| 2021/0163619 | A1 | 6/2021 | Parren et al. |
| 2021/0230301 | A1 | 7/2021 | De Jong et al. |
| 2021/0355232 | A1 | 11/2021 | Oostindie et al. |
| 2022/0251231 | A1 | 8/2022 | Oostindie et al. |
| 2024/0076397 | A1 | 3/2024 | Oostindie et al. |
| 2024/0117064 | A1 | 4/2024 | Oostindie et al. |
| 2024/0252635 | A1 | 8/2024 | Oostindie et al. |

FOREIGN PATENT DOCUMENTS

| EP | 2241577 A1 | 10/2010 |
|---|---|---|
| WO | 2009/126944 A1 | 10/2009 |
| WO | 2011/112978 A1 | 9/2011 |
| WO | 2012/007576 A1 | 1/2012 |
| WO | 2012/135740 A2 | 10/2012 |
| WO | 2014/006217 A1 | 1/2014 |
| WO | WO/2014/006217 | * 1/2014 |

(Continued)

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
U.S. Appl. No. 16/921,154, filed Jul. 6, 2020, Paul Parren, U.S. Pat. No. 12,049,512.
U.S. Appl. No. 14/130,543, filed May 5, 2014, Paul Parren, U.S. Pat. No. 10,759,867.
U.S. Appl. No. 18/741,587, filed Jun. 12, 2024, Paul Parren.
U.S. Appl. No. 17/012,102, filed Sep. 4, 2020, Rob N. De Jong, US 20210230301.
U.S. Appl. No. 14/413,178, filed Mar. 17, 2015, Rob N. De Jong, U.S. Pat. No. 11,180,572.
U.S. Appl. No. 17/066,190, filed Oct. 8, 2020, Simone Oostindie, U.S. Pat. No. 11,034,772.

(Continued)

*Primary Examiner* — Meera Natarajan
(74) *Attorney, Agent, or Firm* — Nelson Mullins Riley & Scarborough LLP; Jane E. Remillard, Esq.; Christopher L. Frank

(57) ABSTRACT

The present invention relates to anti-CD37antibodies having an Fc-Fc interaction enhancing substitution in the Fc-region of a human IgG, for use as a medicament in combination with anti-CD20 antibodies having an Fc-Fc interaction enhancing substitution in the Fc-region of a human IgG. The invention also relates to a novel composition of anti-CD37 antibodies having an Fc-Fc 5 interaction enhancing substitution and anti-CD20 antibodies having an Fc-Fc interaction enhancing substitution. In particular, the invention relates to compositions wherein the anti-CD37 antibody binds human CD37 and the anti-CD20 antibody binds human CD20. The invention also relates to compositions where the composition is a pharmaceutical composition and the use of such compositions in treatment of cancer and other diseases.

18 Claims, 19 Drawing Sheets

Specification includes a Sequence Listing.

(56) References Cited

FOREIGN PATENT DOCUMENTS

| WO | 2015/116729 A2 | | 8/2015 |
|---|---|---|---|
| WO | WO/2015/116729 | * | 8/2015 |
| WO | 2018/178396 A1 | | 10/2018 |
| WO | WO/2018/178396 | * | 10/2018 |

OTHER PUBLICATIONS

U.S. Appl. No. 16/872,140, filed May 11, 2020, Simone Oostindie, U.S. Pat. No. 11,512,137.
U.S. Appl. No. 16/498,104, filed Apr. 3, 2018, Simone Oostindie, US 20200270359.
U.S. Appl. No. 17/975,333, filed Oct. 27, 2022, Simone Oostindie, US-20230399414.
U.S. Appl. No. 17/975,362, filed Oct. 27, 2022, Simone Oostindie, US 20240117064.
U.S. Appl. No. 17/975,353, filed Oct. 27, 2023, Simone Oostindie, US 20240076397.
U.S. Appl. No. 17/382,758, filed Jul. 22, 2021, Simone Oostindie, U.S. Pat. No. 11,396,553.
U.S. Appl. No. 17/534,029, filed Jul. 22, 2021, Simone Oostindie, US 20220251231.
U.S. Appl. No. 17/281,724, filed Mar. 31, 2021, Simone Oostindie, US 20240252635.
Anderson, K. et al., "Expression of human B cell-associated antigens on leukemias and lymphomas: a model of human B cell differentiation," Blood, vol. 63(6):1424-1433 (1984).
Dahle, J. et al., "Evaluating antigen targeting and anti-tumor activity of a new anti-CD37 radioimmunoconjugate against non-Hodgkin's lymphoma," Anticancer Res., vol. 33(1): 85-96 (2013).
De Jong, R. et al. "A Novel Platform for the Potentiation of the Therapeutic Antibodies Based on Antigen-Dependent Formation of IgG Hexamers at the Cell Surface" Plos Biology, vol. 14 (1): e1002344: 24 pages (2016).
Deckert, J. et al., "A novel anti-CD37 antibody-drug conjugate with multiple anti-tumor mechanisms for the treatment of B-cell malignancies," Blood, vol. 122(20):3500-10 (2013).
Einfield, D.A. et al., "Molecular cloning of the human B cell CD20 receptor predicts a hydrophobic protein with multiple transmembrane domains," EMBO J., vol. 7(3):711-717 (1988).
Heider, K. et al., "A novel Fc-engineered monoclonal antibody to CD37 with enhanced ADCC and high proapoptotic activity for treatment of B-cell malignancies," Blood, vol. 118 (15): 4159-4168 (2011).
Hicks, S. et al. "The Antitumor Activity of IMGN529, a CD37-Targeting Antibody-Drug Conjugate, Is Potentiated by Rituximab in Non-Hodgkin Lymphoma Models" Neoplasia, vol. 19(9): 661-671 (2017).
Link et al., J Pathol.; vol. 152:12-21 (1987).
Maecker, T. et al., "The tetraspanin superfamily: molecular facilitators," FASEB J., vol. 11(6):428-442 (1997).
Moore et al. J Immunol., vol. 137(9):3013-8 (1986).
Oostindie, S. et al. "CD20 and CD37 antibodies synergize to activate complement by Fc-mediated clustering," The Hematology Journal. vol. 104(9): 1841-1852 (2019).
Pereira, D. et al., "AGS67E, an Anti-CD37 Monomethyl Auristatin E Antibody-Drug Conjugate as a Potential Therapeutic for B/T-Cell Malignancies and AML: A New Role for CD37 in AML," Mol Cancer Ther., vol. 14(7): 1650-1660 (2015).
Robak and Robak, "Anti-CD37 antibodies for chronic lymphocytic leukemia," Expert Opin Biol Ther., vol. 14(5):651-61 (2014).
Schwartz-Albiez, R. et al., "The B cell-associated CD37 antigen (gp40-52). Structure and subcellular expression of an extensively glycosylated glycoproteinm," J. Immunol., vol. 140(3):905-914 (1988).
Tedder, T. et al., "The B cell surface molecule B1 is functionally linked with B cell activation and differentiation," J. Immunol., vol. 135(2):973-979 (1985).
Valentine, M. et al., "Phosphorylation of the CD20 phosphoprotein in resting B lymphocytes. Regulation by protein kinase C," J. Biol. Chem., vol. 264(19):11282-11287 (1989).
Zhao, X. et al., "Targeting CD37-positive lymphoid malignancies with a novel engineered small modular immunopharmaceutical," Blood, vol. 110 (7): 2569-2577 (2007).

* cited by examiner

FIG. 2A

CDC Daudi
Hx-CD37-37.3 + Hx-CD20-7D8
Lysis (%)

| Concentration Hx-CD20-7D8 (µg/mL) | | | | | | | | |
|---|---|---|---|---|---|---|---|---|
| 0.8 | 96.7 | 97.5 | 98.5 | 97.6 | 98.6 | 98.6 | 99.2 | 99.4 |
| 0.4 | 88.1 | 86 | 89.4 | 90.7 | 96.4 | 97.9 | 98.8 | 99.2 |
| 0.2 | 49.7 | 55.1 | 77.6 | 60.9 | 79.9 | 87.5 | 98.1 | 98.3 |
| 0.1 | 27.9 | 33 | 36.6 | 45 | 58.7 | 71.9 | 92.2 | 97.3 |
| 0.05 | 19.3 | 25.3 | 28.2 | 34.7 | 44.8 | 75.9 | 90 | 95 |
| 0.025 | 15.9 | 19.6 | 24.3 | 29.5 | 37.7 | 54.2 | 79.3 | 94.5 |
| 0.0125 | 16.4 | 16.6 | 23.9 | 28.2 | 35 | 68.1 | 76.7 | 93.3 |
| 0 | 14.9 | 16.5 | 20.8 | 25.9 | 38.1 | 50.2 | 82.8 | 92.5 |
| | 0 | 0.0125 | 0.025 | 0.05 | 0.1 | 0.2 | 0.4 | 0.8 |

Concentration Hx-CD37-37.3 (µg/mL)

FIG. 2B

CDC Daudi
Hx-CD37-37.3 + Hx-CD20-11B8
Lysis (%)

| Concentration Hx-CD20-11B8 (µg/mL) | | | | | | | | |
|---|---|---|---|---|---|---|---|---|
| 8 | 91.4 | 94.8 | 96.3 | 97.2 | 97.2 | 98.1 | 98.3 | 97.9 |
| 4 | 75.5 | 89.2 | 89.6 | 93.8 | 94.6 | 96.7 | 98.1 | 98.3 |
| 2 | 51.1 | 69.2 | 72.6 | 88.9 | 93.7 | 94.4 | 98.1 | 98.2 |
| 1 | 31.1 | 56.5 | 51.2 | 70.7 | 75 | 90 | 96.7 | 98 |
| 0.5 | 25.1 | 33.9 | 41.7 | 53.4 | 59.3 | 85.6 | 96.6 | 96.1 |
| 0.25 | 24.5 | 31.6 | 36.7 | 39.1 | 50.7 | 74.2 | 91.7 | 95.7 |
| 0.125 | 17.6 | 26.3 | 29 | 34.7 | 44.5 | 66.6 | 89.6 | 95.3 |
| 0 | 15.3 | 19.5 | 23.4 | 33.7 | 39.1 | 67.7 | 89.5 | 93 |
| | 0 | 0.0125 | 0.025 | 0.05 | 0.1 | 0.2 | 0.4 | 0.8 |

Concentration Hx-CD37-37.3 (µg/mL)

FIG. 2C

**CDC Daudi
Hx-CD37-37.3 + Hx-CD20-7D8
CI values**

| Concentration Hx-CD20-7D8 (µg/mL) | | | | | | | |
|---|---|---|---|---|---|---|---|
| 0.8 | 0.39 | 0.26 | 0.39 | 0.25 | 0.27 | 0.18 | 0.16 |
| 0.4 | 0.90 | 0.70 | 0.65 | 0.30 | 0.21 | 0.15 | 0.13 |
| 0.2 | 1.73 | 0.77 | 1.65 | 0.86 | 0.66 | 0.15 | 0.20 |
| 0.1 | 1.96 | 1.92 | 1.71 | 1.39 | 1.18 | 0.44 | 0.26 |
| 0.05 | 1.52 | 1.64 | 1.70 | 1.74 | 0.78 | 0.49 | 0.43 |
| 0.025 | 1.25 | 1.35 | 1.63 | 2.28 | 1.80 | 1.06 | 0.45 |
| 0.0125 | 1.05 | 1.07 | 1.47 | 1.96 | 0.94 | 1.18 | 0.55 |
| | 0.0125 | 0.025 | 0.05 | 0.1 | 0.2 | 0.4 | 0.8 |

Concentration Hx-CD37-37.3 (µg/mL)

FIG. 2D

**CDC Daudi
Hx-CD37-37.3 + Hx-CD20-11B8
CI values**

| Concentration Hx-CD20-11B8 (µg/mL) | | | | | | | |
|---|---|---|---|---|---|---|---|
| 8 | 0.27 | 0.19 | 0.20 | 0.17 | 0.14 | 0.17 | 0.34 |
| 4 | 0.34 | 0.35 | 0.21 | 0.22 | 0.18 | 0.15 | 0.24 |
| 2 | 0.76 | 0.70 | 0.25 | 0.18 | 0.24 | 0.13 | 0.23 |
| 1 | 0.76 | 1.11 | 0.59 | 0.69 | 0.38 | 0.21 | 0.25 |
| 0.5 | 1.20 | 1.06 | 0.92 | 1.16 | 0.51 | 0.21 | 0.47 |
| 0.25 | 0.84 | 0.93 | 1.32 | 1.44 | 0.98 | 0.51 | 0.51 |
| 0.125 | 0.77 | 1.04 | 1.39 | 1.71 | 1.36 | 0.65 | 0.56 |
| | 0.0125 | 0.025 | 0.05 | 0.1 | 0.2 | 0.4 | 0.8 |

Concentration Hx-CD37-37.3 (µg/mL)

1. IgG1mm-HB43-A555 + IgG1-CD20-7D8-A647
2. IgG1-CD20-7D8-A555 + IgG1mm-HB43-A647
3. IgG1mm-HB57-A555 + IgG1-CD20-7D8-A647
4. IgG1-CD20-7D8-A555 + IgG1mm-HB57-A647

SEQUENCE LISTING

<160> NUMBER OF SEQ ID NOS: 108

<210> SEQ ID NO 1
<211> LENGTH: 281
<212> TYPE: PRT
<213> ORGANISM: Human

<400> SEQUENCE: 1

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 2
<211> LENGTH: 281
<212> TYPE: PRT
<213> ORGANISM: Cynomolgus monkey

<400> SEQUENCE: 2

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly

```
            35                  40                  45
Leu Ala Phe Val Pro Leu Gln Ile Trp Ser Lys Val Leu Ala Ile Ser
         50                  55                  60
Gly Val Phe Thr Met Gly Leu Ala Leu Leu Gly Cys Val Gly Ala Leu
 65                  70                  75                  80
Lys Glu Leu Arg Cys Leu Leu Gly Leu Tyr Phe Gly Met Leu Leu Leu
                 85                  90                  95
Leu Phe Ala Thr Gln Ile Thr Leu Gly Ile Leu Ile Ser Thr Gln Arg
            100                 105                 110
Ala Gln Leu Glu Arg Ser Leu Gln Asp Ile Val Glu Lys Thr Ile Gln
        115                 120                 125
Lys Tyr His Thr Asn Pro Glu Glu Thr Ala Ala Glu Glu Ser Trp Asp
    130                 135                 140
Tyr Val Gln Phe Gln Leu Arg Cys Cys Gly Trp His Ser Pro Gln Asp
145                 150                 155                 160
Trp Phe Gln Val Leu Thr Leu Arg Gly Asn Gly Ser Glu Ala His Arg
                165                 170                 175
Val Pro Cys Ser Cys Tyr Asn Leu Ser Ala Thr Asn Asp Ser Thr Ile
            180                 185                 190
Leu Asp Lys Val Ile Leu Pro Gln Leu Ser Arg Leu Gly Gln Leu Ala
        195                 200                 205
Arg Ser Arg His Ser Thr Asp Ile Cys Ala Val Pro Ala Asn Ser His
    210                 215                 220
Ile Tyr Arg Glu Gly Cys Ala Arg Ser Leu Gln Lys Trp Leu His Asn
225                 230                 235                 240
Asn Leu Ile Ser Ile Val Gly Ile Cys Leu Gly Val Gly Leu Leu Glu
                245                 250                 255
Leu Gly Phe Met Thr Leu Ser Ile Phe Leu Cys Arg Asn Leu Asp His
            260                 265                 270
Val Tyr Asn Arg Leu Ala Arg Tyr Arg
        275                 280

<210> SEQ ID NO 3
<211> LENGTH: 390
<212> TYPE: PRT
<213> ORGANISM: Artificial Sequence
<220> FEATURE:
<223> OTHER INFORMATION: Synthetic: CD37

<400> SEQUENCE: 3

Met Trp Trp Arg Leu Trp Leu Leu Leu Leu Leu Leu Leu Leu Leu Trp
 1               5                  10                  15
Pro Met Val Trp Ala Arg Ala Gln Leu Glu Arg Ser Leu Arg Asp Val
                20                  25                  30
Val Glu Lys Thr Ile Gln Lys Tyr Gly Thr Asn Pro Glu Glu Thr Ala
            35                  40                  45
Ala Glu Glu Ser Trp Asp Tyr Val Gln Phe Gln Leu Arg Cys Cys Gly
         50                  55                  60
Trp His Tyr Pro Gln Asp Trp Phe Gln Val Leu Ile Leu Arg Gly Asn
 65                  70                  75                  80
Gly Ser Glu Ala His Arg Val Pro Cys Ser Cys Tyr Asn Leu Ser Ala
                 85                  90                  95
Thr Asn Asp Ser Thr Ile Leu Asp Lys Val Ile Leu Pro Gln Leu Ser
            100                 105                 110
Arg Leu Gly His Leu Ala Arg Ser Arg His Ser Ala Asp Ile Cys Ala
```

```
            115                 120                 125
Val Pro Ala Glu Ser His Ile Tyr Arg Glu Gly Cys Ala Gln Gly Leu
130                 135                 140

Gln Lys Trp Leu His Asn Asn Pro Lys Ser Cys Asp Lys Thr His Thr
145                 150                 155                 160

Cys Pro Pro Cys Pro Ala Pro Glu Ala Glu Gly Ala Pro Ser Val Phe
                165                 170                 175

Leu Phe Pro Pro Lys Pro Lys Asp Thr Leu Met Ile Ser Arg Thr Pro
                180                 185                 190

Glu Val Thr Cys Val Val Val Asp Val Ser His Glu Asp Pro Glu Val
                195                 200                 205

Lys Phe Asn Trp Tyr Val Asp Gly Val Glu Val His Asn Ala Lys Thr
            210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Tyr Thr Leu Pro Pro
                275                 280                 285

Ser Arg Glu Glu Met Thr Lys Asn Gln Val Ser Leu Thr Cys Leu Val
            290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Ala Pro Pro Val Leu Asp Ser Asp
                325                 330                 335

Gly Ser Phe Phe Leu Tyr Ser Lys Leu Thr Val Asp Lys Ser Arg Trp
                340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly Lys His His
            370                 375                 380

His His His His His His
385                 390

<210> SEQ ID NO 4
<211> LENGTH: 390
<212> TYPE: PRT
<213> ORGANISM: Artificial Sequence
<220> FEATURE:
<223> OTHER INFORMATION: Synthetic: CD37

<400> SEQUENCE: 4

Met Trp Trp Arg Leu Trp Trp Leu Leu Leu Leu Leu Leu Leu Leu Trp
1               5                   10                  15

Pro Met Val Trp Ala Arg Ala Gln Leu Glu Arg Ser Leu Gln Asp Ile
                20                  25                  30

Val Glu Lys Thr Ile Gln Lys Tyr His Thr Asn Pro Glu Glu Thr Ala
            35                  40                  45

Ala Glu Glu Ser Trp Asp Tyr Val Gln Phe Gln Leu Arg Cys Cys Gly
        50                  55                  60

Trp His Ser Pro Gln Asp Trp Phe Gln Val Leu Thr Leu Arg Gly Asn
65                  70                  75                  80

Gly Ser Glu Ala His Arg Val Pro Cys Ser Cys Tyr Asn Leu Ser Ala
```

```
                     85                  90                  95

Thr Asn Asp Ser Thr Ile Leu Asp Lys Val Ile Leu Pro Gln Leu Ser
                100                 105                 110

Arg Leu Gly Gln Leu Ala Arg Ser Arg His Ser Thr Asp Ile Cys Ala
                115                 120                 125

Val Pro Ala Asn Ser His Ile Tyr Arg Glu Gly Cys Ala Arg Ser Leu
                130                 135                 140

Gln Lys Trp Leu His Asn Asn Pro Lys Ser Cys Asp Lys Thr His Thr
145                 150                 155                 160

Cys Pro Pro Cys Pro Ala Pro Glu Ala Glu Gly Ala Pro Ser Val Phe
                165                 170                 175

Leu Phe Pro Pro Lys Pro Lys Asp Thr Leu Met Ile Ser Arg Thr Pro
                180                 185                 190

Glu Val Thr Cys Val Val Val Asp Val Ser His Glu Asp Pro Glu Val
                195                 200                 205

Lys Phe Asn Trp Tyr Val Asp Gly Val Glu Val His Asn Ala Lys Thr
                210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Tyr Thr Leu Pro Pro
                275                 280                 285

Ser Arg Glu Glu Met Thr Lys Asn Gln Val Ser Leu Thr Cys Leu Val
                290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Ala Pro Pro Val Leu Asp Ser Asp
                325                 330                 335

Gly Ser Phe Phe Leu Tyr Ser Lys Leu Thr Val Asp Lys Ser Arg Trp
                340                 345                 350

Gln Gln Gly Asn Val Phe Ser Cys Ser Val Met His Glu Ala Leu His
                355                 360                 365

Asn His Tyr Thr Gln Lys Ser Leu Ser Leu Ser Pro Gly Lys His His
                370                 375                 380

His His His His His His
385                 390

<210> SEQ ID NO 5
<211> LENGTH: 297
<212> TYPE: PRT
<213> ORGANISM: Human

<400> SEQUENCE: 5

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
                20                  25                  30

Arg Met Ser Ser Leu Val Gly Pro Thr Gln Ser Phe Phe Met Arg Glu
                35                  40                  45

Ser Lys Thr Leu Gly Ala Val Gln Ile Met Asn Gly Leu Phe His Ile
                50                  55                  60
```

```
Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Gly Ile Met Tyr Ile Ile
                 85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Ser Ser Gln Pro
                245                 250                 255

Lys Asn Glu Glu Asp Ile Glu Ile Ile Pro Ile Gln Glu Glu Glu Glu
                260                 265                 270

Glu Glu Thr Glu Thr Asn Phe Pro Glu Pro Pro Gln Asp Gln Glu Ser
            275                 280                 285

Ser Pro Ile Glu Asn Asp Ser Ser Pro
            290                 295

<210> SEQ ID NO 6
<211> LENGTH: 297
<212> TYPE: PRT
<213> ORGANISM: Cynomolgus monkey

<400> SEQUENCE: 6

Met Thr Thr Pro Arg Asn Ser Val Asn Gly Thr Phe Pro Ala Glu Pro
  1               5                  10                  15

Met Lys Gly Pro Ile Ala Met Gln Pro Gly Pro Lys Pro Leu Leu Arg
             20                  25                  30

Arg Met Ser Ser Leu Val Gly Pro Thr Gln Ser Phe Phe Met Arg Glu
         35                  40                  45

Ser Lys Ala Leu Gly Ala Val Gln Ile Met Asn Gly Leu Phe His Ile
     50                  55                  60

Ala Leu Gly Gly Leu Leu Met Ile Pro Ala Gly Ile Tyr Ala Pro Ile
 65                  70                  75                  80

Cys Val Thr Val Trp Tyr Pro Leu Trp Gly Gly Ile Met Tyr Ile Ile
                 85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
130                 135                 140
```

```
His Phe Leu Lys Met Glu Ser Leu Asn Phe Ile Arg Val His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
            195                 200                 205

Ala Gly Ile Val Glu Asn Glu Trp Arg Arg Thr Cys Ser Arg Pro Lys
        210                 215                 220

Ser Ser Val Val Leu Leu Ser Ala Glu Glu Lys Lys Glu Gln Val Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 7
<211> LENGTH: 115
<212> TYPE: PRT
<213> ORGANISM: Artificial Sequence
<220> FEATURE:
<223> OTHER INFORMATION: VH region

<400> SEQUENCE: 7

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 8
<211> LENGTH: 8
<212> TYPE: PRT
<213> ORGANISM: Artificial Sequence
<220> FEATURE:
<223> OTHER INFORMATION: VH region CDR1

<400> SEQUENCE: 8

Gly Phe Ser Leu Thr Thr Ser Gly
1               5
```

```
<210> SEQ ID NO 9
<211> LENGTH: 7
<212> TYPE: PRT
<213> ORGANISM: Artificial Sequence
<220> FEATURE:
<223> OTHER INFORMATION: VH region CDR2

<400> SEQUENCE: 9

Ile Trp Gly Asp Gly Ser Thr
1               5

<210> SEQ ID NO 10
<211> LENGTH: 9
<212> TYPE: PRT
<213> ORGANISM: Artificial Sequence
<220> FEATURE:
<223> OTHER INFORMATION: VH region CDR3

<400> SEQUENCE: 10

Ala Lys Gly Gly Tyr Ser Leu Ala His
1               5

<210> SEQ ID NO 11
<211> LENGTH: 107
<212> TYPE: PRT
<213> ORGANISM: Artificial Sequence
<220> FEATURE:
<223> OTHER INFORMATION: VL region

<400> SEQUENCE: 11

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys
            100                 105

<210> SEQ ID NO 12
<211> LENGTH: 6
<212> TYPE: PRT
<213> ORGANISM: Artificial Sequence
<220> FEATURE:
<223> OTHER INFORMATION: VL region CDR1

<400> SEQUENCE: 12

Glu Asn Ile Arg Ser Asn
1               5

<210> SEQ ID NO 13
<211> LENGTH: 9
<212> TYPE: PRT
<213> ORGANISM: Artificial Sequence
<220> FEATURE:
<223> OTHER INFORMATION: VL region CDR3

<400> SEQUENCE: 13
```

Gln His Tyr Trp Gly Thr Thr Trp Thr
1               5

<210> SEQ ID NO 14
<211> LENGTH: 116
<212> TYPE: PRT
<213> ORGANISM: Artificial Sequence
<220> FEATURE:
<223> OTHER INFORMATION: VH region

<400> SEQUENCE: 14

Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Val Gly Pro Met Asp Tyr Trp Gly Gln Gly Thr Ser Val
            100                 105                 110

Thr Val Ser Ser
        115

<210> SEQ ID NO 15
<211> LENGTH: 8
<212> TYPE: PRT
<213> ORGANISM: Artificial Sequence
<220> FEATURE:
<223> OTHER INFORMATION: VH region CDR1

<400> SEQUENCE: 15

Gly Tyr Ser Phe Thr Gly Tyr Asn
1               5

<210> SEQ ID NO 16
<211> LENGTH: 8
<212> TYPE: PRT
<213> ORGANISM: Artificial Sequence
<220> FEATURE:
<223> OTHER INFORMATION: VH region CDR2

<400> SEQUENCE: 16

Ile Asp Pro Tyr Tyr Gly Gly Thr
1               5

<210> SEQ ID NO 17
<211> LENGTH: 9
<212> TYPE: PRT
<213> ORGANISM: Artificial Sequence
<220> FEATURE:
<223> OTHER INFORMATION: VH region CDR3

<400> SEQUENCE: 17

Ala Arg Ser Val Gly Pro Met Asp Tyr
1               5

<210> SEQ ID NO 18
<211> LENGTH: 107

```
<212> TYPE: PRT
<213> ORGANISM: Artificial Sequence
<220> FEATURE:
<223> OTHER INFORMATION: VL region

<400> SEQUENCE: 18

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys
            100                 105

<210> SEQ ID NO 19
<211> LENGTH: 6
<212> TYPE: PRT
<213> ORGANISM: Artificial Sequence
<220> FEATURE:
<223> OTHER INFORMATION: VL region CDR1

<400> SEQUENCE: 19

Glu Asn Val Tyr Ser Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: VL region CDR3

<400> SEQUENCE: 20

Gln His His Ser Asp Asn Pro Trp Thr
1               5

<210> SEQ ID NO 21
<211> LENGTH: 118
<212> TYPE: PRT
<213> ORGANISM: Artificial Sequence
<220> FEATURE:
<223> OTHER INFORMATION: VH region

<400> SEQUENCE: 21

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Asp
            20                  25                  30

Met Ser Trp Val Arg Gln Ala Pro Gly Lys Gly Leu Glu Trp Ile Gly
        35                  40                  45

Ile Ile Tyr Ser Ser Val Gly Ala Tyr Tyr Ala Ser Trp Ala Lys Gly
    50                  55                  60

Arg Phe Thr Phe Ser Lys Thr Ser Thr Thr Val Asp Leu Lys Ile Thr
65                  70                  75                  80
```

```
Ser Pro Thr Thr Glu Asp Thr Ala Thr Tyr Phe Cys Ala Arg Glu Tyr
            85                  90                  95

Gly Ala Ser Ser Ser Asp Tyr Ile Phe Ser Leu Trp Gly Gln Gly Thr
            100                 105                 110

Leu Val Thr Val Ser Ser
            115

<210> SEQ ID NO 22
<211> LENGTH: 8
<212> TYPE: PRT
<213> ORGANISM: Artificial Sequence
<220> FEATURE:
<223> OTHER INFORMATION: VH region CDR1

<400> SEQUENCE: 22

Gly Phe Ser Leu Ser Thr Tyr Asp
1               5

<210> SEQ ID NO 23
<211> LENGTH: 7
<212> TYPE: PRT
<213> ORGANISM: Artificial Sequence
<220> FEATURE:
<223> OTHER INFORMATION: VH region CDR2

<400> SEQUENCE: 23

Ile Tyr Ser Ser Val Gly Ala
1               5

<210> SEQ ID NO 24
<211> LENGTH: 15
<212> TYPE: PRT
<213> ORGANISM: Artificial Sequence
<220> FEATURE:
<223> OTHER INFORMATION: VH region CDR3

<400> SEQUENCE: 24

Ala Arg Glu Tyr Gly Ala Ser Ser Ser Asp Tyr Ile Phe Ser Leu
1               5                   10                  15

<210> SEQ ID NO 25
<211> LENGTH: 113
<212> TYPE: PRT
<213> ORGANISM: Artificial Sequence
<220> FEATURE:
<223> OTHER INFORMATION: VL region

<400> SEQUENCE: 25

Ala Gln Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Asn Ser
            20                  25                  30

Gln Asn Leu Ala Trp Tyr Gln Gln Lys Pro Gly Gln Pro Pro Lys Leu
        35                  40                  45

Leu Ile Tyr Glu Ala Ser Lys Leu Ala Ser Gly Val Pro Ser Arg Phe
    50                  55                  60

Lys Gly Ser Gly Ser Gly Thr Gln Phe Thr Leu Thr Ile Ser Gly Val
65                  70                  75                  80

Gln Ser Asp Asp Ala Ala Thr Tyr Tyr Cys Gln Gly Glu Phe Ser Cys
                85                  90                  95

Ile Ser Ala Asp Cys Thr Ala Phe Gly Gly Gly Thr Glu Val Val Val
            100                 105                 110
```

Lys

<210> SEQ ID NO 26
<211> LENGTH: 8
<212> TYPE: PRT
<213> ORGANISM: Artificial Sequence
<220> FEATURE:
<223> OTHER INFORMATION: VL region CDR1

<400> SEQUENCE: 26

Gln Ser Val Tyr Asn Ser Gln Asn
1               5

<210> SEQ ID NO 27
<211> LENGTH: 13
<212> TYPE: PRT
<213> ORGANISM: Artificial Sequence
<220> FEATURE:
<223> OTHER INFORMATION: VL region CDR3

<400> SEQUENCE: 27

Gln Gly Glu Phe Ser Cys Ile Ser Ala Asp Cys Thr Ala
1               5                   10

<210> SEQ ID NO 28
<211> LENGTH: 116
<212> TYPE: PRT
<213> ORGANISM: Artificial Sequence
<220> FEATURE:
<223> OTHER INFORMATION: VH region

<400> SEQUENCE: 28

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Asn Trp Val Arg Gln Ala Pro Gly Lys Gly Leu Glu Trp Ile Gly
        35                  40                  45

Leu Ile Tyr Ala Ser Gly Asn Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Gly
                85                  90                  95

Ser Val Trp Gly Ala Ala Phe Asp Pro Trp Gly Pro Gly Thr Leu Val
            100                 105                 110

Thr Val Ser Ser
        115

<210> SEQ ID NO 29
<211> LENGTH: 8
<212> TYPE: PRT
<213> ORGANISM: Artificial Sequence
<220> FEATURE:
<223> OTHER INFORMATION: VH region CDR1

<400> SEQUENCE: 29

Gly Phe Ser Leu Ser Ser Asn Ala
1               5

<210> SEQ ID NO 30
<211> LENGTH: 7
<212> TYPE: PRT

```
<213> ORGANISM: Artificial Sequence
<220> FEATURE:
<223> OTHER INFORMATION: VH region CDR2

<400> SEQUENCE: 30

Ile Tyr Ala Ser Gly Asn Thr
1               5

<210> SEQ ID NO 31
<211> LENGTH: 13
<212> TYPE: PRT
<213> ORGANISM: Artificial Sequence
<220> FEATURE:
<223> OTHER INFORMATION: VH region CDR3

<400> SEQUENCE: 31

Ala Arg Glu Gly Ser Val Trp Gly Ala Ala Phe Asp Pro
1               5                   10

<210> SEQ ID NO 32
<211> LENGTH: 110
<212> TYPE: PRT
<213> ORGANISM: Artificial Sequence
<220> FEATURE:
<223> OTHER INFORMATION: VL region

<400> SEQUENCE: 32

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Asn Trp
            20                  25                  30

Leu Ala Trp Tyr Gln Gln Lys Pro Gly Gln Pro Pro Lys Gln Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Asn Ser Asn
                85                  90                  95

Ile Asp Asn Thr Phe Gly Gly Gly Thr Glu Val Val Val Lys
            100                 105                 110

<210> SEQ ID NO 33
<211> LENGTH: 6
<212> TYPE: PRT
<213> ORGANISM: Artificial Sequence
<220> FEATURE:
<223> OTHER INFORMATION: VL region CDR1

<400> SEQUENCE: 33

Gln Ser Ile Ser Asn Trp
1               5

<210> SEQ ID NO 34
<211> LENGTH: 12
<212> TYPE: PRT
<213> ORGANISM: Artificial Sequence
<220> FEATURE:
<223> OTHER INFORMATION: VL region CDR1

<400> SEQUENCE: 34

Gln Gln Gly Tyr Ser Asn Ser Asn Ile Asp Asn Thr
1               5                   10
```

```
<210> SEQ ID NO 35
<211> LENGTH: 116
<212> TYPE: PRT
<213> ORGANISM: Artificial Sequence
<220> FEATURE:
<223> OTHER INFORMATION: VH region

<400> SEQUENCE: 35

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Tyr Asn Ala
            20                  25                  30

Met Asn Trp Val Arg Gln Ala Pro Gly Lys Gly Leu Glu Trp Ile Gly
        35                  40                  45

Ile Ile Phe Ala Ser Gly Arg Thr Asp Tyr Ala Ser Trp Ala Lys Gly
    50                  55                  60

Arg Phe Thr Ile Ser Lys Thr Ser Thr Thr Val Glu Leu Lys Ile Thr
65                  70                  75                  80

Ser Pro Thr Thr Glu Asp Thr Ala Thr Tyr Phe Cys Ala Arg Glu Gly
                85                  90                  95

Ser Thr Trp Gly Asp Ala Leu Asp Pro Trp Gly Pro Gly Thr Leu Val
            100                 105                 110

Thr Val Ser Ser
        115

<210> SEQ ID NO 36
<211> LENGTH: 8
<212> TYPE: PRT
<213> ORGANISM: Artificial Sequence
<220> FEATURE:
<223> OTHER INFORMATION: VH region CDR1

<400> SEQUENCE: 36

Gly Phe Ser Leu Ser Tyr Asn Ala
1               5

<210> SEQ ID NO 37
<211> LENGTH: 7
<212> TYPE: PRT
<213> ORGANISM: Artificial Sequence
<220> FEATURE:
<223> OTHER INFORMATION: VH region CDR2

<400> SEQUENCE: 37

Ile Phe Ala Ser Gly Arg Thr
1               5

<210> SEQ ID NO 38
<211> LENGTH: 13
<212> TYPE: PRT
<213> ORGANISM: Artificial Sequence
<220> FEATURE:
<223> OTHER INFORMATION: VH region CDR3

<400> SEQUENCE: 38

Ala Arg Glu Gly Ser Thr Trp Gly Asp Ala Leu Asp Pro
1               5                   10

<210> SEQ ID NO 39
<211> LENGTH: 110
<212> TYPE: PRT
<213> ORGANISM: Artificial Sequence
<220> FEATURE:
```

<223> OTHER INFORMATION: VL region

<400> SEQUENCE: 39

Ala Tyr Asp Met Thr Gln Thr Pro Ser Ser Val Glu Ala Val Gly
1               5                   10                  15

Gly Thr Val Thr Ile Lys Cys Gln Ala Ser Gln Asn Ile Ile Asp Tyr
            20                  25                  30

Leu Ala Trp Tyr Gln Gln Lys Pro Gly Gln Pro Gln Leu Leu Ile
        35                  40                  45

His Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Gln Ser
65                  70                  75                  80

Asp Asp Ala Ala Thr Tyr Tyr Cys Gln Gln Gly Tyr Ser Asn Ser Asn
                85                  90                  95

Ile Asp Asn Thr Phe Gly Gly Gly Thr Glu Val Val Val Lys
            100                 105                 110

<210> SEQ ID NO 40
<211> LENGTH: 6
<212> TYPE: PRT
<213> ORGANISM: Artificial Sequence
<220> FEATURE:
<223> OTHER INFORMATION: VL region CDR1

<400> SEQUENCE: 40

Gln Asn Ile Ile Asp Tyr
1               5

<210> SEQ ID NO 41
<211> LENGTH: 12
<212> TYPE: PRT
<213> ORGANISM: Artificial Sequence
<220> FEATURE:
<223> OTHER INFORMATION: VL region CDR3

<400> SEQUENCE: 41

Gln Gln Gly Tyr Ser Asn Ser Asn Ile Asp Asn Thr
1               5                   10

<210> SEQ ID NO 42
<211> LENGTH: 117
<212> TYPE: PRT
<213> ORGANISM: Artificial Sequence
<220> FEATURE:
<223> OTHER INFORMATION: VH region

<400> SEQUENCE: 42

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asn
            20                  25                  30

Met Gly Trp Val Arg Gln Ala Pro Gly Lys Gly Leu Glu Trp Ile Gly
        35                  40                  45

Val Ile Asp Ala Ser Gly Thr Thr Tyr Tyr Ala Thr Trp Ala Lys Gly
    50                  55                  60

Arg Phe Thr Cys Ser Lys Thr Ser Ser Thr Val Glu Leu Lys Met Thr
65                  70                  75                  80

Ser Leu Thr Thr Glu Asp Thr Ala Thr Tyr Phe Cys Ala Arg Glu Leu
                85                  90                  95

```
Leu Tyr Phe Gly Ser Ser Tyr Tyr Asp Leu Trp Gly Gln Gly Thr Leu
            100                 105                 110

Val Thr Val Ser Ser
        115

<210> SEQ ID NO 43
<211> LENGTH: 8
<212> TYPE: PRT
<213> ORGANISM: Artificial Sequence
<220> FEATURE:
<223> OTHER INFORMATION: VH region CDR1

<400> SEQUENCE: 43

Gly Phe Ser Leu Ser Asn Tyr Asn
1               5

<210> SEQ ID NO 44
<211> LENGTH: 7
<212> TYPE: PRT
<213> ORGANISM: Artificial
<220> FEATURE:
<223> OTHER INFORMATION: VH region CDR2

<400> SEQUENCE: 44

Ile Asp Ala Ser Gly Thr Thr
1               5

<210> SEQ ID NO 45
<211> LENGTH: 14
<212> TYPE: PRT
<213> ORGANISM: Artificial Sequence
<220> FEATURE:
<223> OTHER INFORMATION: VH region CDR3

<400> SEQUENCE: 45

Ala Arg Glu Leu Leu Tyr Phe Gly Ser Ser Tyr Tyr Asp Leu
1               5                   10

<210> SEQ ID NO 46
<211> LENGTH: 110
<212> TYPE: PRT
<213> ORGANISM: Artificial Sequence
<220> FEATURE:
<223> OTHER INFORMATION: VL region

<400> SEQUENCE: 46

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Asp Ser Asn
            20                  25                  30

Leu Ala Trp Tyr Gln Gln Lys Pro Gly Gln Pro Pro Lys Phe Leu Ile
        35                  40                  45

Tyr Tyr Ala Ser Asn Leu Pro Phe Gly Val Ser Ser Arg Phe Lys Gly
    50                  55                  60

Ser Gly Ser Gly Thr Gln Phe Thr Leu Thr Ile Ser Asp Leu Glu Ser
65                  70                  75                  80

Ala Asp Ala Ala Thr Tyr Tyr Cys Gln Cys Ala Asp Val Gly Ser Thr
                85                  90                  95

Tyr Val Ala Ala Phe Gly Gly Gly Thr Glu Val Val Val Lys
            100                 105                 110

<210> SEQ ID NO 47
<211> LENGTH: 6
```

```
<212> TYPE: PRT
<213> ORGANISM: Artificial Sequence
<220> FEATURE:
<223> OTHER INFORMATION: VL region CDR1

<400> SEQUENCE: 47

Gln Asn Ile Asp Ser Asn
1               5

<210> SEQ ID NO 48
<211> LENGTH: 12
<212> TYPE: PRT
<213> ORGANISM: Artificial Sequence
<220> FEATURE:
<223> OTHER INFORMATION: VL region CDR3

<400> SEQUENCE: 48

Gln Cys Ala Asp Val Gly Ser Thr Tyr Val Ala Ala
1               5                  10

<210> SEQ ID NO 49
<211> LENGTH: 121
<212> TYPE: PRT
<213> ORGANISM: Artificial Sequence
<220> FEATURE:
<223> OTHER INFORMATION: VH region

<400> SEQUENCE: 49

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Ser Leu Ser Thr Tyr
            20                  25                  30

Asp Met Ser Trp Val Arg Gln Ala Pro Gly Lys Gly Leu Glu Trp Val
        35                  40                  45

Ser Ile Ile Tyr Ser Ser Val Gly Ala Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Tyr Gly Ala Ser Ser Ser Asp Tyr Ile Phe Ser Leu Trp Gly
            100                 105                 110

Gln Gly Thr Leu Val Thr Val Ser Ser
        115                 120

<210> SEQ ID NO 50
<211> LENGTH: 113
<212> TYPE: PRT
<213> ORGANISM: Artificial Sequence
<220> FEATURE:
<223> OTHER INFORMATION: VL region

<400> SEQUENCE: 50

Ala Gln Val Leu Thr Gln Ser Pro Ser Pro Leu Ser Ala Ser Val Gly
1               5                  10                  15

Asp Arg Val Thr Ile Thr Cys Gln Ala Ser Gln Ser Val Tyr Asn Ser
            20                  25                  30

Gln Asn Leu Ala Trp Tyr Gln Gln Lys Pro Gly Lys Ala Pro Lys Leu
        35                  40                  45

Leu Ile Tyr Glu Ala Ser Lys Leu Ala Ser Gly Val Pro Ser Arg Phe
    50                  55                  60
```

-continued

Lys Gly Ser Gly Ser Gly Thr Glu Phe Thr Leu Thr Ile Ser Ser Leu
65                  70                  75                  80

Gln Pro Asp Asp Phe Ala Thr Tyr Tyr Cys Gln Gly Glu Phe Ser Cys
                85                  90                  95

Ile Ser Ala Asp Cys Thr Ala Phe Gly Gly Gly Thr Lys Val Glu Ile
            100                 105                 110

Lys

<210> SEQ ID NO 51
<211> LENGTH: 116
<212> TYPE: PRT
<213> ORGANISM: Artificial Sequence
<220> FEATURE:
<223> OTHER INFORMATION: VH region

<400> SEQUENCE: 51

Gln Ser Val Val Glu Ser Gly Gly Gly Leu Val Gln Pro Gly Gly Ser
1               5                   10                  15

Leu Arg Leu Ser Cys Thr Val Ser Gly Phe Ser Leu Ser Asn Ala
                20                  25                  30

Met Asn Trp Val Arg Gln Ala Pro Gly Lys Gly Leu Glu Trp Ile Gly
            35                  40                  45

Leu Ile Tyr Ala Ser Gly Asn Thr Asp Tyr Ala Ser Trp Ala Lys Gly
        50                  55                  60

Arg Phe Thr Ile Ser Lys Thr Ser Thr Thr Val Tyr Leu Lys Ile Thr
65                  70                  75                  80

Ser Pro Thr Ala Glu Asp Thr Ala Thr Tyr Phe Cys Ala Arg Glu Gly
                85                  90                  95

Ser Val Trp Gly Ala Ala Phe Asp Pro Trp Gly Gln Gly Thr Leu Val
            100                 105                 110

Thr Val Ser Ser
        115

<210> SEQ ID NO 52
<211> LENGTH: 110
<212> TYPE: PRT
<213> ORGANISM: Artificial Sequence
<220> FEATURE:
<223> OTHER INFORMATION: VL region

<400> SEQUENCE: 52

Ala Tyr Asp Met Thr Gln Ser Pro Ser Ser Val Ser Ala Ser Val Gly
1               5                   10                  15

Asp Arg Val Thr Ile Thr Cys Gln Ala Ser Gln Ser Ile Ser Asn Trp
                20                  25                  30

Leu Ala Trp Tyr Gln Gln Lys Pro Gly Lys Ala Pro Lys Gln Leu Ile
            35                  40                  45

Tyr Ala Ala Ser Thr Leu Ala Ser Gly Val Pro Ser Arg Phe Lys Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Asn Ser Asn
                85                  90                  95

Ile Asp Asn Thr Phe Gly Gly Gly Thr Lys Val Glu Ile Lys
            100                 105                 110

<210> SEQ ID NO 53
<211> LENGTH: 119

```
<212> TYPE: PRT
<213> ORGANISM: Artificial Sequence
<220> FEATURE:
<223> OTHER INFORMATION: VH region

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Tyr Asn
            20                  25                  30

Ala Met Asn Trp Val Arg Gln Ala Pro Gly Lys Gly Leu Glu Trp Val
        35                  40                  45

Ser Ile Ile Phe Ala Ser Gly Arg Thr Asp Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Ser Thr Trp Gly Asp Ala Leu Asp Pro Trp Gly Gln Gly
            100                 105                 110

Thr Leu Val Thr Val Ser Ser
            115

<210> SEQ ID NO 54
<211> LENGTH: 110
<212> TYPE: PRT
<213> ORGANISM: Artificial Sequence
<220> FEATURE:
<223> OTHER INFORMATION: VL region

<400> SEQUENCE: 54

Ala Tyr Asp Met Thr Gln Ser Pro Ser Thr Leu Ser Ala Ser Val Gly
1               5                   10                  15

Asp Arg Val Thr Ile Thr Cys Gln Ala Ser Gln Asn Ile Ile Asp Tyr
            20                  25                  30

Leu Ala Trp Tyr Gln Gln Lys Pro Gly Lys Ala Pro Lys Leu Leu Ile
        35                  40                  45

His Lys Ala Ser Thr Leu Ala Ser Gly Val Pro Ser Arg Phe Lys Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Asn Ser Asn
                85                  90                  95

Ile Asp Asn Thr Phe Gly Gly Gly Thr Lys Val Glu Ile Lys
            100                 105                 110

<210> SEQ ID NO 55
<211> LENGTH: 120
<212> TYPE: PRT
<213> ORGANISM: Artificial Sequence
<220> FEATURE:
<223> OTHER INFORMATION: VH region

<400> SEQUENCE: 55

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
            20                  25                  30

Asn Met Gly Trp Val Arg Gln Ala Pro Gly Lys Gly Leu Glu Trp Val
```

```
                35                  40                  45
Ser Val Ile Asp Ala Ser Gly Thr Thr Tyr Tyr Ala Thr Trp Ala Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Thr Tyr Tyr Cys Ala
                 85                  90                  95

Arg Glu Leu Leu Tyr Phe Gly Ser Ser Tyr Tyr Asp Leu Trp Gly Gln
                100                 105                 110

Gly Thr Leu Val Thr Val Ser Ser
            115                 120

<210> SEQ ID NO 56
<211> LENGTH: 110
<212> TYPE: PRT
<213> ORGANISM: Artificial Sequence
<220> FEATURE:
<223> OTHER INFORMATION: VL region

<400> SEQUENCE: 56

Asp Val Val Met Thr Gln Ser Pro Ser Thr Leu Ser Ala Ser Val Gly
 1               5                  10                  15

Asp Arg Val Thr Ile Thr Cys Gln Ala Ser Gln Asn Ile Asp Ser Asn
                 20                  25                  30

Leu Ala Trp Tyr Gln Gln Lys Pro Gly Lys Ala Pro Lys Phe Leu Ile
             35                  40                  45

Tyr Tyr Ala Ser Asn Leu Pro Phe Gly Val Pro Ser Arg Phe Lys Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Cys Ala Asp Val Gly Ser Thr
                 85                  90                  95

Tyr Val Ala Ala Phe Gly Gly Gly Thr Lys Val Glu Ile Lys
                100                 105                 110

<210> SEQ ID NO 57
<211> LENGTH: 110
<212> TYPE: PRT
<213> ORGANISM: Artificial Sequence
<220> FEATURE:
<223> OTHER INFORMATION: VL region

<400> SEQUENCE: 57

Asp Val Val Met Thr Gln Ser Pro Ser Thr Leu Ser Ala Ser Val Gly
 1               5                  10                  15

Asp Arg Val Thr Ile Thr Cys Gln Ala Ser Gln Asn Ile Asp Ser Asn
                 20                  25                  30

Leu Ala Trp Tyr Gln Gln Lys Pro Gly Lys Ala Pro Lys Phe Leu Ile
             35                  40                  45

Tyr Tyr Ala Ser Asn Leu Pro Phe Gly Val Pro Ser Arg Phe Lys Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Ser Ala Asp Val Gly Ser Thr
                 85                  90                  95

Tyr Val Ala Ala Phe Gly Gly Gly Thr Lys Val Glu Ile Lys
                100                 105                 110
```

```
<210> SEQ ID NO 58
<211> LENGTH: 12
<212> TYPE: PRT
<213> ORGANISM: Artificial Sequence
<220> FEATURE:
<223> OTHER INFORMATION: VL region CDR3

<400> SEQUENCE: 58

Gln Ser Ala Asp Val Gly Ser Thr Tyr Val Ala Ala
1               5                   10

<210> SEQ ID NO 59
<211> LENGTH: 122
<212> TYPE: PRT
<213> ORGANISM: Artificial Sequence
<220> FEATURE:
<223> OTHER INFORMATION: VH region

<400> SEQUENCE: 59

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120

<210> SEQ ID NO 60
<211> LENGTH: 8
<212> TYPE: PRT
<213> ORGANISM: Artificial Sequence
<220> FEATURE:
<223> OTHER INFORMATION: VH region CDR1

<400> SEQUENCE: 60

Gly Phe Thr Phe His Asp Tyr Ala
1               5

<210> SEQ ID NO 61
<211> LENGTH: 8
<212> TYPE: PRT
<213> ORGANISM: Artificial Sequence
<220> FEATURE:
<223> OTHER INFORMATION: VH region CDR2

<400> SEQUENCE: 61

Ile Ser Trp Asn Ser Gly Thr Ile
1               5

<210> SEQ ID NO 62
<211> LENGTH: 15
<212> TYPE: PRT
<213> ORGANISM: Artificial Sequence
<220> FEATURE:
```

```
<223> OTHER INFORMATION: VH region CDR3

<400> SEQUENCE: 62

Ala Lys Asp Ile Gln Tyr Gly Asn Tyr Tyr Tyr Gly Met Asp Val
1               5                   10                  15

<210> SEQ ID NO 63
<211> LENGTH: 107
<212> TYPE: PRT
<213> ORGANISM: Artificial Sequence
<220> FEATURE:
<223> OTHER INFORMATION: VL region

<400> SEQUENCE: 63

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 64
<211> LENGTH: 6
<212> TYPE: PRT
<213> ORGANISM: Artificial Sequence
<220> FEATURE:
<223> OTHER INFORMATION: VL region CDR1

<400> SEQUENCE: 64

Gln Ser Val Ser Ser Tyr
1               5

<210> SEQ ID NO 65
<211> LENGTH: 9
<212> TYPE: PRT
<213> ORGANISM: Artificial Sequence
<220> FEATURE:
<223> OTHER INFORMATION: VL region CDR3

<400> SEQUENCE: 65

Gln Gln Arg Ser Asn Trp Pro Ile Thr
1               5

<210> SEQ ID NO 66
<211> LENGTH: 125
<212> TYPE: PRT
<213> ORGANISM: Artificial Sequence
<220> FEATURE:
<223> OTHER INFORMATION: VH region

<400> SEQUENCE: 66

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
                20                  25                  30
```

```
Ala Met His Trp Val Arg Gln Ala Pro Gly Lys Gly Leu Glu Trp Val
            35                  40                  45

Ser Ile Ile Gly Thr Gly Gly Val Thr Tyr Tyr Ala Asp Ser Val Lys
 50                  55                  60

Gly Arg Phe Thr Ile Ser Arg Asp Asn Val Lys Asn Ser Leu Tyr Leu
 65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
            115                 120                 125

<210> SEQ ID NO 67
<211> LENGTH: 8
<212> TYPE: PRT
<213> ORGANISM: Artificial Sequence
<220> FEATURE:
<223> OTHER INFORMATION: VH region CDR1

<400> SEQUENCE: 67

Gly Phe Thr Phe Ser Tyr His Ala
 1               5

<210> SEQ ID NO 68
<211> LENGTH: 7
<212> TYPE: PRT
<213> ORGANISM: Artificial Sequence
<220> FEATURE:
<223> OTHER INFORMATION: VH region CDR2

<400> SEQUENCE: 68

Ile Gly Thr Gly Gly Val Thr
 1               5

<210> SEQ ID NO 69
<211> LENGTH: 19
<212> TYPE: PRT
<213> ORGANISM: Artificial Sequence
<220> FEATURE:
<223> OTHER INFORMATION: VH region CDR3

<400> SEQUENCE: 69

Ala Arg Asp Tyr Tyr Gly Ala Gly Ser Phe Tyr Asp Gly Leu Tyr Gly
 1               5                  10                  15

Met Asp Val

<210> SEQ ID NO 70
<211> LENGTH: 107
<212> TYPE: PRT
<213> ORGANISM: Artificial Sequence
<220> FEATURE:
<223> OTHER INFORMATION: VL region

<400> SEQUENCE: 70

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45
```

```
Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asp Trp Pro Leu
                 85                  90                  95

Thr Phe Gly Gly Gly Thr Lys Val Glu Ile Lys
            100                 105
```

<210> SEQ ID NO 71
<211> LENGTH: 9
<212> TYPE: PRT
<213> ORGANISM: Artificial Sequence
<220> FEATURE:
<223> OTHER INFORMATION: VL region CDR3

<400> SEQUENCE: 71

```
Gln Gln Arg Ser Asp Trp Pro Leu Thr
1               5
```

<210> SEQ ID NO 72
<211> LENGTH: 122
<212> TYPE: PRT
<213> ORGANISM: Artificial Sequence
<220> FEATURE:
<223> OTHER INFORMATION: VH region

<400> SEQUENCE: 72

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
                20                  25                  30

Ala Met His Trp Val Arg Gln Ala Pro Gly Lys Gly Leu Glu Trp Val
            35                  40                  45

Ser Thr Ile Ser Trp Asn Ser Gly Ser Ile Gly Tyr Ala Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Ile Gln Tyr Gly Asn Tyr Tyr Gly Met Asp Val Trp
            100                 105                 110

Gly Gln Gly Thr Thr Val Thr Val Ser Ser
            115                 120
```

<210> SEQ ID NO 73
<211> LENGTH: 8
<212> TYPE: PRT
<213> ORGANISM: Artificial Sequence
<220> FEATURE:
<223> OTHER INFORMATION: VH region CDR1

<400> SEQUENCE: 73

```
Gly Phe Thr Phe Asn Asp Tyr Ala
1               5
```

<210> SEQ ID NO 74
<211> LENGTH: 8
<212> TYPE: PRT
<213> ORGANISM: Artificial Sequence
<220> FEATURE:
<223> OTHER INFORMATION: VH region CDR2

<400> SEQUENCE: 74

Ile Ser Trp Asn Ser Gly Ser Ile
1               5

<210> SEQ ID NO 75
<211> LENGTH: 121
<212> TYPE: PRT
<213> ORGANISM: Artificial Sequence
<220> FEATURE:
<223> OTHER INFORMATION: VH region

<400> SEQUENCE: 75

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 76
<211> LENGTH: 8
<212> TYPE: PRT
<213> ORGANISM: Artificial Sequence
<220> FEATURE:
<223> OTHER INFORMATION: VH region CDR1

<400> SEQUENCE: 76

Gly Tyr Thr Phe Thr Ser Tyr Asn
1               5

<210> SEQ ID NO 77
<211> LENGTH: 8
<212> TYPE: PRT
<213> ORGANISM: Artificial Sequence
<220> FEATURE:
<223> OTHER INFORMATION: VH region CDR2

<400> SEQUENCE: 77

Ile Tyr Pro Gly Asn Gly Asp Thr
1               5

<210> SEQ ID NO 78
<211> LENGTH: 14
<212> TYPE: PRT
<213> ORGANISM: Artificial Sequence
<220> FEATURE:
<223> OTHER INFORMATION: VH region CDR3

<400> SEQUENCE: 78

Ala Arg Ser Thr Tyr Tyr Gly Gly Asp Trp Tyr Phe Asn Val
1               5                   10

<210> SEQ ID NO 79
<211> LENGTH: 106
<212> TYPE: PRT
<213> ORGANISM: Artificial Sequence
<220> FEATURE:
<223> OTHER INFORMATION: VL region

<400> SEQUENCE: 79

```
Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Val Ser Tyr Ile
            20                  25                  30
His Trp Phe Gln Gln Lys Pro Gly Ser Ser Pro Lys Pro Trp Ile Tyr
        35                  40                  45
Ala Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                85                  90                  95
Phe Gly Gly Gly Thr Lys Leu Glu Ile Lys
            100                 105
```

<210> SEQ ID NO 80
<211> LENGTH: 5
<212> TYPE: PRT
<213> ORGANISM: Artificial Sequence
<220> FEATURE:
<223> OTHER INFORMATION: VL region CDR1

<400> SEQUENCE: 80

```
Ser Ser Val Ser Tyr
1               5
```

<210> SEQ ID NO 81
<211> LENGTH: 9
<212> TYPE: PRT
<213> ORGANISM: Artificial Sequence
<220> FEATURE:
<223> OTHER INFORMATION: VL region CDR3

<400> SEQUENCE: 81

```
Gln Gln Trp Thr Ser Asn Pro Pro Thr
1               5
```

<210> SEQ ID NO 82
<211> LENGTH: 119
<212> TYPE: PRT
<213> ORGANISM: Artificial Sequence
<220> FEATURE:
<223> OTHER INFORMATION: VH region

<400> SEQUENCE: 82

```
Gln Val Gln Leu Val Gln Ser Gly Ala Glu Val Lys Lys Pro Gly Ser
1               5                   10                  15
Ser Val Lys Val Ser Cys Lys Ala Ser Gly Tyr Ala Phe Ser Tyr Ser
            20                  25                  30
Trp Ile Asn Trp Val Arg Gln Ala Pro Gly Gln Gly Leu Glu Trp Met
        35                  40                  45
Gly Arg Ile Phe Pro Gly Asp Gly Asp Thr Asp Tyr Asn Gly Lys Phe
    50                  55                  60
```

```
Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Val Phe Asp Gly Tyr Trp Leu Val Tyr Trp Gly Gln Gly
            100                 105                 110

Thr Leu Val Thr Val Ser Ser
        115
```

<210> SEQ ID NO 83
<211> LENGTH: 8
<212> TYPE: PRT
<213> ORGANISM: Artificial Sequence
<220> FEATURE:
<223> OTHER INFORMATION: VH region CDR1

<400> SEQUENCE: 83

```
Gly Tyr Ala Phe Ser Tyr Ser Trp
1               5
```

<210> SEQ ID NO 84
<211> LENGTH: 8
<212> TYPE: PRT
<213> ORGANISM: Artificial Sequence
<220> FEATURE:
<223> OTHER INFORMATION: VH region CDR2

<400> SEQUENCE: 84

```
Ile Phe Pro Gly Asp Gly Asp Thr
1               5
```

<210> SEQ ID NO 85
<211> LENGTH: 12
<212> TYPE: PRT
<213> ORGANISM: Artificial Sequence
<220> FEATURE:
<223> OTHER INFORMATION: VH region CDR3

<400> SEQUENCE: 85

```
Ala Arg Asn Val Phe Asp Gly Tyr Trp Leu Val Tyr
1               5                   10
```

<210> SEQ ID NO 86
<211> LENGTH: 112
<212> TYPE: PRT
<213> ORGANISM: Artificial Sequence
<220> FEATURE:
<223> OTHER INFORMATION: VL region

<400> SEQUENCE: 86

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Ala Gln Asn
                85                  90                  95
```

```
Leu Glu Leu Pro Tyr Thr Phe Gly Gly Gly Thr Lys Val Glu Ile Lys
            100                 105                 110
```

<210> SEQ ID NO 87
<211> LENGTH: 11
<212> TYPE: PRT
<213> ORGANISM: Artificial Sequence
<220> FEATURE:
<223> OTHER INFORMATION: VL region CDR1

<400> SEQUENCE: 87

```
Lys Ser Leu Leu His Ser Asn Gly Ile Thr Tyr
1               5                   10
```

<210> SEQ ID NO 88
<211> LENGTH: 9
<212> TYPE: PRT
<213> ORGANISM: Artificial Sequence
<220> FEATURE:
<223> OTHER INFORMATION: VL region CDR3

<400> SEQUENCE: 88

```
Ala Gln Asn Leu Glu Leu Pro Tyr Thr
1               5
```

<210> SEQ ID NO 89
<211> LENGTH: 127
<212> TYPE: PRT
<213> ORGANISM: Artificial Sequence
<220> FEATURE:
<223> OTHER INFORMATION: VH region

<400> SEQUENCE: 89

```
Gln Val Gln Leu Val Gln Ser Gly Ala Glu Val Lys Lys Pro Gly Ala
1               5                   10                  15

Ser Val Lys Val Ser Cys Gln Ala Ser Gly Tyr Arg Phe Ser Asn Phe
                20                  25                  30

Val Ile His Trp Val Arg Gln Ala Pro Gly Gln Arg Phe Glu Trp Met
            35                  40                  45

Gly Trp Ile Asn Pro Tyr Asn Gly Asn Lys Glu Phe Ser Ala Lys Phe
    50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125
```

<210> SEQ ID NO 90
<211> LENGTH: 8
<212> TYPE: PRT
<213> ORGANISM: Artificial Sequence
<220> FEATURE:
<223> OTHER INFORMATION: VH region CDR1

<400> SEQUENCE: 90

```
Gly Tyr Arg Phe Ser Asn Phe Val
1               5
```

<210> SEQ ID NO 91
<211> LENGTH: 8

```
<212> TYPE: PRT
<213> ORGANISM: Artificial Sequence
<220> FEATURE:
<223> OTHER INFORMATION: VH region CDR2

<400> SEQUENCE: 91

Ile Asn Pro Tyr Asn Gly Asn Lys
1               5

<210> SEQ ID NO 92
<211> LENGTH: 20
<212> TYPE: PRT
<213> ORGANISM: Artificial Sequence
<220> FEATURE:
<223> OTHER INFORMATION: VH region CDR3

<400> SEQUENCE: 92

Ala Arg Val Gly Pro Tyr Ser Trp Asp Asp Ser Pro Gln Asp Asn Tyr
1               5                   10                  15

Tyr Met Asp Val
            20

<210> SEQ ID NO 93
<211> LENGTH: 108
<212> TYPE: PRT
<213> ORGANISM: Artificial Sequence
<220> FEATURE:
<223> OTHER INFORMATION: VL region

<400> SEQUENCE: 93

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
                20                  25                  30

Arg Val Ala Trp Tyr Gln His Lys Pro Gly Gln Ala Pro Arg Leu Val
            35                  40                  45

Ile His Gly Val Ser Asn Arg Ala Ser Gly Ile Ser Asp Arg Phe Ser
        50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 94
<211> LENGTH: 7
<212> TYPE: PRT
<213> ORGANISM: Artificial Sequence
<220> FEATURE:
<223> OTHER INFORMATION: VL region CDR1

<400> SEQUENCE: 94

His Ser Ile Arg Ser Arg Arg
1               5

<210> SEQ ID NO 95
<211> LENGTH: 9
<212> TYPE: PRT
<213> ORGANISM: Artificial Sequence
<220> FEATURE:
<223> OTHER INFORMATION: VL region CDR3

<400> SEQUENCE: 95
```

```
Gln Val Tyr Gly Ala Ser Ser Tyr Thr
1               5
```

<210> SEQ ID NO 96
<211> LENGTH: 330
<212> TYPE: PRT
<213> ORGANISM: Human

<400> SEQUENCE: 96

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 97
<211> LENGTH: 330
<212> TYPE: PRT

<213> ORGANISM: Human

<400> SEQUENCE: 97

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 98
<211> LENGTH: 330
<212> TYPE: PRT
<213> ORGANISM: Human

<400> SEQUENCE: 98

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                    20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 99
<211> LENGTH: 330
<212> TYPE: PRT
<213> ORGANISM: Human

<400> SEQUENCE: 99

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Pro Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Gly Leu His Asn His Tyr Thr
305                 310                 315                 320

Gln Lys Ser Leu Ser Leu Ser Pro Gly Lys
                325                 330

<210> SEQ ID NO 100
<211> LENGTH: 330
<212> TYPE: PRT
<213> ORGANISM: Artificial Sequence
<220> FEATURE:
<223> OTHER INFORMATION: Modified Fc region

<400> SEQUENCE: 100

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Arg Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 101
<211> LENGTH: 330
<212> TYPE: PRT
<213> ORGANISM: Artificial Sequence
<220> FEATURE:
<223> OTHER INFORMATION: Modified Fc region

<400> SEQUENCE: 101

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 102
<211> LENGTH: 330
<212> TYPE: PRT
<213> ORGANISM: Artificial Sequence
<220> FEATURE:
<223> OTHER INFORMATION: Modified Fc region

<400> SEQUENCE: 102

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

```
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 103
<211> LENGTH: 330
<212> TYPE: PRT
<213> ORGANISM: Artificial Sequence
<220> FEATURE:
<223> OTHER INFORMATION: Modified Fc region

<400> SEQUENCE: 103

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190
```

-continued

```
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
        210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
290                 295                 300
Val Phe Ser Cys Ser Val Met His Glu Ala Leu His Asn His Tyr Thr
305                 310                 315                 320
Gln Glu Ser Leu Ser Leu Ser Pro Gly Lys
                325                 330
```

<210> SEQ ID NO 104
<211> LENGTH: 330
<212> TYPE: PRT
<213> ORGANISM: Artificial Sequence
<220> FEATURE:
<223> OTHER INFORMATION: Modified Fc region

<400> SEQUENCE: 104

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
```

-continued

Gln Pro Arg Glu Pro Gln Val Tyr Thr Leu Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Lys Leu Ser Leu Ser Pro Gly Lys
            325                 330

<210> SEQ ID NO 105
<211> LENGTH: 326
<212> TYPE: PRT
<213> ORGANISM: Human

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

```
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 106
<211> LENGTH: 377
<212> TYPE: PRT
<213> ORGANISM: Human

<400> SEQUENCE: 106

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
```

```
                305                 310                 315                 320
Tyr Asn Thr Thr Pro Pro Met Leu Asp Ser Asp Gly Ser Phe Phe Leu
                    325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 107
<211> LENGTH: 327
<212> TYPE: PRT
<213> ORGANISM: Human

<400> SEQUENCE: 107

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 108
<211> LENGTH: 107
<212> TYPE: PRT
<213> ORGANISM: Human

<400> SEQUENCE: 108

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

ANTI-CD37 ANTIBODIES AND ANTI-CD20 ANTIBODIES, COMPOSITIONS AND METHODS OF USE THEREOF

CROSS-REFERENCE TO RELATED APPLICATIONS

This application is a 35 U.S.C. 371 national stage filing of International Application No. PCT/EP2019/066700, filed Jun. 24, 2019, which claims priority to U.S. Provisional Application No. 62/688,921, filed Jun. 22, 2018. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Aug. 17, 2021, is named GMI_170US_Sequence_Listing.txt and is 98,849 bytes in size.

FIELD OF THE INVENTION

The present invention relates to anti-CD37antibodies having an Fc-Fc interaction enhancing substitution in the Fc region of a human IgG, for use as a medicament in combination with anti-CD20 antibodies having an Fc-Fc interaction enhancing substitution in the Fc-region of a human IgG. The invention also relates to a novel composition of anti-CD37 antibodies having an Fc-Fc interaction enhancing substitution and anti-CD20 antibodies having an Fc-Fc interaction enhancing substitution. In particular, the invention relates to compositions wherein the anti-CD37 antibody binds human CD37 and the anti-CD20 antibody binds human CD20. The invention also relates to compositions where the composition is a pharmaceutical composition and the use of such compositions in treatment of cancer and other diseases.

BACKGROUND OF THE INVENTION

Leukocyte antigen CD37 ("CD37"), also known as GP52-40, tetraspanin-26, or TSPAN26, is a transmembrane protein of the tetraspanin superfamily (Maecker et al., FASEB J. 1997;11:428-442). In normal physiology, CD37 is expressed on B cells during the pre-B to peripheral mature B-cell stages but is reportedly absent on plasma cells (Link et al., J Pathol. 1987;152:12-21). The CD37 antigen is only weakly expressed on T-cells and myeloid cells such as monocytes, macrophages, dendritic cells and granulocytes (Schwartz-Albiez et al., J. Immunol 1988; 140(3):905-914). CD37 is broadly expressed on malignant cells in a variety of B-cell leukemias and lymphomas, including non-Hodgkin's lymphoma (NHL) and chronic lymphoid leukemia (CLL) (Moore et al. J Immunol. 1986; 137(9):3013).

Several antibody-based CD37-targeting agents are being evaluated as potential therapeutics for B-cell malignancies and other malignancies. These include, for example, radioimmuno-conjugates such as lutetium ($^{177}$Lu) lilotomab, antibody-drug conjugates such as IMGN529 and AGS-67E, and reformatted or Fc-engineered antibodies such as otlertuzumab and BI 836826 (Robak and Robak, Expert Opin Biol Ther 2014; 14(5):651-61). Anti-CD37 antibodies have been proposed for use as therapeutic agents in the formats described above and other formats (see, e.g., WO 2012/135740, WO 2012/007576, WO 2011/112978, WO 2009/126944, WO 2011/112978 and EP 2 241 577).

Betalutin is a mouse anti-CD37 antibody, lilotomab (formerly HH1/tetulomab), conjugated to 177-lutetium. Betalutin internalizes rapidly, inhibits B cell growth in vitro and prolongs survival in an i.v. Daudi-SCID model (Dahle et al 2013, Anticancer Res 33: 85-96).

IMGN529 is an ADC consisting of the K7153A antibody conjugated to the maytansinoid DM1 via an SMCC linker. The K7153 antibody is reported to induce apoptosis on CD37 expressing Ramos cells in the absence of cross-linking. It also induced CDC and ADCC in Burkitt's lymphoma cell lines, though the ability to induce CDC was much less compared to rituximab (Deckert et al, Blood 2013; 122(20):3500-10). These Fc-mediated effector functions of K7153A are retained in the DM-1 conjugated antibody.

Agensys is developing AGS-67E, a human anti-CD37 IgG2 mAb conjugated to monomethyl auristatin E. AGS67E induces potent cytotoxicity and apoptosis (Pereira et al, Mol Cancer Ther 2015; 14(7): 1650-1660).

Otlertuzumab (originally known as TRU-016) is a SMIP (small modular immuno pharmaceutical; SMIPS are disulfide-linked dimers of single-chain proteins comprised of one antigen binding VH/VL, a connecting hinge region, and an Fc (fragment, crystallizable) region (CH2-CH3)). Its mechanisms of action are induction of apoptosis and ADCC, but not CDC (Zhao et al 2007, Blood 110 (7), 2569-2577).

mAb37.1/BI 836826 is a chimeric antibody that is engineered for high-affinity binding to FcγRIIIa (CD16a)(Heider et al 2011, Blood 118: 4159-4168). It has pro-apoptotic activity independent of IgG Fc crosslinking, although the pro-apoptotic activity is increased by cross-linking. It shows potent ADCC of CD37+ B cell lines and primary CLL cells.

The CD20 molecule (also called human B-lymphocyte-restricted differentiation antigen or Bp35) is a hydrophobic transmembrane protein with a molecular weight of approximately 35 kD located on pre-B and mature B lymphocytes (Valentine et al. (1989) J. Biol. Chem. 264(19):11282-11287; and Einfield et al., (1988) EMBO J. 7(3):711-717). CD20 is found on the surface of greater than 90% of B cells from peripheral blood or lymphoid organs and is expressed during early pre-B cell development and remains until plasma cell differentiation. CD20 is present on both normal B cells as well as malignant B cells. In particular, CD20 is expressed on greater than 90% of B cell non-Hodgkin's lymphomas (NHL) (Anderson et al. (1984) Blood 63(6): 1424-1433), but is not found on hematopoietic stem cells, pro-B cells, normal plasma cells, or other normal tissues (Tedder et al. (1985) J. Immunol. 135(2):973-979).

Methods for treating cancer as well as autoimmune and immune diseases by targeting CD20 are known in the art. For example, the chimeric CD20 antibody rituximab has been used for or suggested for use in treating cancers such as non-Hodgkin's lymphoma (NHL), chronic lymphocytic leukemia (CLL) and small lymphocytic lymphoma (SLL). The human monoclonal CD20 antibody ofatumumab has been used for or suggested for use in treating among others various CLL indications, follicular lymphoma (FL), neuromyelitis optica (NMO), diffuse and relapsing-remitting multiple sclerosis (RRMS). The human monoclonal CD20 antibody obinutuzumab has been used for or suggested for use in treating CLL. Furthermore, the humanized CD20 antibody ocrelizumab is being developed for RRMS.

The disadvantage of the current anti-CD37-ADC plus anti-CD20 treatment is that it does not provide benefit with regard to complement-dependent cytotoxicity (CDC) as an effector mechanism, compared to the single antibodies. Accordingly, it is an object of the present invention to provide a combination of anti-CD37 antibodies having an Fc-Fc interaction enhancing amino acid substitution and anti-CD20 antibodies with or without Fc-Fc interaction enhancing amino acid substitution(s), as described here, which eliminate tumor cells by CDC. The combination of anti-CD37 antibodies having an Fc-Fc interaction enhancing amino acid substitution and anti-CD20 antibodies with or without Fc-Fc interaction enhancing amino acid substitutions, as described here, induced highly efficient CDC-mediated tumor cell kill.

SUMMARY OF THE INVENTION

The inventors of the present invention surprisingly found that an anti-CD37antibody having an Fc-Fc interaction enhancing substitution in the Fc-region of a human IgG, for use as a medicament in combination with an anti-CD20 antibody having an Fc-Fc interaction enhancing substitution in the Fc-region of a human IgG were more potent at inducing CDC on a target cell, such as a tumor cell, than either the anti-CD37 antibody having the Fc-Fc interaction enhancing substitution alone or the anti-CD20 antibody having the Fc-Fc interaction enhancing substitution alone. The inventors of the present invention further found that a composition comprising an anti-CD37 antibody having an Fc-Fc interaction enhancing substitution and an anti-CD20 antibody having an Fc-Fc interaction enhancing substitution was more potent at inducing CDC on a target cell, such as a tumor cell, than either the anti-CD37 antibody having the Fc-Fc interaction enhancing substitution alone or the anti-CD20 antibody having the Fc-Fc interaction enhancing substitution alone.

The object of the present invention is to provide an anti-CD37 antibody having an Fc-Fc interaction enhancing substitution for use as a medicament in combination with an anti-CD20 antibody having an Fc-Fc interaction enhancing substitution.

Another object of the present invention is to provide an improved composition comprising an anti-CD37 antibody having an Fc-Fc interaction enhancing substitution and an anti-CD20 antibody with an Fc-Fc interaction enhancing substitution. A further object of the present invention is to provide such an improved composition for the treatment of cancer and other diseases.

Accordingly, the invention relates to antibodies and compositions of antibodies binding to human CD37 and human CD20 which have advantageous properties in terms of their ability to induce CDC, their Fc-Fc interaction upon binding to membrane-bound targets, their cytotoxic effect on cells expressing CD37 and/or CD20 and other properties, as described herein.

Accordingly, in one aspect the present invention relates to a first antibody comprising a first antigen binding region capable of binding to human CD37 and a first Fc-region of a human IgG, for use as a medicament in combination with a second antibody comprising a second antigen binding region capable of binding to human CD20 and a second Fc region of a human IgG, wherein the first Fc region and the second Fc region each comprises a substitution of an amino acid at a position corresponding to E430, E345 or S440, in human IgG1 according to EU numbering system, with the proviso that the substitution in S440 is S440Y or S440W.

In another aspect the present invention relates to a composition comprising a first and a second antibody, wherein the first antibody comprises a first antigen-binding region capable of binding to human CD37 and a first Fc-region of a human IgG, and the second antibody comprises a second antigen-binding region capable of binding to human CD20 and a second Fc-region of a human IgG, wherein the first and the second Fc region each comprises a substitution of an amino acid at a position corresponding to E430, E345 or S440, with the proviso that the substitution in S440 is S440Y or S440W, in human IgG1 according to EU numbering system.

In one embodiment of the invention the first and second Fc region each comprises a substitution selected from the group consisting of: E430G and E345K, preferably E430G.

In one embodiment of the invention the composition comprises a first and a second Fc region each comprising a substitution selected from the group consisting of: E430G and E345K, preferably E430G.

In another aspect the invention relates to the use of the first and second antibody or the composition of the present invention for the manufacture of a medicament.

In a specific aspect the invention relates to the use of the first and second antibody or the composition for use in the treatment of cancer or an autoimmune disease or inflammatory disorders and in particular for use in the treatment of B-cell malignancies.

In a further aspect the invention relates to the use of the first and second antibody or the composition for the manufacture of a medicament for treatment of solid tumors and/or hematological tumors.

In another aspect the invention relates to a method of inducing cell death, or inhibiting growth and/or proliferation of a tumor expressing CD37 and CD20 comprising administering to an individual in need thereof a first and second antibody or a composition according to the present invention.

In yet another aspect the invention relates to a method of treating an individual having a solid tumor and/or hematological tumor, comprising administering to said individual an effective amount of a first and second antibody or a composition according to the present invention.

BRIEF DESCRIPTION OF THE DRAWINGS

FIGS. 2A-2D show the CDC-mediated killing of Daudi cells (% lysis expressed as the PI-positive cell fraction as determined by flow cytometry) for the 8×8 concentration dilution series matrix plot for the mixture of hexamerization-enhanced CD37 antibody IgG1-CD37-37.3-E430G (Hx-CD37-37.3) and (FIG. 2A) hexamerization-enhanced CD20 antibody IgG1-CD20-7D8-E430G (Hx-CD20-7D8) or (FIG. 2B) hexamerization-enhanced CD20 antibody IgG1-CD20-11B8-E430G (Hx-CD20-11B8). From the CDC combination index (CI) values for the antibody mixtures of Hx-CD37-37.3 with (FIG. 2C) Hx-CD20-7D8 or (FIG. 2D) Hx-CD20-11B8, antibody mixture samples were classified as additive (CI=1), synergistic (CI<1) or antagonistic (CI>1).

(FIGS. 3A and 3B) Dose-response curves of purified C1q binding to Daudi cells opsonized with (FIG. 3A) 10 µg/mL IgG1-CD37-37.3-E430G (Hx-CD37-37.3), 10 µg/mL IgG1-CD20-7D8-E430G (Hx-CD20-7D8), and the mixture thereof (5+5 µg/mL) and (FIG. 3B) 10 µg/mL Hx-CD37-37.3, 10 µg/mL IgG1-CD20-11B8-E430G (Hx-CD20-11B8) and the mixture thereof (5+5 µg/mL) as determined by flow cytometry. Mean fluorescence intensity (MFI) for a C1q dilution series is shown. (FIGS. 3C and 3D) CDC dose-response curves of (FIG. 3C) 10 µg/mL Hx-CD37-37.3, 10 µg/mL Hx-CD20-7D8, and the mixture thereof (5+5 µg/mL) and (FIG. 3D) 10 µg/mL Hx-CD37-37.3, 10 µg/mL Hx-CD20-11B8 and the mixture thereof (5+5 µg/mL) in response to a serial dilution series of purified C1q that was supplemented to C1q-depleted medium. The percentage lysis is expressed as the PI-positive cell fraction as determined by flow cytometry.

(FIG. 4A) The dynamic range of FRET detection was determined using mixtures of A555- or A647-conjugated anti-CD20 antibody IgG1-CD20-7D8 with A555- or A647-conjugated mouse-anti-human IgG1 antibody IgG1 mm-HB43 (positive control) or mouse-anti-human IgM antibody IgG1 mm-HB57 (negative control). (FIGS. 4B and 4C) FRET detection for mixtures of A555- or A647-conjugated IgG1-CD37-37.3 and A555- or A647-conjugated type II CD20 antibody IgG1-CD20-11B8 (FIG. 4B) or type I CD20 antibody IgG1-CD20-7D8 (FIG. 4C). (FIGS. 4D and 4E) FRET detection for mixtures of A555- or A647-conjugated hexamerization-enhanced IgG1-CD37-37.3-E430G (Hx-CD37-37.3) and A555- or A647-conjugated hexamerization-enhanced IgG1-CD20-118-E430G (Hx-CD20-11B8) (FIG. 4D) or hexamerization-enhanced IgG1-CD20-7D8-E430G (Hx-CD20-7D8) (FIG. 4E). FRET was calculated from the mean fluorescence intensity (MFI) as determined by flow cytometry. Data shown are mean and standard deviation (SD) of six replicates collected from three experiments.

(FIG. 7A) B cell NHL (B-NHL), (FIG. 7B) Follicular Lymphoma (FL), (FIG. 7C) Mantle Cell Lymphoma (MCL) and (FIG. 7D) Marginal Zone Lymphoma (MZL). CDC induction is presented as the percentage lysis determined by the fraction of 7-AAD-positive B-lymphoma cells as determined by flow cytometry. Data shown are mean and standard deviation (SD) of two replicates from one representative experiment.

(FIG. 8A) mixtures with IgG1-CD37-37.3-E430G (Hx-CD37-37.3), (FIG. 8B) mixtures with IgG1-CD37-G28.1-E430G (Hx-CD37-G28.1), (FIG. 8C) mixtures with IgG1-CD37-004-E430G (Hx-CD37-004), (FIG. 8D) mixtures with IgG1-CD37-005-E430G (Hx-CD37-005), (FIG. 8E) mixtures with IgG1-CD37-010-E430G (Hx-CD37-010) and (FIG. 8F) mixtures with IgG1-CD37-016-E430G (Hx-CD37-016).

DETAILED DESCRIPTION OF THE INVENTION

Definitions

Figure 1A:
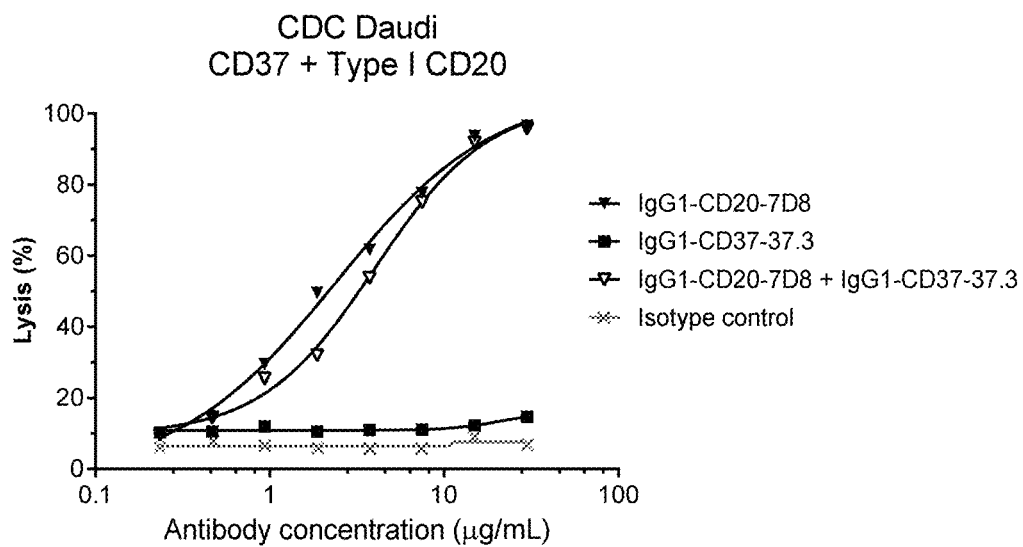
FIGS. 1A and 1B show CDC activity of mixtures of wild type (WT) CD20 and CD37 antibodies on Daudi cells. CDC on Daudi cells opsonized with concentration series WT CD37 antibody IgG1-CD37-37.3 mixed with (FIG. 1A) WT type I CD20 antibody IgG1-CD20-7D8 or (FIG. 1B) WT type II CD20 antibody IgG1-CD20-11B8. The percentage lysis is expressed as the PI-positive cell fraction as determined by flow cytometry.

The term "CD37", as used herein, refers to Leukocyte Antigen CD37, also known as GP52-40, tetraspanin-26, and TSPAN26, which is a heavily glycosylated transmembrane protein with four transmembrane domains (TMs) and one small and one large extracellular domain. Homo sapiens, i.e., human, CD37 protein is encoded by a nucleic acid sequence encoding the amino acid sequence shown in SEQ ID NO: 1 (human CD37 protein: UniprotKB/Swissprot P11049). In this amino acid sequence, residues 112 to 241 correspond to the large extracellular domain, residues 39 to 59 to the small extracellular domain, while the remaining residues correspond to transmembrane and cytoplasmic domains. *Macaca fascicularis*, i.e., cynomolgus monkey, CD37 protein is encoded by a nucleic acid sequence encoding the amino acid sequence shown in SEQ ID NO: 2 (cynomolgus CD37 protein: Genbank accession no. XP_005589942). Unless contradicted by context the term "CD37" means "human CD37". The term "CD37" includes any variants, isoforms and species homologs of CD37 which are naturally expressed by cells, including tumor cells, or are expressed on cells transfected with the CD37 gene or cDNA.

The term "antibody binding CD37", "anti-CD37 antibody", "CD37-binding antibody", "CD37-specific antibody", "CD37 antibody" which may be used interchangeably herein, refers to any antibody binding an epitope on the extracellular part of CD37.

The term "human CD20" or "CD20" refers to human CD20 (UniProtKB/Swiss-Prot No P11836) and includes any variants, isoforms and species homologs of CD20 which are naturally expressed by cells, including tumor cells, or are expressed on cells transfected with the CD20 gene or cDNA. Species homologs include rhesus monkey CD20 (macaca mulatta; UniProtKB/Swiss-Prot No H9YXP1).

The term "antibody binding CD20", "anti-CD20 antibody", "CD20-binding antibody", "CD20-specific antibody", "CD20 antibody" which may be used interchangeably herein, refers to any antibody binding an epitope on the extracellular part of CD20.

The term "antibody" (Ab) in the context of the present invention refers to an immunoglobulin molecule, a fragment of an immunoglobulin molecule, or a derivative of either thereof, which has the ability to specifically bind to an antigen. An antibody used in the present invention comprises an Fc-domain of an immunoglobulin and an antigen-binding region. An antibody generally contains a CH2-CH3 region and a connecting region, e.g. a hinge region, e.g. at least an Fc-domain. The variable regions of the heavy and light chains of the immunoglobulin molecule contain a binding domain that interacts with an antigen. An antibody may also be a monospecific or a multispecific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363:446); ThioMabs (Roche, WO2011069104); strand-exchange engineered domain (SEED or Seed-body) which are asymmetric and bispecific antibody-like molecules (Merck, WO2007110205); Triomab (Pharma/Fresenius Biotech, Lindhofer et al. 1995 J Immunol 155:219; WO2002020039); FcΔAdp (Regeneron, WO2010151792), Azymetric Scaffold (Zymeworks/Merck, WO2012/058768); mAb-Fv (Xencor, WO2011/028952), Xmab (Xencor); Dual variable domain immunoglobulin (Abbott, DVD-Ig, U.S. Pat. No. 7,612,181); Dual domain double head antibodies (Unilever; Sanofi Aventis, WO20100226923); Di-diabody (ImClone/Eli Lilly); Knobs-into-holes antibody formats (Genentech, WO9850431); DuoBody (Genmab, WO 2011/131746); Bispecific IgG1 and IgG2 (Pfizer/Rinat, WO11143545); DuetMab (MedImmune, US2014/0348839); Electrostatic steering antibody formats (Amgen, EP1870459 and WO 2009089004; Chugai, US201000155133; Oncomed, WO2010129304A2); CrossMAbs (Roche, WO2011117329); LUZ-Y (Genentech), Biclonic (Merus, WO2013157953); Dual Targeting domain antibodies (GSK/Domantis); Two-in-one Antibodies or Dual action Fabs recognizing two targets (Genentech, NovImmune, Adimab); Cross-linked Mabs (Karmanos Cancer Center); covalently fused mAbs (AIMM), CovX-body (CovX/Pfizer); FynomAbs (Covagen/Janssen cilag); DutaMab (Dutalys/Roche); iMab (MedImmune); IgG-like Bispecific (ImClone/Eli Lilly, Shen, J., et al. J Immunol Methods, 2007. 318(1-2): p. 65-74); TIG-body, DIG-body and PIG-body (Pharmabcine); Dual-affinity retargeting molecules (Fc-DART or Ig-DART, by Macrogenics, WO/2008/157379, WO/2010/080538); BEAT (Glenmark); Zybodies (Zyngenia); approaches with common light chain (Crucell/Merus, U.S. Pat. Nno. 7,262,028) or common heavy chains (κλBodies by NovImmune, WO2012023053), as well as fusion proteins comprising a polypeptide sequence fused to an antibody fragment containing an Fc-domain like scFv-fusions, like BsAb by ZymoGenetics/BMS, HERCULES by Biogen Idec (US007951918), SCORPIONS by Emergent BioSolutions/Trubion and Zymogenetics/BMS, Ts2Ab (MedImmune/AZ (Dimasi, N., et al. J Mol Biol, 2009. 393(3): p. 672-92), scFv fusion by Genentech/Roche, scFv fusion by Novartis, scFv fusion by Immunomedics, scFv fusion by Changzhou Adam Biotech Inc (CN 102250246), TvAb by Roche (WO 2012025525, WO 2012025530), mAb$^2$ by f-Star (WO2008/003116), and dual scFv-fusions. It also should be understood that the term antibody, unless specified otherwise, also includes polyclonal antibodies, monoclonal antibodies (such as human monoclonal antibodies), antibody mixtures (recombinant polyclonals) for instance generated by technologies exploited by Symphogen and Merus (Oligoclonics), multimeric Fc proteins as described in WO2015/158867, fusion proteins as described in WO2014/031646 and antibody-like polypeptides, such as chimeric antibodies and humanized antibodies. An antibody as generated can potentially be of any isotype.

The term "antigen-binding region", "antigen binding region", "binding region" or antigen binding domain, as used herein, refers to a region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion or in solution. The terms "antigen" and "target" may, unless contradicted by the context, be used interchangeably in the context of the present invention.

The term "target", as used herein, refers to a molecule to which the antigen binding region of the antibody binds. The target includes any antigen towards which the raised antibody is directed. The term "antigen" and "target" may in relation to an antibody be used interchangeably and constitute the same meaning and purpose with respect to any aspect or embodiment of the present invention.

The term "full-length antibody", as used herein, refers to an antibody (e.g., a parent or variant antibody) which contains all heavy and light chain constant and variable domains corresponding to those that are normally found in a wild-type antibody of that class or isotype.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine, rabbit) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "oligomer", as used herein, refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Likewise, "oligomerization" such as e.g. "hexamerization", as used herein, means that there is an increase in the distribution of antibodies and/or other dimeric proteins comprising target-binding regions according to the invention into oligomers, such as hexamers. The increased formation of oligomers such as hexamers is due to increased Fc-Fc interaction after binding to membrane-bound targets, thus the increased formation of oligomers is when an antibody comprising an Fc-Fc interaction enhancing substitution is compared to the same antibody without an Fc-Fc interaction enhancing substitution.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody (i.e. the non-human antibody from which the six CDRs were obtained), the substitution of framework residues from the parental antibody into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

Humanized antibodies can be generated using immunized rabbits, humanization of rabbit antibodies using germline humanization (CDR-grafting) technology, and, if necessary, by back-mutating residues which may be critical for the antibody binding properties, as identified in structural modeling, to rabbit residues. Screening for potential T cell epitopes can be applied.

The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). Such amino acid residues may be added or delete by non-human enzymes, e.g. if the antibody is generated in a transgenic animal comprising human germline immunoglobulin sequences. However, the term "human antibody", as used herein, is not intended to include antibodies in which CDR sequences derived from the germline of another mammalian species, such as a mouse, have been grafted onto human framework sequences. Human monoclonal antibodies of the invention can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

A suitable animal system for preparing hybridomas that secrete human monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Human monoclonal antibodies can be generated using e.g. transgenic or transchromosomal mice or rabbits carrying parts of the human immune system rather than the mouse or rabbit system.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as VH or VH) and a heavy chain constant region (abbreviated herein as $C_H$ or CH). The heavy chain constant region typically is comprised of three domains, $C_H1$, $C_H2$, and $C_H3$. Each light chain typically is comprised of a light chain variable region (abbreviated herein as $V_L$ or VL) and a light chain constant region (abbreviated herein as $C_L$ or CL). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008;36:W503-508 and Lefranc MP., Nucleic Acids Research 1999;27:209-212; see also internet http address http://www.imgt.org/). Unless otherwise stated or contradicted by context, reference to amino acid positions in the constant regions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

When used herein, unless contradicted by context, the term "Fab-arm" or "arm" refers to one heavy chain-light chain pair and is used interchangeably with "half molecules" herein. Accordingly, a "Fab-arm" comprises the variable regions of the heavy chain and light chain as well as the constant region of the light chain and the constant region of the heavy chain which comprises the CH1 region, the hinge, the CH2 region and the CH3 region of an immunoglobulin. The "CH1 region" refers e.g. to the region of a human IgG1 antibody corresponding to amino acids 118-215 according to the EU numbering. Thus, the Fab fragment comprises the binding region of an immunoglobulin.

The term "fragment crystallizable region", "Fc region", "Fc-region" "Fc fragment" or "Fc domain", which may be used interchangeably herein, refers to an antibody region comprising, arranged from amino-terminus to carboxy-terminus, at least a hinge region, a CH2 domain and a CH3 domain. An Fc region of an IgG1 antibody can, for example, be generated by digestion of an IgG1 antibody with papain. The Fc region of an antibody may mediate the binding of the immunoglobulin to host tissues or factors, including various cells of the immune system (such as effector cells) and components of the complement system such as C1q, the first component in the classical pathway of complement activation. The term "hinge region", as used herein, is intended to refer to the hinge region of an immunoglobulin heavy chain. Thus, for example the hinge region of a human IgG1 antibody corresponds to amino acids 216-230 according to the EU numbering. The term "core hinge" or "core hinge region" as used herein refers to the four amino acids corresponding to positions 226-229 of a human IgG1 antibody.

The term "CH2 region" or "CH2 domain", as used herein, is intended to refer the CH2 region of an immunoglobulin heavy chain. Thus, for example the CH2 region of a human IgG1 antibody corresponds to amino acids 231-340 according to the EU numbering. However, the CH2 region may also be any of the other isotypes or allotypes as described herein.

The term "CH3 region" or "CH3 domain" as used herein, is intended to refer to the CH3 region of an immunoglobulin heavy chain. Thus, for example the CH3 region of a human IgG1 antibody corresponds to amino acids 341-447 according to the EU numbering. However, the CH3 region may also be any of the other isotypes or allotypes as described herein.

As used herein, the term "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not capable of antigen crosslinking.

The term "epitope" means a protein determinant capable of binding to an antigen-binding region of an antibody ("paratope"). Epitopes usually consist of surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. Epitope mapping techniques can determine "structural epitopes" or "functional epitopes". Structural epitopes are defined as those residues within a structure that are in direct contact with the antibody and can for example be assessed by structure based methods such as X-ray crystallography. A structural epitope may comprise amino acid residues directly involved in the binding of an antibody as well as other amino acid residues, which are not directly involved in the binding, such as amino acid residues which are effectively blocked or covered by antibody (in other words, the amino acid residue is within the footprint of the antibody). Functional epitope are defined as those residues that make energetic contributions to the antigen-antibody binding interaction and can for example be assessed by site-directed mutagenesis such as alanine scanning (Cunningham, B. C., & Wells, J. A. (1993) *Journal of Molecular Biology*; Clackson, T., & Wells, J. (1995) *Science*, 267(5196), 383-386). A functional epitope may comprise amino acid residues directly involved in the binding of an antibody as well as other amino acid residues which are not directly involved in the binding, such as amino acid residues which cause conformational changes to the location of residues involved in direct interactions (Greenspan, N. S., & Di Cera, E. (1999) *Nature Biotechnology*, 17(10), 936-937). In case of antibody-antigen interactions, the functional epitope may be used to distinguish antibody molecules between each other. A functional epitope may be determined by use of the method of alanine scanning. Thus, amino acids in the protein may be substituted with alanines thereby generating a series of mutant proteins, binding of the antigen-binding region of the antibody to the mutant protein is reduced as compared to a wild type protein; reduced binding being determined as standardized log(fold change) (expressed as z-scores) in binding of said antibody being less than −1.5.

The term "monoclonal antibody" as used herein refers to a preparation of antibody molecules essentially of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction.

"Affinity", as used herein, and "$K_D$" are inversely related, that is, higher affinity is intended to refer to lower $K_D$, and lower affinity is intended to refer to higher $K_D$.

As used herein, an antibody which "competes" or "cross-competes" is used interchangeably with an antibody which "blocks" or "cross-blocks" with another antibody, i.e. a reference antibody, and means that the antibody and the reference antibody compete for binding to human CD37 or human CD20. In one embodiment the antibody binds with less than 50%, such as less than 20%, such as less than 15% of its maximum binding in the presence of the competing reference antibody.

As used herein, an antibody which "does not compete" or "does not cross-compete" or "does not block" with another antibody, i.e. a reference antibody, means that the antibody and the reference antibody do not compete for binding to human CD37 or human CD20. For some pairs of antibody and reference antibody, non-competition is only observed when one antibody is bound to an antigen on a cell and the other is used to compete, and not vice versa. The term "does not compete with" or "non-competition" or "non-blocking" when used herein is also intended to cover such combinations of antibodies. In one embodiment the antibody binds with at least 75%, such as least 80%, such as at least 85% of its maximum binding in the presence of the reference antibody.

The term "Fc-Fc interaction enhancing substitution", as used herein, refers to a substitution in IgG antibodies that strengthens Fc-Fc interactions between neighboring IgG antibodies that are bound to a cell surface target. This may result in enhanced oligomer formation such as e.g. hexamerization of the target-bound antibodies, while the antibody molecules remain monomeric in solution as described in WO 2013/004842 and WO 2014/108198, both which are hereby incorporated by reference. The Fc-Fc interaction enhancing substitution according to the present invention is a substitution in the Fc region of an amino acid at a position corresponding to E430, E345 or S440 in human IgG1 when using EU numbering system, with the proviso that the substitution in S440 is S440Y or S440W. Thus, the Fc-Fc interaction enhancing substitution may be selected form the group consisting of: E430G, E345K, E430S, E430F, E430T, E345Q, E345R, E345Y, S440Y and S440W.

The term "Fc effector functions" or "Fc-mediated effector functions" as used herein, is intended to refer to functions that are a consequence of binding an antibody to its target, such as an antigen, on a cell membrane, and subsequent interaction of the IgG Fc domain with molecules of the innate immune system (e.g. soluble molecules or membrane-bound molecules). Examples of Fc effector functions include (i) C1q-binding, (ii) complement activation, (iii) complement-dependent cytotoxicity (CDC), (iv) antibody-dependent cell-mediated cytotoxicity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity, (ix) binding to complement receptor of an opsonized antibody mediated by the antibody, (x) opsonisation, and (xi) a combination of any of (i) to (x).

The present invention also provides antibodies comprising functional variants of the $V_L$ regions, $V_H$ regions, or one or more CDRs of the antibodies of the examples. A functional variant of a $V_L$, $V_H$, or CDR used in the context of an antibody still allows each arm of the antibody to retain at least a substantial proportion (at least about 50%, 60%, 70%, 80%, 90%, 95% or more) of the affinity and/or the specificity/selectivity of the parent antibody and in some cases such an antibody may be associated with greater affinity, selectivity and/or specificity than the parent antibody. Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from VH and/or VL and/or CDR regions of the parent bispecific antibody sequences mainly by conservative substitutions; for instance 10, such as 9, 8, 7, 6, 5, 4, 3, 2 or 1 of the substitutions in the variant are conservative amino acid residue replacements. Preferably, a variant contains at most 10 amino acid substitutions in the VH and/or VL region of the parent antibody, such as at most 9, 8, 7, 6, 5, 4, 3, 2 or at most 1 amino acid substitution. Preferably such substitutions are conservative substitutions especially so if the substitutions are in a CDR sequence.

In the context of the present invention, conservative substitutions may be defined by substitutions within the classes of amino acids reflected in the following table:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In the context of the present invention the following notations are, unless otherwise indicated, used to describe a mutation; i) substitution of an amino acid in a given position is written as e.g. E430G which means a substitution of a Glutamine in position 430 with an Glycine; and ii) for specific variants the specific three or one letter codes are used, including the codes Xaa and X to indicate any amino acid residue. Thus, the substitution of Glutamine with Glycine in position 409 is designated as: E430G, and the substitution of Glutamine with any amino acid residue in position 430 is designated as E430X.

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO, CHO-S, HEK, HEK293, HEK-293F, Expi293F, PER.C6 or NS0 cells, and lymphocytic cells.

The term "treatment" refers to the administration of an effective amount of a therapeutically active composition of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of a bispecific antibody may vary according to factors such as the disease state, age, sex, and weight of the individual, and the ability of the bispecific antibody to elicit a desired response in the individual. A therapeutically effective amount is also one in which any toxic or detrimental effects of the antibody or antibody portion are outweighed by the therapeutically beneficial effects.

Embodiments of the Invention

In a first main aspect the invention relates to a first antibody comprising a first antigen binding region capable of binding to human CD37 and a first Fc-region of a human IgG, for use as a medicament in combination with a second antibody comprising a second antigen binding region capable of binding to human CD20 and a second Fc region of a human IgG, wherein the first Fc region and the second Fc region each comprises a substitution of an amino acid at a position corresponding to E430, E345 or S440, in human IgG1 according to EU numbering system, with the proviso that the substitution in S440 is S440Y or S440W. Hereby antibodies are provided wherein the Fc region comprises an Fc-Fc interaction enhancing substitution. Thus, the antibody molecules may form oligomers upon target binding; such oligomers may form between anti-CD37 antibody molecules alone, anti-CD20 antibody molecules alone, or between a mixture of anti-CD37 antibody and anti-CD20 antibody molecules. In one embodiment the first antibody is an anti-CD37 antibody and the second antibody is an anti-CD20 antibody.

A first antibody according to the present invention may be an anti-CD37 antibody having an Fc region comprising a first and a second heavy chain, wherein a substitution at a position corresponding to E430, E345 or S440, in human IgG1 when using EU numbering, with the proviso that the substitution in S440 is S440Y or S440W, is present in the first or the second heavy chain, or preferred present in both the first and the second heavy chains.

A second antibody according to the present invention may be an anti-CD20 antibody having an Fc region comprising a first and a second heavy chain, wherein a substitution at a position corresponding to E430, E345 or S440, in human IgG1 when using EU numbering, with the proviso that the substitution in S440 is S440Y or S440W, is present in the first or the second heavy chain, or preferred present in both the first and the second heavy chains.

In one embodiment of the invention the first Fc region comprises a substitution selected from the group consisting of: E430G, E345K, E430S, E430F, E430T, E345Q, E345R, E345Y, S440Y and S440W.

In one embodiment of the invention the second Fc region comprises a substitution selected from the group consisting of: E430G, E345K, E430S, E430F, E430T, E345Q, E345R, E345Y, S440Y and S440W.

In one embodiment of the invention the first Fc region and the second Fc region comprises a substitution selected from the group consisting of: E430G, E345K, E430S, E430F, E430T, E345Q, E345R, E345Y, S440Y and S440W.

In one embodiment of the invention the first Fc region comprises a substitution selected from the group consisting of: E430G, E345R and E345K.

In one embodiment of the invention the second Fc region comprises a substitution selected from the group consisting of: E430G, E345R and E345K.

In one embodiment of the invention the first Fc region comprises a substitution selected from the group consisting of: E430G and E345K, preferably E430G.

In one embodiment of the invention the second Fc region comprises a substitution selected from the group consisting of: E430G and E345K, preferably E430G.

In one embodiment of the invention the first Fc region comprises an E430G substitution.

In one embodiment of the invention the second Fc region comprises an E430G substitution.

In one embodiment of the invention the first Fc region and second Fc region comprise a substitution selected from the group consisting of: E430G and E345K, preferably E430G.

In one embodiment of the invention the first Fc region and second Fc region comprise an E430G substitution. In one embodiment of the invention the first Fc region and second Fc region comprise an E4305 substitution. In one embodiment of the invention the first Fc region and second Fc region comprise an E430F substitution. In one embodiment of the invention the first Fc region and second Fc region comprise an E430T substitution. In one embodiment of the invention the first Fc region and second Fc region comprise an E345K substitution. In one embodiment of the invention the first Fc region and second Fc region comprise an E345R substitution. In one embodiment of the invention the first Fc region and second Fc region comprise an E345Q substitution. In one embodiment of the invention the first Fc region and second Fc region comprise an E345Y substitution. In one embodiment of the invention the first Fc region and second Fc region comprise an S440Y substitution. In one embodiment of the invention the first Fc region and second Fc region comprise an S440W substitution.

In one embodiment of the invention the first antibody comprises a first antigen-binding region capable of binding to human CD37 and a first Fc-region of a human IgG and a second antibody comprises a second antigen-binding region capable of binding to human CD20 and a second Fc-region of a human IgG, wherein the first Fc region comprises an E430G substitution. Thus, in one embodiment the first antibody may have an Fc region which has an Fc-Fc interaction enhancing substitution and the second antibody does not have an Fc-Fc interaction enhancing substitution according to the present invention.

In one embodiment of the invention the first Fc region and second Fc region comprise an E430G substitution. In one embodiment of the invention the first Fc region and second Fc region comprise an E4305 substitution. In one embodiment of the invention the first Fc region and second Fc region comprise an E430F substitution. In one embodiment of the invention the first Fc region and second Fc region comprise an E430T substitution. In one embodiment of the invention the first Fc region and second Fc region comprise an E345K substitution. In one embodiment of the invention the first Fc region and second Fc region comprise an E345R substitution. In one embodiment of the invention the first Fc region and second Fc region comprise an E345Q substitution. In one embodiment of the invention the first Fc region and second Fc region comprise an E345Y substitution. In one embodiment of the invention the first Fc region and second Fc region comprise an S440Y substitution. In one embodiment of the invention the first Fc region and second Fc region comprise an S440W substitution.

In one embodiment of the invention the composition comprises a first and a second antibody, wherein the first and the second Fc region comprise a further substitution in addition to the Fc-Fc interaction enhancing substitution. Examples of such further substitutions may be S440K and/or K439E. Antibodies comprising an Fc-Fc interaction enhancing substitution and a further S440K substitution do not form oligomers with antibodies comprising an S440K substitution. Antibodies comprising an Fc-Fc interaction enhancing substitution and a further K439E substitution do not form oligomers with antibodies comprising a K439E substitution. However, antibodies comprising an Fc-Fc interaction enhancing substitution and a further K439E substitution do form oligomers with antibodies comprising an Fc-Fc interaction enhancing substitution and a further S440K substitution. Thus, a first antibody comprising an Fc-Fc interaction enhancing substitution and a further K439E substitution and a second antibody comprising an Fc-Fc interaction enhancing substitution and a S440K substitution may form hetero-oligomers, such as hetero-hexamers, on the cell surface of a cell expressing the corresponding antigens for both the first and the second antibody.

In one embodiment of the invention the first Fc region further comprises a K439E substitution and the second Fc region further comprises an S440K substitution, with the proviso that the second Fc region does not comprise an S440Y or S440W substitution. Alternatively, in one embodiment the first Fc region further comprises an S440K substitution, with the proviso that the first Fc region does not comprise an S440Y or S440W substitution and the second Fc region further comprises a K439E substitution.

In one embodiment of the invention the first Fc region comprises a substitution of an amino acid at a position corresponding to E430 and a further K439E substitution and a second Fc region comprises a substitution of an amino acid at a position corresponding to E430 and a further S440K substitution.

In one embodiment of the invention the first Fc region comprises a substitution of an amino acid at a position corresponding to E430 and a further S440K substitution and a second Fc region comprises a substitution of an amino acid at a position corresponding to E430 and a further K439E substitution.

In one embodiment of the invention the first Fc region comprises an E430G substitution and a further K439E substitution and the second Fc region comprises an E430G substitution and a further S440K substitution.

In one embodiment of the invention the first Fc region comprises an E430G substitution and a further S440K substitution and the second Fc region comprises an E430G substitution and a further K439E substitution.

In one embodiment of the invention the first Fc region comprises a substitution of an amino acid at a position corresponding to E345 and a further K439E substitution and the second Fc region comprises a substitution of an amino acid at a position corresponding to E345 and a further S440K substitution.

In one embodiment of the invention the first Fc region comprises a substitution of an amino acid at a position corresponding to E345 and a further S440K substitution and the second Fc region comprises a substitution of an amino acid at a position corresponding to E345 and a further K439E substitution.

In one embodiment of the invention the first Fc region comprises an E345K substitution and a further K439E substitution and a second Fc region comprises an E345K substitution and a further S440K substitution.

In one embodiment of the invention the first Fc region comprises an E345K substitution and a further S440K substitution and the second Fc region comprises an E345K substitution and a further K439E substitution.

In one embodiment of the invention the first antibody for use as a medicament in combination with a second antibody, has a first antigen-binding region which binds to human CD37 having the sequences set forth in SEQ ID No 1.

In one embodiment of the invention the first antibody for use as a medicament in combination with a second antibody, has a first antigen-binding region which binds to cynomolgus monkey (*Macaca fascicularis*) CD37 having the sequences set forth in SEQ ID No 2.

In one embodiment of the invention the first antibody for use as a medicament in combination with a second antibody, has a first antigen-binding region which binds to human CD37 having the sequences set forth in SEQ ID No 1 and cynomolgus monkey (*Macaca fascicularis*) CD37 having the sequences set forth in SEQ ID No 2 and the second antibody has a second antigen-binding region which binds to human CD20.

In one embodiment of the invention the first antibody for use as a medicament in combination with a second antibody, has a first antigen-binding region which binds to a functional epitope comprising the amino acids Y182, D189, T191, I192, D194, K195, V196, I197 and P199 of SEQ ID No 1

In one embodiment of the invention the first antibody for use as a medicament in combination with a second antibody, has a first antigen-binding region which binds to a functional epitope comprising the amino acids E124, F162, Q163, V164, L165 and H175 of SEQ ID No 1.

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 selected from the group consisting of:
  a. SEQ ID No: 22, 23, 24, respectively [004],
  b. SEQ ID No:29, 30, 31, respectively [005],
  c. SEQ ID No:36, 37, 38, respectively [010],
  d. SEQ ID No:43, 44, 45, respectively [016],
  e. SEQ ID No: 8, 9, 10, respectively, and
  f. SEQ ID No:15, 16, 17, respectively.

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 as set forth in SEQ ID No: 22, 23, 24, respectively [004].

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 as set forth in SEQ ID No: 29, 30, 31, respectively [005].

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 as set forth in SEQ ID No:36, 37, 38, respectively [010].

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 as set forth in SEQ ID No:43, 44, 45, respectively [016].

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 as set forth in SEQ ID No: 8, 9, 10, respectively.

In one embodiment of the invention the first antibody for use as a medicament in combination with a second antibody, has a first antigen-binding region binding to human CD37 which comprises a variable heavy chain (VH), wherein the VH comprises three CDR sequences HCDR1, HCDR2 and HCDR3 as set forth in SEQ ID No:15, 16, 17, respectively.

In one embodiment of the invention the first antibody for use as a medicament in combination with a second antibody, has a first antigen-binding region binding to human CD37 which comprises a variable light chain (VL), wherein the VL comprises three CDR sequences LCDR1, LCDR2 and LCDR3 selected from the group consisting of:
  a. SEQ ID No: 26, EAS, 27, respectively [004],
  b. SEQ ID No: 33, AAS, 34, respectively [005],
  c. SEQ ID No: 40, KAS, 41, respectively [010],
  d. SEQ ID No: 47, YAS, 48, respectively [016],
  e. SEQ ID No: 47, YAS, 58, respectively [016-C90S],
  f. SEQ ID No: 12, VAT, 13, respectively, and
  g. SEQ ID No: 19, FAK, 20, respectively.

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and
  g. SEQ ID No: 15, 16, 17, 19, FAK, 20, respectively.

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 22, 23, 24, 26, EAS, 27, respectively [004].

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 29, 30, 31, 33, AAS, 34 respectively [005].

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 36, 37, 38, 40, KAS, 41, respectively [010].

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 43, 44, 45, 47, YAS, 48 respectively [016].

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 43, 44, 45, 47, YAS, 58 respectively [016-C90S].

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 8, 9, 10, 12, VAT, 13 respectively.

In one embodiment of the invention the first antibody for use as a medicament in combination with a second antibody, has a first antigen-binding region binding to human CD37 which comprises a VH comprising three CDR sequences HCDR1, HCDR2 and HCDR3 and a VL comprising three CDR sequences LCDR1, LCDR2 and LCDR3 as set forth in SEQ ID No: 15, 16, 17, 19, FAK, 20 respectively.

In one embodiment of the invention the first antibody for use as a medicament in combination with a second antibody, has a first antigen-binding region binding to human CD37 which comprises a VH and VL having sequences selected from the group consisting of:
  a. VH SEQ ID No: 49, and VL SEQ ID No 50, respectively [004],
  b. VH SEQ ID No: 51, and VL SEQ ID No 52, respectively [005],
  c. VH SEQ ID No: 53, and VL SEQ ID No 54, respectively [010],
  d. VH SEQ ID No: 55, and VL SEQ ID No 56, respectively [016],
  e. VH SEQ ID No: 55, and VL SEQ ID No 57, respectively [016-C90S],1
  f. VH SEQ ID No: 7, and VL SEQ ID No 11, respectively,
  g. VH SEQ ID No: 14, and VL SEQ ID No 18, respectively, and
  h. a VH and VL sequence having at least 90%, at least 95%, at least 97 or at least 99% amino acid sequence identity to any one of the sequences as set forth in a) to f).

In one embodiment of the invention the first antibody for use as a medicament in combination with a second antibody, has a first antigen-binding region binding to human CD37 which comprises a VH and VL having sequences selected from the group consisting of:
  a. VH SEQ ID No: 49, and VL SEQ ID No 50, respectively [004],
  b. VH SEQ ID No: 51, and VL SEQ ID No 52, respectively [005],
  c. VH SEQ ID No: 53, and VL SEQ ID No 54, respectively [010],
  d. VH SEQ ID No: 55, and VL SEQ ID No 56, respectively [016],
  e. VH SEQ ID No 55, and VL SEQ ID No 57, respectively [016-C90S],
  f. VH SEQ ID No: 7, and VL SEQ ID No 11, respectively, and
  g. VH SEQ ID No: 14, and VL SEQ ID No 18, respectively.

In one embodiment of the invention the first antibody for use as a medicament in combination with a second antibody, wherein the second antibody has a second antigen-binding region which binds to human and cynomolgus monkey CD20 having the sequences set forth in SEQ ID Nos 5 and 6, respectively.

In one embodiment of the invention the first antibody for use as a medicament in combination with a second antibody, wherein the second antibody has a second antigen-binding region which binds to human CD20 comprising a VH, wherein the VH comprises three CDR sequences HCDR1, HCDR2 and HCDR3 selected from the group consisting of:
  a. SEQ ID No: 60, 61, 62, respectively [7D8],
  b. SEQ ID No: 67, 68, 69, respectively [11B8],
  c. SEQ ID No: 73, 74, 62, respectively [Ofatumumab],
  d. SEQ ID No: 76, 77, 78, respectively [Rituximab], and
  e. SEQ ID No: 83, 84, 85, respectively [obinutuzumab].

In one embodiment of the invention the first antibody for use as a medicament in combination with a second antibody, wherein the second antibody has a second antigen-binding region which binds to human CD20 comprising a VH, wherein the VH comprises three CDR sequences HCDR1, HCDR2 and HCDR3 as set forth in SEQ ID No: 60, 61, 62, respectively [7D8].

In one embodiment of the invention the first antibody for use as a medicament in combination with a second antibody, wherein the second antibody has a second antigen-binding region which binds to human CD20 comprising a VH, wherein the VH comprises three CDR sequences HCDR1, HCDR2 and HCDR3 as set forth in SEQ ID No: 67, 68, 69, respectively [11B8].

In one embodiment of the invention the first antibody for use as a medicament in combination with a second antibody, wherein the second antibody has a second antigen-binding region which binds to human CD20 comprising a VH, wherein the VH comprises three CDR sequences HCDR1, HCDR2 and HCDR3 as set forth in SEQ ID No: 73, 74, 62, respectively [Ofatumumab].

In one embodiment of the invention the first antibody for use as a medicament in combination with a second antibody, wherein the second antibody has a second antigen-binding region which binds to human CD20 comprising a VH, wherein the VH comprises three CDR sequences HCDR1, HCDR2 and HCDR3 as set forth in SEQ ID No: 76, 77, 78, respectively [Rituximab].

In one embodiment of the invention the first antibody for use as a medicament in combination with a second antibody, wherein the second antibody has a second antigen-binding region which binds to human CD20 comprising a VH, wherein the VH comprises three CDR sequences HCDR1, HCDR2 and HCDR3 as set forth in SEQ ID No: 83, 84, 85, respectively [obinutuzumab].

In one embodiment of the invention the first antibody for use as a medicament in combination with a second antibody, wherein the second antibody has a second antigen-binding region binding to human CD20 comprises a VL, wherein the VL comprises three CDR sequences LCDR1, LCDR2 and LCDR3 selected from the group consisting of:
  a. SEQ ID No: 64, DAS, 65, respectively [7D8]/[Ofatumumab],
  b. SEQ ID No: 64, DAS, 71, respectively [11B8],
  c. SEQ ID No: 80, ATS, 81, respectively [Rituximab],
  d. SEQ ID No: 87, QMS, 88, respectively [obinutuzumab].

In one embodiment of the invention the first antibody for use as a medicament in combination with a second antibody, wherein the second antibody has a second antigen-binding region binding to human CD20 comprises a VH, wherein the VH comprises three CDR sequences HCDR1, HCDR2 and HCDR3 and a VL wherein the VL comprises three CDR sequences LCDR1, LCDR2 and LCDR3 selected from the group consisting of:
  a. SEQ ID No: 60, 61, 62,64, DAS, 65, respectively [7D8],
  b. SEQ ID No: 67, 68, 69, 64, DAS, 71, respectively [11B8],
  c. SEQ ID No: 73, 74, 62, 64, DAS, 65, respectively [Ofatumumab],
  d. SEQ ID No: 76, 77, 78, 80, ATS, 81, respectively [Rituximab], and
  e. SEQ ID No: 83, 84, 85, 87, QMS, 88 respectively.

In one embodiment of the invention the first antibody for use as a medicament in combination with a second antibody, wherein the second antibody has a second antigen-binding region binding to human CD20 comprises a VH, wherein the VH comprises three CDR sequences HCDR1, HCDR2 and HCDR3 and a VL wherein the VL comprises three CDR sequences LCDR1, LCDR2 and LCDR3 as set forth in SEQ ID No: 60, 61, 62, 64, DAS, 65, respectively [7D8].

In one embodiment of the invention the first antibody for use as a medicament in combination with a second antibody, wherein the second antibody has a second antigen-binding region binding to human CD20 comprises a VH, wherein the VH comprises three CDR sequences HCDR1, HCDR2 and HCDR3 and a VL wherein the VL comprises three CDR sequences LCDR1, LCDR2 and LCDR3 as set forth in SEQ ID No: 67, 68, 69, 64, DAS, 71, respectively [11B8].

In one embodiment of the invention the first antibody for use as a medicament in combination with a second antibody, wherein the second antibody has a second antigen-binding region binding to human CD20 comprises a VH, wherein the VH comprises three CDR sequences HCDR1, HCDR2 and HCDR3 and a VL wherein the VL comprises three CDR sequences LCDR1, LCDR2 and LCDR3 as set forth in SEQ ID No: 73, 74, 62, 64, DAS, 65, respectively [Ofatumumab].

In one embodiment of the invention the first antibody for use as a medicament in combination with a second antibody, wherein the second antibody has a second antigen-binding region binding to human CD20 comprises a VH, wherein the VH comprises three CDR sequences HCDR1, HCDR2 and HCDR3 and a VL wherein the VL comprises three CDR sequences LCDR1, LCDR2 and LCDR3 as set forth in SEQ ID No: 76, 77, 78, 80, ATS, 81, respectively [Rituximab].

In one embodiment of the invention the first antibody for use as a medicament in combination with a second antibody, wherein the second antibody has a second antigen-binding region binding to human CD20 comprises a VH, wherein the VH comprises three CDR sequences HCDR1, HCDR2 and HCDR3 and a VL wherein the VL comprises three CDR sequences LCDR1, LCDR2 and LCDR3 as set forth in SEQ ID No: 83, 84, 85, 87, QMS, 88 respectively.

In one embodiment of the invention the first antibody for use as a medicament in combination with a second antibody, wherein the second antibody has a second antigen-binding region binding to human CD20 comprises a VH and VL having sequences selected from the group consisting of:
  a. VH SEQ ID No: 59, and VL SEQ ID No: 63 [7D8],
  b. VH SEQ ID No: 66, and VL SEQ ID No: 70 [11B8],
  c. VH SEQ ID No: 72, and VL SEQ ID No: 63 [Ofatumumab
  d. VH SEQ ID No: 75, and VL SEQ ID No: 79 [Rituximab],
  e. VH SEQ ID No: 82, and VL SEQ ID No: 86 [Obinutuzumab], and
  f. a VH and VL sequence having at least 90%, at least 95%, at least 97 or at least 99% amino acid sequence identity to any one of the sequences as set forth in a) to e).

In one embodiment of the invention the first antibody for use as a medicament in combination with a second antibody, wherein the second antibody has a second antigen-binding region binding to human CD20 comprises a VH and VL having sequences selected from the group consisting of:
  a. VH SEQ ID No: 59, and VL SEQ ID No: 63 [7D8],
  b. VH SEQ ID No: 66, and VL SEQ ID No: 70 [11B8],
  c. VH SEQ ID No: 72, and VL SEQ ID No: 63 [Ofatumumab]
  d. VH SEQ ID No: 75, and VL SEQ ID No: 79 [Rituximab], and
  e. VH SEQ ID No: 82, and VL SEQ ID No: 86 [Obinutuzumab].

In one embodiment of the invention the first antibody for use as a medicament in combination with a second antibody, wherein the first antigen binding region binding to human CD37 comprises a VH comprising the three CDR sequences HCDR1, HCDR2 and HCDR3 and a VL comprising the three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and
  g. SEQ ID No: 15, 16, 17, 19, FAK, 20, respectively,
  and the second antigen-binding region binding to human CD20 comprises a VH comprising the three CDR sequences HCDR1, HCDR2 and HCDR3 and a VL comprising the three CDR sequences LCDR1, LCDR2 and LCDR3 selected from the group consisting of:
  h. SEQ ID No: 60, 61, 62,64, DAS, 65, respectively [7D8],
  i. SEQ ID No: 67, 68, 69, 64, DAS, 71, respectively [1168],
  j. SEQ ID No: 73, 74, 62, 64, DAS, 65, respectively [Ofatumumab],
  k. SEQ ID No: 76, 77, 78, 80, ATS, 81, respectively [Rituximab], and
  l. SEQ ID No: 83, 84, 85 87, QMS, 88 respectively.

In one embodiment of the invention the first antibody for use as a medicament in combination with a second antibody, wherein the first antigen binding region binding to human CD37 comprises the VH and VL sequences selected from the group consisting of:
  a. VH SEQ ID No: 49, and VL SEQ ID No 50, respectively [004],
  b. VH SEQ ID No 51, and VL SEQ ID No 52, respectively [005],
  c. VH SEQ ID No 53, and VL SEQ ID No 54, respectively [010],
  d. VH SEQ ID No 55, and VL SEQ ID No 56, respectively [016],
  e. VH SEQ ID No 55, and VL SEQ ID No 57, respectively [016-C90S],
  f. VH SEQ ID No 7, and VL SEQ ID No 11, respectively, and
  g. VH SEQ ID No 14, and VL SEQ ID No 18, respectively, and the second antigen-binding region binding to human CD20 comprises the VH and VL sequences selected form the group consisting of:
  h. VH SEQ ID No: 59, and VL SEQ ID No: 63 respectively [7D8],
  i. VH SEQ ID No: 66, and VL SEQ ID No: 70 respectively [1188],
  j. VH SEQ ID No: 72, and VL SEQ ID No: 63 respectively [Ofatumumab
  k. VH SEQ ID No: 75, and VL SEQ ID No: 79 respectively [Rituximab], and
  l. VH SEQ ID No: 82, and VL SEQ ID No: 86 respectively [Obinutuzumab].

In one embodiment of the invention the first antibody for use as a medicament in combination with a second antibody, wherein the first antigen binding region binding to human CD37 comprises the VH and VL sequences as set forth in VH SEQ ID No: 49, and VL SEQ ID No: 50, respectively [004], and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 49, and VL SEQ ID No: 50, respectively [004], and the second antigen-binding region binding to human CD20 comprises the VH and VL sequences as set forth in VH SEQ ID No: 66, and VL SEQ ID No: 70 respectively [11B8]

In one embodiment of the invention the first antibody for use as a medicament in combination with a second antibody, wherein the first antigen binding region binding to human CD37 comprises the VH and VL sequences as set forth in VH SEQ ID No: 51, and VL SEQ ID No: 52, respectively [005], and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 51, and VL SEQ ID No: 52, respectively [005], and the second antigen-binding region binding to human CD20 comprises the VH and VL sequences as set forth in VH SEQ ID No: 66, and VL SEQ ID No: 70 respectively [11B8].

In one embodiment of the invention the first antibody for use as a medicament in combination with a second antibody, wherein the first antigen binding region binding to human CD37 comprises the VH and VL sequences as set forth in VH SEQ ID No: 53, and VL SEQ ID No: 54, respectively [010], and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 53, and VL SEQ ID No: 54, respectively [010], and the second antigen-binding region binding to human CD20 comprises the VH and VL sequences as set forth in VH SEQ ID No: 66, and VL SEQ ID No: 70 respectively [11B8].

In one embodiment of the invention the first antibody for use as a medicament in combination with a second antibody, wherein the first antigen binding region binding to human CD37 comprises the VH and VL sequences as set forth in VH SEQ ID No: 55, and VL SEQ ID No: 56, respectively

[016], and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 55, and VL SEQ ID No: 56, respectively [016], and the second antigen-binding region binding to human CD20 comprises the VH and VL sequences as set forth in VH SEQ ID No: 66, and VL SEQ ID No: 70 respectively [11B8].

In one embodiment of the invention the first antibody for use as a medicament in combination with a second antibody, wherein the first antigen binding region binding to human CD37 comprises the VH and VL sequences as set forth in VH SEQ ID No 55, and VL SEQ ID No 57, respectively [016-C90S], and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 55, and VL SEQ ID No: 57, respectively [016-C90S], and the second antigen-binding region binding to human CD20 comprises the VH and VL sequences as set forth in VH SEQ ID No: 66, and VL SEQ ID No: 70 respectively [11B8].

In one embodiment of the invention the first antibody for use as a medicament in combination with a second antibody, wherein the first antigen binding region binding to human CD37 comprises the VH and VL sequences as set forth in VH SEQ ID No: 7, and VL SEQ ID No: 11, respectively, and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 7, and VL SEQ ID No: 11, respectively, and the second antigen-binding region binding to human CD20 comprises the VH and VL sequences as set forth in VH SEQ ID No: 66, and VL SEQ ID No: 70 respectively [11B8].

In one embodiment of the invention the first antibody for use as a medicament in combination with a second antibody, wherein the first antigen binding region binding to human CD37 comprises the VH and VL sequences as set forth in VH SEQ ID No: 14, and VL SEQ ID No: 18, respectively, and the second antigen-binding region binding to human CD20 comprises the VH and VL sequences as set forth in VH SEQ ID No: 59, and VL SEQ ID No: 63 respectively [7D8].

In one embodiment of the invention the first antibody for use as a medicament in combination with a second antibody, wherein the first antigen binding region binding to human CD37 comprises the VH and VL sequences as set forth in VH SEQ ID No: 14, and VL SEQ ID No: 18, respectively, and the second antigen-binding region binding to human CD20 comprises the VH and VL sequences as set forth in VH SEQ ID No: 66, and VL SEQ ID No: 70 respectively [11B8].

In one embodiment of the invention the first antibody for use as a medicament in combination with a second antibody, wherein the first and/or second antibody is a human, humanized or chimeric antibody.

In one embodiment of the invention the first antibody for use as a medicament in combination with a second antibody, wherein the first antibody is humanized and the second antibody is human.

In one embodiment of the invention the first antibody for use as a medicament in combination with a second, wherein the first and/or second antibody is a monoclonal antibody.

In one embodiment of the invention the first antibody for use as a medicament in combination with a second, wherein the first and second antibody is a monoclonal antibody.

In one embodiment of the invention the first antibody for use as a medicament in combination with a second antibody, wherein the first and/or second antibody is a human IgG1, IgG2, IgG3 or IgG4 isotype.

In one embodiment of the invention the first antibody for use as a medicament in combination with a second antibody, wherein the first and second antibody is a human IgG1, IgG2, IgG3 or IgG4 isotype.

In one embodiment of the invention the first antibody for use as a medicament in combination with a second antibody, wherein the first and/or second antibody is an IgG1 isotype.

In one embodiment of the invention the first antibody for use as a medicament in combination with a second antibody, wherein the first and second antibody is a human IgG1 isotype.

In another aspect the invention relates to a composition comprising a first and a second antibody, wherein the first antibody comprises a first antigen-binding region capable of binding to human CD37 and a first Fc-region of a human IgG and the second antibody comprises a second antigen-binding region capable of binding to human CD20 and a second Fc-region of a human IgG, wherein the first and the second Fc region each comprisesa substitution of an amino acid at a position corresponding to E430, E345 or S440, in human IgG1 when using EU numbering system, with the proviso that the substitution in S440 is S440Y or S440W. Hereby a composition is provided which has an anti-CD37 antibody with an Fc-Fc interaction enhancing substitution in the Fc region and an anti-CD20 antibody with an Fc-Fc interaction enhancing substitution in the Fc region. Thus, the antibody molecules in such a composition may form oligomers upon target binding; such oligomers may form between anti-CD37 antibody molecules alone, anti-CD20 antibody molecules alone, or between a mixture of anti-CD37 antibody and anti-CD20 antibody molecules.

A composition according to the present invention comprises an anti-CD37 antibody having an Fc region comprising a first and a second heavy chain, wherein a substitution at a position corresponding to E430, E345 or S440, in human IgG1 when using EU numbering, with the proviso that the substitution in S440 is S440Y or S440W, is present in the first or the second heavy chain, or preferred present in both the first and the second heavy chains.

A substitution at an amino acid position corresponding to E430, E345 or S440, in human IgG1 according to EU numbering, with the proviso that the substitution in S440 is S440Y or S440W, is in the context of the present invention also referred to as an Fc-Fc interaction enhancing substitution.

The Fc-Fc interaction enhancing substitution strengthens the Fc-Fc interactions between antibodies comprising the substitution when bound to the corresponding antigen on a cell surface.

A composition according to the present invention also comprises an anti-CD20 antibody having an Fc region comprising a first and a second heavy chain, wherein a substitution at a position corresponding to E430, E345 or S440, in human IgG1 when using EU numbering, is present in both the first and the second heavy chain, or less preferred only present in one of the heavy chains, with the proviso that the substitution in S440 is S440Y or S440W.

A composition according to the present invention, wherein the anti-CD37 antibody has an Fc-Fc interaction enhancing substitution and the anti-CD20 antibody has an Fc-Fc interaction enhancing substitution, may be more potent in inducing CDC compared to the same anti-CD37 antibody having an Fc-Fc interaction enhancing substitution alone or the same anti-CD20 antibody having an Fc-Fc interaction enhancing substitution alone as illustrated in Examples 3, 4 and 8. In one embodiment of the invention the first Fc region comprises a substitution selected from the group consisting of: E430G, E345K, E430S, E430F, E430T, E345Q, E345R, E345Y, S440Y and S440W.

In one embodiment of the invention the second Fc region comprises a substitution selected from the group consisting of: E430G, E345K, E430S, E430F, E430T, E345Q, E345R, E345Y, S440Y and S440W.

In one embodiment of the invention the first Fc region and the second Fc region comprises a substitution selected from the group consisting of: E430G, E345K, E430S, E430F, E430T, E345Q, E345R, E345Y, S440Y and S440W.

In one embodiment of the invention the first Fc region comprises a substitution selected from the group consisting of: E430G and E345K, preferably E430G.

In one embodiment of the invention the second Fc region comprises a substitution selected from the group consisting of: E430G and E345K, preferably E430G.

In one embodiment of the invention the first Fc region comprises an E430G substitution.

In one embodiment of the invention the second Fc region comprises an E430G substitution.

In one embodiment of the invention the first Fc region and second Fc region comprisea substitution selected from the group consisting of: E430G and E345K, preferably E430G.

In one embodiment of the invention the first Fc region and second Fc region comprise an E430G substitution. In one embodiment of the invention the first Fc region and second Fc region comprise an E430S substitution. In one embodiment of the invention the first Fc region and second Fc region comprise an E430F substitution. In one embodiment of the invention the first Fc region and second Fc region comprise an E430T substitution. In one embodiment of the invention the first Fc region and second Fc region comprise an E345K substitution. In one embodiment of the invention the first Fc region and second Fc region comprise an E345R substitution. In one embodiment of the invention the first Fc region and second Fc region comprise an E345Q substitution. In one embodiment of the invention the first Fc region and second Fc region comprise an E345Y substitution. In one embodiment of the invention the first Fc region and second Fc region comprise an S440Y substitution. In one embodiment of the invention the first Fc region and second Fc region comprise an S440W substitution.

In one embodiment of the invention the first antibody comprises a first antigen-binding region capable of binding to human CD37 and a first Fc-region of a human IgG and a second antibody comprises a second antigen-binding region capable of binding to human CD20 and a second Fc-region of a human IgG, wherein the first Fc region comprises an E430G substitution. Thus, in one embodiment the first antibody may have an Fc region which has an Fc-Fc interaction enhancing substitution and the second antibody does not have an Fc-Fc interaction enhancing substitution according to the present invention.

In a preferred embodiment of the invention the first antibody comprises a first antigen-binding region capable of binding to human CD37 and a first Fc-region of a human IgG and the second antibody comprises a second antigen-binding region capable of binding to human CD20 and a second Fc-region of a human IgG, wherein the first and the second Fc region comprises an E430G substitution.

In one embodiment of the invention the composition comprises a first and a second antibody, wherein the first and the second Fc region comprise a further substitution. Examples of such further substitutions may be S440K and/or K439E. Antibodies comprising an Fc-Fc interaction enhancing substitution and a further S440K substitution do not form oligomers with antibodies comprising a S440K substitution. Antibodies comprising an Fc-Fc interaction enhancing substitution and a further K439E substitution do not form oligomers with antibodies comprising a K439E substitution. However, antibodies comprising an Fc-Fc interaction enhancing substitution and a further K439E substitution do form oligomers with antibodies comprising a further S440K substitution. Thus, a first antibody comprising an Fc-Fc interaction enhancing substitution and a further K439E substitution and a second antibody comprising S440K substitution may form hetero-oligomers, such as hetero-hexamers, on the cell surface of a cell expressing the corresponding antigens for both the first and the second antibody.

In one embodiment of the invention the first Fc region further comprises a K439E substitution and the second Fc region further comprises an S440K substitution, with the proviso that the second Fc region does not comprise an S440Y or S440W substitution. Alternatively, in one embodiment the first Fc region further comprises an S440K substitution, with the proviso that the first Fc region does not comprise an S440Y or S440W substitution and the second Fc region further comprises a K439E substitution.

In one embodiment of the invention the first Fc region comprises a substitution of an amino acid at a position corresponding to E430 and a further K439E substitution and a second Fc region comprises a substitution of an amino acid at a position corresponding to E430 and a further S440K substitution.

In one embodiment of the invention the first Fc region comprises a substitution of an amino acid at a position corresponding to E430 and a further S440K substitution and a second Fc region comprises a substitution of an amino acid at a position corresponding to E430 and a further K439E substitution.

In one embodiment of the invention the first Fc region comprises an E430G substitution and a further K439E substitution and the second Fc region comprises an E430G substitution and a further S440K substitution.

In one embodiment of the invention the first Fc region comprises an E430G substitution and a further S440K substitution and the second Fc region comprises an E430G substitution and a further K439E substitution.

In one embodiment of the invention the first Fc region comprises a substitution of an amino acid at a position corresponding to E345 and a further K439E substitution and the second Fc region comprises a substitution of an amino acid at a position corresponding to E345 and a further S440K substitution.

In one embodiment of the invention the first Fc region comprises a substitution of an amino acid at a position corresponding to E345 and a further S440K substitution and the second Fc region comprises a substitution of an amino acid at a position corresponding to E345 and a further K439E substitution.

In one embodiment of the invention the first Fc region comprises an E345K substitution and a further K439E substitution and a second Fc region comprises an E345K substitution and a further S440K substitution.

In one embodiment of the invention the first Fc region comprises an E345K substitution and a further S440K substitution and the second Fc region comprises an E345K substitution and a further K439E substitution.

In one embodiment of the invention the first antigen-binding region is capable of binding to human CD37 having the sequences set forth in SEQ ID No: 1.

In one embodiment of the invention the first antigen-binding region is capable of binding to cynomolgus monkey (*Macaca fascicularis*) CD37 having the sequences set forth in SEQ ID No:1.

In one embodiment of the invention the first antigen-binding region is capable of binding to human CD37 having the sequences set forth in SEQ ID No 1 and to cynomolgus monkey (*Macaca fascicularis*) CD37 having the sequences set forth in SEQ ID No 2. Thus, in one embodiment of the invention the composition comprises a first antibody comprising a first antigen-binding region which is cross-specific for human CD37 and cynomolgus monkey CD37. Antibodies which are cross-specific for human CD37 and cynomolgus monkey CD37 may be preferred for pharmaceutical development, since such antibodies are suitable for preclinical toxicology testing in the cynomolgus monkey.

In one embodiment of the invention the first antibody comprises a first antigen-binding region which has a functional epitope comprising the amino acids Y182, D189, T191, I192, D194, K195, V196, I197 and P199 of SEQ ID No: 1.

In one embodiment of the invention the first antibody comprises a first antigen-binding region which has a functional epitope comprising the amino acids E124, F162, Q163, V164, L165 and H175 of SEQ ID No: 1.

In one embodiment of the invention the composition comprises a first antibody comprising a first antigen-binding region capable of binding to human CD37, wherein the first antibody competes for binding to human CD37 with an anti-CD37 antibody comprising the variable heavy chain (VH) sequence and variable light chain (VL) as set forth in SEQ ID No: 49 and SEQ ID No: 50 respectively.

In one embodiment of the invention the composition comprises a first antibody comprising a first antigen-binding region binding to human CD37, wherein the first antibody competes for binding to human CD37 with an anti-CD37 antibody comprising the variable heavy chain (VH) sequence and variable light chain (VL) sequence as set forth in SEQ ID No: 51 and SEQ ID No: 52 respectively.

In one embodiment of the invention the composition comprises a first antibody comprising a first antigen-binding region binding to human CD37, wherein the first antibody competes for binding to human CD37 with an anti-CD37 antibody comprising the variable heavy chain (VH) sequence and variable light chain (VL) sequence as set forth in SEQ ID No: 53 and SEQ ID No: 54 respectively.

In one embodiment of the invention the composition comprises a first antibody comprising a first antigen-binding region binding to human CD37, wherein the first antibody competes for binding to human CD37 with an anti-CD37 antibody comprising the variable heavy chain (VH) sequence and variable light chain (VL) as set forth in SEQ ID No: 55 and SEQ ID No: 56 respectively.

In one embodiment of the invention the composition comprises a first antibody comprising a first antigen-binding region binding to human CD37, wherein the first antibody competes for binding to human CD37 with an anti-CD37 antibody comprising the variable heavy chain (VH) sequence and variable light chain (VL) as set forth in SEQ ID No: 55 and SEQ ID No: 57 respectively.

In one embodiment of the invention the composition comprises a first antibody comprising a first antigen-binding region binding to human CD37, wherein the first antibody competes for binding to human CD37 with an anti-CD37 antibody comprising the variable heavy chain (VH) sequence and variable light chain (VL) as set forth in SEQ ID No: 7 and SEQ ID No: 11 respectively.

In one embodiment of the invention the composition comprises a first antibody comprising a first antigen-binding region binding to human CD37, wherein the first antibody competes for binding to human CD37 with an anti-CD37 antibody comprising the variable heavy chain (VH) sequence and variable light chain (VL) as set forth in SEQ ID No 14 and SEQ ID No 18 respectively.

In one embodiment of the invention the first antigen-binding region capable of binding to human CD37 comprises a variable heavy chain (VH), comprising three CDR sequences HCDR1, HCDR2 and HCDR3 selected from the group consisting of:
   a. SEQ ID No: 22, 23, 24, respectively [004],
   b. SEQ ID No:29, 30, 31, respectively [005],
   c. SEQ ID No:36, 37, 38, respectively [010],
   d. SEQ ID No:43, 44, 45, respectively [016],
   e. SEQ ID No: 8, 9, 10, respectively and
   f. SEQ ID No:15, 16, 17, respectively.

In one embodiment of the invention the first antigen-binding region capable of binding to human CD37 comprises a variable heavy chain (VH), comprising three CDR sequences HCDR1, HCDR2 and HCDR3 as set forth in SEQ ID No: 22, 23, 24, respectively In one embodiment of the invention the first antigen-binding region capable of binding to human CD37 comprises a variable heavy chain (VH), comprising three CDR sequences HCDR1, HCDR2 and HCDR3 as set forth in SEQ ID No: 29, 30, 31, respectively In one embodiment of the invention the first antigen-binding region capable of binding to human CD37 comprises a variable heavy chain (VH), comprising three CDR sequences HCDR1, HCDR2 and HCDR3 as set forth in SEQ ID No: 36, 37, 38, respectively In one embodiment of the invention the first antigen-binding region capable of binding to human CD37 comprises a variable heavy chain (VH), comprising three CDR sequences HCDR1, HCDR2 and HCDR3 as set forth in SEQ ID No: 43, 44, 45, respectively In one embodiment of the invention the first antigen-binding region capable of binding to human CD37 comprises a variable heavy chain (VH), comprising three CDR sequences HCDR1, HCDR2 and HCDR3 as set forth in SEQ ID No: 8, 9, 10, respectively.

In one embodiment of the invention the first antigen-binding region capable of binding to human CD37 comprises a variable heavy chain (VH), comprising three CDR sequences HCDR1, HCDR2 and HCDR3 as set forth in SEQ ID No: 15, 16, 17, respectively. In one embodiment of the invention the first antigen-binding region capable of binding to human CD37 comprises a variable light chain (VL), comprising three CDR sequences LCDR1, LCDR2 and LCDR3 selected from the group consisting of:
  a. SEQ ID No: 26, EAS, 27, respectively [004],
  b. SEQ ID No: 33, AAS, 34, respectively [005],
  c. SEQ ID No: 40, KAS, 41, respectively [010],
  d. SEQ ID No: 47, YAS, 48, respectively [016],
  e. SEQ ID No: 47, YAS, 58, respectively [016-C90S],
  f. SEQ ID No: 12, VAT, 13, respectively [37.3], and
  g. SEQ ID No: 19, FAK, 20, respectively.

In one embodiment of the invention the first antigen-binding region capable of binding to human CD37 comprises a variable light chain (VL), comprising three CDR sequences LCDR1, LCDR2 and LCDR3 as set forth in SEQ ID No: 26, EAS, 27, respectively [004].

In one embodiment of the invention the first antigen-binding region capable of binding to human CD37 comprises a variable light chain (VL), comprising three CDR sequences LCDR1, LCDR2 and LCDR3 as set forth in SEQ ID No: 33, AAS, 34, respectively [005].

In one embodiment of the invention the first antigen-binding region capable of binding to human CD37 comprises a variable light chain (VL), comprising three CDR sequences LCDR1, LCDR2 and LCDR3 as set forth in SEQ ID No: 40, KAS, 41, respectively [010].

In one embodiment of the invention the first antigen-binding region capable of binding to human CD37 comprises a variable light chain (VL), comprising three CDR sequences LCDR1, LCDR2 and LCDR3 as set forth in SEQ ID No: 47, YAS, 48, respectively [016].

In one embodiment of the invention the first antigen-binding region capable of binding to human CD37 comprises a variable light chain (VL), comprising three CDR sequences LCDR1, LCDR2 and LCDR3 as set forth in SEQ ID No: 47, YAS, 58, respectively [016-C90S].

In one embodiment of the invention the first antigen-binding region capable of binding to human CD37 comprises a variable light chain (VL), comprising three CDR sequences LCDR1, LCDR2 and LCDR3 as set forth in SEQ ID No: 12, VAT, 13, respectively.

In one embodiment of the invention the first antigen-binding region capable of binding to human CD37 comprises a variable light chain (VL), comprising three CDR sequences LCDR1, LCDR2 and LCDR3 as set forth in SEQ ID No: 19, FAK, 20, respectively.

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and
  g. SEQ ID No: 15, 16, 17, 19, FAK, 20 respectively.

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 22, 23, 24, 26, EAS, 27, respectively [004].

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 29, 30, 31, 33, AAS, 34 respectively [005].

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 36, 37, 38, 40, KAS, 41respectively [010].

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 43, 44, 45, 47, YAS, 48 respectively [016].

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 43, 44, 45, 47, YAS, 58 respectively [016-C90S].

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 8, 9, 10, 12, VAT, 13 respectively.

In one embodiment of the invention the first antigen-binding region capable of binding to human CD37 comprises a VH comprising three CDR sequences HCDR1, HCDR2 and HCDR3 and a VL comprising three CDR sequences LCDR1, LCDR2 and LCDR3 as set forth in SEQ ID No: 15, 16, 17, 19, FAK, 20 respectively.

In one embodiment of the invention the first antibody comprises a first Fc region and a first antigen-binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and
  g. SEQ ID No: 15, 16, 17, 19, FAK, 20, respectively, and wherein the first Fc region comprises a substitution of an amino acid at a position corresponding to E430.

In one embodiment of the invention the first antibody comprises a first Fc region and a first antigen-binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and g. SEQ ID No: 15, 16, 17, 19, FAK, 20, respectively, and wherein the first Fc region comprises an E430G substitution.

In one embodiment of the invention the first antibody comprises a first Fc region and a first antigen-binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
 a. SEQ ID No: 22, 23, 24, 26, EAS, 27, respectively [004],
 b. SEQ ID No: 29, 30, 31, 33, AAS, 34 respectively [005],
 c. SEQ ID No: 36, 37, 38, 40, KAS, 41, respectively [010],
 d. SEQ ID No: 43, 44, 45, 47, YAS, 48 respectively [016],
 e. SEQ ID No: 43, 44, 45, 47, YAS, 58 respectively [016-C90S],
 f. SEQ ID No: 8, 9, 10, 12, VAT, 13 respectively, and
 g. SEQ ID No: 15, 16, 17, 19, FAK, 20, respectively and wherein the first Fc region comprises a substitution of an amino acid at a position corresponding to E345.

In one embodiment of the invention the first antibody comprises a first Fc region and a first antigen-binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
 a. SEQ ID No: 22, 23, 24, 26, EAS, 27, respectively [004],
 b. SEQ ID No: 29, 30, 31, 33, AAS, 34 respectively [005],
 c. SEQ ID No: 36, 37, 38, 40, KAS, 41, respectively [010],
 d. SEQ ID No: 43, 44, 45, 47, YAS, 48 respectively [016],
 e. SEQ ID No: 43, 44, 45, 47, YAS, 58 respectively [016-C90S],
 f. SEQ ID No: 8, 9, 10, 12, VAT, 13 respectively, and
 g. SEQ ID No: 15, 16, 17, 19, FAK, 20, respectively and wherein the first Fc region comprises an E345K substitution.

In one embodiment of the invention the first antibody comprises a first Fc region and a first antigen-binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
 a. SEQ ID No: 22, 23, 24, 26, EAS, 27, respectively [004],
 b. SEQ ID No: 29, 30, 31, 33, AAS, 34 respectively [005],
 c. SEQ ID No: 36, 37, 38, 40, KAS, 41, respectively [010],
 d. SEQ ID No: 43, 44, 45, 47, YAS, 48 respectively [016],
 e. SEQ ID No: 43, 44, 45, 47, YAS, 58 respectively [016-C90S],
 f. SEQ ID No: 8, 9, 10, 12, VAT, 13 respectively, and
 g. SEQ ID No: 15, 16, 17, 19, FAK, 20, respectively and wherein the first Fc region comprises an E345R substitution.

In one embodiment of the invention the first antibody comprises a first Fc region and a first antigen-binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
 a. SEQ ID No: 22, 23, 24, 26, EAS, 27, respectively [004],
 b. SEQ ID No: 29, 30, 31, 33, AAS, 34 respectively [005],
 c. SEQ ID No: 36, 37, 38, 40, KAS, 41, respectively [010],
 d. SEQ ID No: 43, 44, 45, 47, YAS, 48 respectively [016],
 e. SEQ ID No: 43, 44, 45, 47, YAS, 58 respectively [016-C90S],
 f. SEQ ID No: 8, 9, 10, 12, VAT, 13 respectively, and
 g. SEQ ID No: 15, 16, 17, 19, FAK, 20, respectively and wherein the first Fc region comprises an S440Y or S440W substitution.

In one embodiment of the invention the first antibody comprises a first antigen-binding region capable of binding to human CD37 comprising a VH and VL having sequences selected from the group consisting of:
 a. VH SEQ ID No: 49, and VL SEQ ID No: 50, respectively [004],
 b. VH SEQ ID No: 51, and VL SEQ ID No: 52, respectively [005]
 c. VH SEQ ID No. 53, and VL SEQ ID No: 54, respectively [010],
 d. VH SEQ ID No: 55, and VL SEQ ID No: 56, respectively [016],
 e. VH SEQ ID No: 55, and VL SEQ ID No: 57, respectively [016-C90S],
 f. VH SEQ ID No: 7, and VL SEQ ID No:11, respectively,
 g. VH SEQ ID No: 14, and VL SEQ ID No: 18, respectively, and
 h. a VH and VL sequence having at least 90%, at least 95%, at least 97 or at least 99% amino acid sequence identity to any one of the sequences as set forth in a) to g).

In one embodiment of the invention the first antibody comprises a first antigen-binding region capable of binding to human CD37 comprising a VH and VL having sequences selected from the group consisting of:
 a. VH SEQ ID No: 49, and VL SEQ ID No: 50, respectively [004],
 b. VH SEQ ID No: 51, and VL SEQ ID No: 52, respectively [005]
 c. VH SEQ ID No: 53, and VL SEQ ID No: 54, respectively [010],
 d. VH SEQ ID No: 55, and VL SEQ ID No: 56, respectively [016],
 e. VH SEQ ID No: 55, and VL SEQ ID No: 57, respectively [016-C90S],
 f. VH SEQ ID No: 7, and VL SEQ ID No: 11, respectively,
 g. VH SEQ ID No: 14, and VL SEQ ID No: 18, respectively, and
 h. a VH and VL sequence having at most 10 amino acid substitutions in the frame work sequence, such as 9 amino acid substitutions, such as 8 amino acid substitutions, such as 7 amino acid substitutions, such as 6 amino acid substitutions, such as 5 amino acid substitutions, such as 4 amino acid substitutions, such as 3 amino acid substitutions, such as 2 amino acid substitutions, such as 1 amino acid substitution in any one of the sequences as set forth in a) to g).

In one embodiment of the invention the composition comprises a first antibody comprising a first antigen-binding region capable of binding to human CD37 comprising a VH and VL having the sequences set forth in SEQ ID No: 51 and SEQ ID No: 52 respectively.

In one embodiment of the invention the composition comprises a first antibody comprising a first antigen-binding region capable of binding to human CD37 comprising a VH and VL having the sequences set forth in SEQ ID No: 53 and SEQ ID No: 54 respectively.

In one embodiment of the invention the composition comprises a first antibody comprising a first antigen-binding region capable of binding to human CD37 comprising a VH and VL having the sequences set forth in SEQ ID No: 55 and SEQ ID No: 56 respectively.

In one embodiment of the invention the composition comprises a first antibody comprising a first antigen-binding region capable of binding to human CD37 comprising a VH and VL having the sequences set forth in SEQ ID No: 55 and SEQ ID No: 57 respectively.

In one embodiment of the invention the composition comprises a first antibody comprising a first antigen-binding region capable of binding to human CD37 comprising a VH and VL having the sequences set forth in SEQ ID No: 7 and SEQ ID No: 11 respectively.

In one embodiment of the invention the composition comprises a first antibody comprising a first antigen-binding region capable of binding to human CD37 comprising a VH and VL having the sequences set forth in SEQ ID No: 14 and SEQ ID No: 18 respectively.

In one embodiment of the invention the composition comprises a first antibody comprising a first antigen-binding region capable of binding to human CD37 comprising a VH and VL having the sequences set forth in SEQ ID No: 49 and SEQ ID No: 50 respectively.

In one embodiment of the invention the first antibody comprises a first Fc region and a first antigen-binding region capable of binding to human CD37 comprising a VH and VL having sequences selected from the group consisting of:
  a. VH SEQ ID No: 49, and VL SEQ ID No: 50, respectively [004],
  b. VH SEQ ID No: 51, and VL SEQ ID No: 52, respectively [005],
  c. VH SEQ ID No: 53, and VL SEQ ID No: 54, respectively [010],
  d. VH SEQ ID No: 55, and VL SEQ ID No: 56, respectively [016],
  e. VH SEQ ID No: 55, and VL SEQ ID No: 57, respectively [016-C90S],
  f. VH SEQ ID No: 7, and VL SEQ ID No: 11, respectively, and
  g. VH SEQ ID No: 14, and VL SEQ ID No: 18, respectively, and wherein the first Fc region comprises a substitution of an amino acid at a position corresponding to E430.

In one embodiment of the invention the first antibody comprises a first Fc region and a first antigen-binding region capable of binding to human CD37 comprising a VH and VL having sequences selected from the group consisting of:
  a. VH SEQ ID No: 49, and VL SEQ ID No: 50, respectively [004],
  b. VH SEQ ID No: 51, and VL SEQ ID No: 52, respectively [005],
  c. VH SEQ ID No: 53, and VL SEQ ID No: 54, respectively [010],
  d. VH SEQ ID No: 55, and VL SEQ ID No: 56, respectively [016],
  e. VH SEQ ID No: 55, and VL SEQ ID No: 57, respectively [016-C90S],
  f. VH SEQ ID No: 7, and VL SEQ ID No: 11, respectively, and
  g. VH SEQ ID No: 14, and VL SEQ ID No: 18, respectively, and wherein the first Fc region comprises an E430G substitution.

In one embodiment of the invention the first antibody comprises a first Fc region and a first antigen-binding region binding to human CD37 comprising a VH and VL having sequences selected from the group consisting of:
  a. VH SEQ ID No: 49, and VL SEQ ID No: 50, respectively [004],
  b. VH SEQ ID No: 51, and VL SEQ ID No: 52, respectively [005]
  c. VH SEQ ID No: 53, and VL SEQ ID No: 54, respectively [010],
  d. VH SEQ ID No: 55, and VL SEQ ID No: 56, respectively [016],
  e. VH SEQ ID No: 55, and VL SEQ ID No: 57, respectively [016-C90S],
  f. VH SEQ ID No: 7, and VL SEQ ID No: 11, respectively, and
  g. VH SEQ ID No: 14, and VL SEQ ID No: 18, respectively, and wherein the first Fc region comprises a substitution of an amino acid at a position corresponding to E345.

In one embodiment of the invention the first antibody comprises a first Fc region and a first antigen-binding region capable of binding to human CD37 comprising a VH and VL having sequences selected from the group consisting of:
  a. VH SEQ ID No: 49, and VL SEQ ID No: 50, respectively [004],
  b. VH SEQ ID No: 51, and VL SEQ ID No: 52, respectively [005]
  c. VH SEQ ID No: 53, and VL SEQ ID No: 54, respectively [010],
  d. VH SEQ ID No: 55, and VL SEQ ID No: 56, respectively [016],
  e. VH SEQ ID No: 55, and VL SEQ ID No: 57, respectively [016-C90S],
  f. VH SEQ ID No: 7, and VL SEQ ID No: 11, respectively, and
  g. VH SEQ ID No: 14, and VL SEQ ID No: 18, respectively, and wherein the first Fc region comprises an E345K or E345R substitution.

In one embodiment of the invention the first antibody comprises a first Fc region and a first antigen-binding region capable of binding to human CD37 comprising a VH and VL having sequences selected from the group consisting of:
  a. VH SEQ ID No: 49, and VL SEQ ID No: 50, respectively [004],
  b. VH SEQ ID No: 51, and VL SEQ ID No: 52, respectively [005],
  c. VH SEQ ID No: 53, and VL SEQ ID No: 54, respectively [010],
  d. VH SEQ ID No: 55, and VL SEQ ID No: 56, respectively [016],
  e. VH SEQ ID No: 55, and VL SEQ ID No: 57, respectively [016-C90S],
  f. VH SEQ ID No: 7, and VL SEQ ID No: 11, respectively, and
  g. VH SEQ ID No: 14, and VL SEQ ID No: 18, respectively, and wherein the first Fc region comprises a S440Y or S440W substitution.

CD20 Embodiments

In one embodiment of the invention the second antigen-binding region is capable of binding to human CD20 having the sequences set forth in SEQ ID No: 5.

In one embodiment of the invention the second antigen-binding region is capable of binding to cynomolgus monkey CD20 having the sequences set forth in SEQ ID No: 6.

In one embodiment of the invention the second antigen-binding region is capable of binding to human and cynomolgus monkey CD20 having the sequences set forth in SEQ ID Nos: 5 and 6, respectively.

In one embodiment of the invention the second antigen-binding region capable of binding to human CD20 binds to an epitope on human CD20, which does not comprise or require the amino acid residues alanine at position 170 or proline at position 172, but which comprises or requires the amino acid residues asparagine at position 163 and asparagine at position 166 of SEQ ID No. 5. Examples of such antibodies are the antibodies denoted 2F2 and 7D8 as disclosed in WO2004035607 (Genmab) and the antibody denoted 2C6 as disclosed in WO2005103081 (Genmab). The CDR sequences of 7D8 are disclosed in Table 1.

In one embodiment of the invention the second antigen-binding region capable of binding to human CD20 binds to an epitope on human CD20, which does not comprise or require the amino acid residues alanine at position 170 or proline at position 172 of SEQ ID No. 5. An example of such an antibody is 11B8 as disclosed in WO2004035607 (Genmab). The CDR sequences of 11B8 are disclosed in Table 1.

In one embodiment of the invention the second antigen-binding region capable of binding to human CD20 binds to a discontinuous epitope on CD20, wherein the epitope comprises part of the first small extracellular loop and part of the second extracellular loop.

In one embodiment of the invention the second antigen-binding region capable of binding to human CD20 binds to a discontinuous epitope on CD20, wherein the epitope has residues AGIYAP of the small first extracellular loop and residues MESLNFIRAHTPYI of the second extracellular loop.

Anti-CD20 antibodies may characterize as type I and type II anti-CD20 antibodies. Type I anti-CD20 antibodies, have high CDC and ADCC activity, but low apoptosis activity, such as ofatumumab, 7D8 and rituximab, whereas type II anti-CD20 antibodies, having low or no CDC activity, but high ADCC and apoptosis activity, such as obinutuzumab and 11B8.

In one embodiment of the invention the composition comprises a second antibody comprising a second antigen-binding region capable of binding to human CD20, wherein the second antibody competes for binding to human CD20 with an anti-CD20 antibody comprising the variable heavy chain (VH) sequence and variable light chain (VL) as set forth in SEQ ID No 59 and SEQ ID No 63 respectively.

In one embodiment of the invention the composition comprises a second antibody comprising a second antigen-binding region capable of binding to human CD20, wherein the second antibody competes for binding to human CD20 with an anti-CD20 antibody comprising the variable heavy chain (VH) sequence and variable light chain (VL) as set forth in SEQ ID No 66 and SEQ ID No 70 respectively.

In one embodiment of the invention the composition comprises a second antibody comprising a second antigen-binding region capable of binding to human CD20, wherein the second antibody competes for binding to human CD20 with an anti-CD20 antibody comprising the variable heavy chain (VH) sequence and variable light chain (VL) as set forth in SEQ ID No 72 and SEQ ID No 63 respectively.

In one embodiment of the invention the composition comprises a second antibody comprising a second antigen-binding region capable of binding to human CD20, wherein the second antibody competes for binding to human CD20 with an anti-CD20 antibody comprising the variable heavy chain (VH) sequence and variable light chain (VL) as set forth in SEQ ID No 75 and SEQ ID No 79 respectively.

In one embodiment of the invention the second antigen-binding region capable of binding to human CD20 comprises a VH comprising three CDR sequences HCDR1, HCDR2 and HCDR3 selected from the group consisting of:
 a. SEQ ID No: 60, 61, 62, respectively [7D8],
 b. SEQ ID No: 67, 68, 69, respectively [11B8],
 c. SEQ ID No: 73, 74, 62, respectively [Ofatumumab],
 d. SEQ ID No: 76, 77, 78, respectively [Rituximab], and
 e. SEQ ID No: 83, 84, 85, respectively [obinutuzumab].

In one embodiment of the invention the second antigen-binding region capable of binding to human CD20 comprises a VL comprising three CDR sequences LCDR1, LCDR2 and LCDR3 selected from the group consisting of:
 f. SEQ ID No: 64, DAS, 65, respectively [7D8]/[Ofatumumab],
 g. SEQ ID No: 64, DAS, 71, respectively [11B8],
 h. SEQ ID No: 80, ATS, 81, respectively [Rituximab],
 i. SEQ ID No: 87, QMS, 88, respectively [obinutuzumab].

In one embodiment of the invention the second antigen-binding region capable of binding to human CD20 comprises a VH comprising three CDR sequences HCDR1, HCDR2 and HCDR3 and a VL comprising three CDR sequences LCDR1, LCDR2 and LCDR3 selected from the group consisting of:
 a. SEQ ID No: 60, 61, 62,64, DAS, 65, respectively [7D8],
 b. SEQ ID No: 67, 68, 69, 64, DAS, 71, respectively [11B8],
 c. SEQ ID No: 73, 74, 62, 64, DAS, 65, respectively [Ofatumumab],
 d. SEQ ID No: 76, 77, 78, 80, ATS, 81, respectively [Rituximab], and
 e. SEQ ID No: 83, 84, 85, 87, QMS, 88 respectively.

In one embodiment of the invention the second antigen-binding region capable of binding to human CD20 comprises a VH comprising three CDR sequences HCDR1, HCDR2 and HCDR3 and a VL comprising three CDR sequences LCDR1, LCDR2 and LCDR3 as set forth in SEQ ID No: 60, 61, 62, 64, DAS, 65, respectively [7D8].

In one embodiment of the invention the second antigen-binding region capable of binding to human CD20 comprises a VH comprising three CDR sequences HCDR1, HCDR2 and HCDR3 and a VL comprising three CDR sequences LCDR1, LCDR2 and LCDR3 as set forth in SEQ ID No: 67, 68, 69, 64, DAS, 71, respectively [11B8].

In one embodiment of the invention the second antigen-binding region capable of binding to human CD20 comprises a VH comprising three CDR sequences HCDR1, HCDR2 and HCDR3 and a VL comprising three CDR sequences LCDR1, LCDR2 and LCDR3 as set forth in 73, 74, 62, 64, DAS, 65, respectively In one embodiment of the invention the second antigen-binding region capable of binding to human CD20 comprises a VH comprising three CDR sequences HCDR1, HCDR2 and HCDR3 and a VL comprising three CDR sequences LCDR1, LCDR2 and LCDR3 as set forth in 76, 77, 78, 80, ATS, 81, respectively In one embodiment of the invention the second antigen-binding region capable of binding to human CD20 comprises a VH comprising three CDR sequences HCDR1, HCDR2 and HCDR3 and a VL comprising three CDR sequences LCDR1, LCDR2 and LCDR3 as set forth in SEQ ID No: 83, 84, 85, 87, QMS, 88, respectively.

In one embodiment of the invention the second antibody comprises a second Fc region and a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
 a. SEQ ID No: 60, 61, 62,64, DAS, 65, respectively [7D8],
 b. SEQ ID No: 67, 68, 69, 64, DAS, 71, respectively [11B8], c. SEQ ID No: 73, 74, 62, 64, DAS, 65, respectively [Ofatumumab],
d. SEQ ID No: 76, 77, 78, 80, ATS, 81, respectively [Rituximab], and
e. SEQ ID No: 83, 84, 85, 87, QMS, 88 respectively, wherein the second Fc region comprises a substitution of an amino acid at a position corresponding to E430.

In one embodiment of the invention the second antibody comprises second Fc region and a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
a. SEQ ID No: 60, 61, 62,64, DAS, 65, respectively [7D8],
b. SEQ ID No: 67, 68, 69, 64, DAS, 71, respectively [1168],
c. SEQ ID No: 73, 74, 62, 64, DAS, 65, respectively [Ofatumumab],
d. SEQ ID No: 76, 77, 78, 80, ATS, 81, respectively [Rituximab], and
e. SEQ ID No: 83, 84, 85, 87, QMS, 88 respectively, wherein the second Fc region comprises an E430G substitution.

In one embodiment of the invention the second antibody comprises second Fc region and a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
a. SEQ ID No: 60, 61, 62,64, DAS, 65, respectively [7D8],
b. SEQ ID No: 67, 68, 69, 64, DAS, 71, respectively [1168],
c. SEQ ID No: 73, 74, 62, 64, DAS, 65, respectively [Ofatumumab],
d. SEQ ID No: 76, 77, 78, 80, ATS, 81, respectively [Rituximab], and
e. SEQ ID No: 83, 84, 85, 87, QMS, 88 respectively,
f. and wherein the second Fc region comprises a substitution of an amino acid at a position corresponding to E345.

In one embodiment of the invention the second antibody comprises second Fc region and a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
a. SEQ ID No: 60, 61, 62,64, DAS, 65, respectively [7D8],
b. SEQ ID No: 67, 68, 69, 64, DAS, 71, respectively [11B8],
c. SEQ ID No: 73, 74, 62, 64, DAS, 65, respectively [Ofatumumab],
d. SEQ ID No: 76, 77, 78, 80, ATS, 81, respectively [Rituximab], and
e. SEQ ID No: 83, 84, 85, 87, QMS, 88 respectively, wherein the second Fc region comprises an E345K substitution.

In one embodiment of the invention the second antibody comprises second Fc region and a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
a. SEQ ID No: 60, 61, 62,64, DAS, 65, respectively [7D8],
b. SEQ ID No: 67, 68, 69, 64, DAS, 71, respectively [11B8],
c. SEQ ID No: 73, 74, 62, 64, DAS, 65, respectively [Ofatumumab],
d. SEQ ID No: 76, 77, 78, 80, ATS, 81, respectively [Rituximab], and
e. SEQ ID No: 83, 84, 85, 87, QMS, 88 respectively, and wherein the second Fc region comprises an E345R substitution.

In one embodiment of the invention the second antibody comprises second Fc region and a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
a. SEQ ID No: 60, 61, 62,64, DAS, 65, respectively [7D8],
b. SEQ ID No: 67, 68, 69, 64, DAS, 71, respectively [11B8],
c. SEQ ID No: 73, 74, 62, 64, DAS, 65, respectively [Ofatumumab],
d. SEQ ID No: 76, 77, 78, 80, ATS, 81, respectively [Rituximab], and
e. SEQ ID No: 83, 84, 85, 87, QMS, 88 respectively, and wherein the second Fc region comprises an S440Y or S440W substitution.

In one embodiment of the invention the composition comprises a second antibody comprising second antigen-binding region capable of binding to human CD20 comprising a VH and VL, having sequences selected from the group consisting of:
a. VH SEQ ID No: 59, and VL SEQ ID No: 63 [7D8],
b. VH SEQ ID No: 66, and VL SEQ ID No: 70 [1188],
c. VH SEQ ID No: 72, and VL SEQ ID No: 63 [Ofatumumab]
d. VH SEQ ID No: 75, and VL SEQ ID No: 79 [Rituximab],
e. VH SEQ ID No: 83, and VL SEQ ID No: 87 and
f. a VH and VL sequence having at least 90%, at least 95%, at least 97 or at least 99% amino acid sequence identity to any one of the sequences as set forth in a) to e).

In one embodiment of the invention the composition comprises a second antibody comprising second antigen-binding region capable of binding to human CD20 comprising a VH and VL having sequences selected from the group consisting of:
a. VH SEQ ID No: 59, and VL SEQ ID No: 63 [7D8],
b. VH SEQ ID No: 66, and VL SEQ ID No: 70 [1188],
c. VH SEQ ID No: 72, and VL SEQ ID No: 63 [Ofatumumab
d. VH SEQ ID No: 7, and VL SEQ ID No: 79 [Rituximab],
e. VH SEQ ID No: 82, and VL SEQ ID No: 86
f. a VH and VL sequence having at most 10 amino acid substitutions in the frame work sequence, such as 9 amino acid substitutions, such as 8 amino acid substitutions, such as 7 amino acid substitutions, such as 6 amino acid substitutions, such as 5 amino acid substitutions, such as 4 amino acid substitutions, such as 3 amino acid substitutions, such as 2 amino acid substitutions, such as 1 amino acid substitution in any one of the sequences as set forth in a) to e).

In one embodiment of the invention the composition comprises a second antibody comprising second antigen-binding region capable of binding to human CD20 comprising a VH and VL having the sequences set forth in SEQ ID No 59 and SEQ ID No 63 respectively.

In one embodiment of the invention the composition comprises a second antibody comprising second antigen-binding region capable of binding to human CD20 comprising a VH and VL having the sequences set forth in SEQ ID No 66 and SEQ ID No 70 respectively.

In one embodiment of the invention the composition comprises a second antibody comprising second antigen-binding region capable of binding to human CD20 comprising a VH and VL having the sequences set forth in SEQ ID No 72 and SEQ ID No 63 respectively.

In one embodiment of the invention the composition comprises a second antibody comprising second antigen-binding region capable of binding to human CD20 comprising a VH and VL having the sequences set forth in SEQ ID No 75 and SEQ ID No 79 respectively.

In one embodiment of the invention the composition comprises a second antibody comprising second antigen-binding region capable of binding to human CD20 comprising a VH and VL having the sequences set forth in SEQ ID No 82 and SEQ ID No 86 respectively.

In one embodiment of the invention the composition comprises a first antibody comprising a first antigen binding region capable of binding to human CD37 comprising a VH comprising the three CDR sequences HCDR1, HCDR2 and HCDR3 and a VL comprising the three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and SEQ ID No: 15, 16, 17, 19, FAK, 20, respectively and
a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
  g. SEQ ID No: 60, 61, 62, 64, DAS, 65, respectively [7D8],
  h. SEQ ID No: 67, 68, 69, 64, DAS, 71, respectively [11B8],
  i. SEQ ID No: 73, 74, 62, 64, DAS, 65, respectively [Ofatumumab],
  j. SEQ ID No: 76, 77, 78, 80, ATS, 81, respectively [Rituximab], and
  k. SEQ ID No: 83, 84, 85, 87, QMS, 88 respectively.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and SEQ ID No: 15, 16, 17, 19, FAK, 20, respectively and
a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
  g. SEQ ID No: 60, 61, 62, 64, DAS, 65, respectively [7D8],
  h. SEQ ID No: 67, 68, 69, 64, DAS, 71, respectively [1168],
  i. SEQ ID No: 73, 74, 62, 64, DAS, 65, respectively [Ofatumumab],
  j. SEQ ID No: 76, 77, 78, 80, ATS, 81, respectively [Rituximab], and
  k. SEQ ID No: 83, 84, 85, 87, QMS, 88 respectively. wherein the first and second Fc region comprises a substitution of an amino acid at a position corresponding to E430.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005],
  c. SEQ ID No: 36, 37, 38, 40, KAS, 41, respectively [010],
  d. SEQ ID No: 43, 44, 45, 47, YAS, 48 respectively [016],
  e. SEQ ID No: 43, 44, 45, 47, YAS, 58 respectively [016-C90S],
  f. SEQ ID No: 8, 9, 10, 12, VAT, 13 respectively, and SEQ ID No: 15, 16, 17, 19, FAK, 20, respectively and
a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:
  g. SEQ ID No: 60, 61, 62, 64, DAS, 65, respectively [7D8],
  h. SEQ ID No: 67, 68, 69, 64, DAS, 71, respectively [11B8],
  i. SEQ ID No: 73, 74, 62, 64, DAS, 65, respectively [Ofatumumab],
  j. SEQ ID No: 76, 77, 78, 80, ATS, 81, respectively [Rituximab], and
  k. SEQ ID No: 83, 84, 85, 87, QMS, 88 respectively. wherein the first and second Fc region comprises an E430G substitution.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:
  a. SEQ ID No: 22, 23, 24, 26, EAS, 27, respectively [004],
  b. SEQ ID No: 29, 30, 31, 33, AAS, 34 respectively [005], c. SEQ ID No: 36, 37, 38, 40, KAS, 41, respectively [010],
d. SEQ ID No: 43, 44, 45, 47, YAS, 48 respectively [016],
e. SEQ ID No: 43, 44, 45, 47, YAS, 58 respectively [016-C90S],
f. SEQ ID No: 8, 9, 10, 12, VAT, 13 respectively, and SEQ ID No: 15, 16, 17, 19, FAK, 20, respectively and a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:

g. SEQ ID No: 60, 61, 62,64, DAS, 65, respectively [7D8],
h. SEQ ID No: 67, 68, 69, 64, DAS, 71, respectively [11B8],
i. SEQ ID No: 73, 74, 62, 64, DAS, 65, respectively [Ofatumumab],
j. SEQ ID No: 76, 77, 78, 80, ATS, 81, respectively [Rituximab], and k. SEQ ID No: 83, 84, 85, 87, QMS, 88 respectively. wherein the first and second Fc region comprises a substitution of an amino acid at a position corresponding to E345.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:

a. SEQ ID No: 22, 23, 24, 26, EAS, 27, respectively [004],
b. SEQ ID No: 29, 30, 31, 33, AAS, 34 respectively [005],
c. SEQ ID No: 36, 37, 38, 40, KAS, 41, respectively [010],
d. SEQ ID No: 43, 44, 45, 47, YAS, 48 respectively [016],
e. SEQ ID No: 43, 44, 45, 47, YAS, 58 respectively [016-C90S],
f. SEQ ID No: 8, 9, 10, 12, VAT, 13 respectively, and SEQ ID No: 15, 16, 17, 19, FAK, 20, respectively and a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:

g. SEQ ID No: 60, 61, 62,64, DAS, 65, respectively [7D8],
h. SEQ ID No: 67, 68, 69, 64, DAS, 71, respectively [11B8],
i. SEQ ID No: 73, 74, 62, 64, DAS, 65, respectively [Ofatumumab],
j. SEQ ID No: 76, 77, 78, 80, ATS, 81, respectively [Rituximab], and
k. SEQ ID No: 83, 84, 85, 87, QMS, 88 respectively. wherein the first and second Fc region comprises an E345K substitution.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:

a. SEQ ID No: 22, 23, 24, 26, EAS, 27, respectively [004],
b. SEQ ID No: 29, 30, 31, 33, AAS, 34 respectively [005], c. SEQ ID No: 36, 37, 38, 40, KAS, 41, respectively [010],
d. SEQ ID No: 43, 44, 45, 47, YAS, 48 respectively [016],
e. SEQ ID No: 43, 44, 45, 47, YAS, 58 respectively [016-C90S],
f. SEQ ID No: 8, 9, 10, 12, VAT, 13 respectively, and SEQ ID No: 15, 16, 17, 19, FAK, 20, respectively and a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:

g. SEQ ID No: 60, 61, 62,64, DAS, 65, respectively [7D8],
h. SEQ ID No: 67, 68, 69, 64, DAS, 71, respectively [11B8],
i. SEQ ID No: 73, 74, 62, 64, DAS, 65, respectively [Ofatumumab],
j. SEQ ID No: 76, 77, 78, 80, ATS, 81, respectively [Rituximab], and
k. SEQ ID No: 83, 84, 85, 87, QMS, 88 respectively, and wherein the first and second Fc region comprises an E345R substitution.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of:

a. SEQ ID No: 22, 23, 24, 26, EAS, 27, respectively [004],
b. SEQ ID No: 29, 30, 31, 33, AAS, 34 respectively [005],
c. SEQ ID No: 36, 37, 38, 40, KAS, 41, respectively [010],
d. SEQ ID No: 43, 44, 45, 47, YAS, 48 respectively [016],
e. SEQ ID No: 43, 44, 45, 47, YAS, 58 respectively [016-C90S],
f. SEQ ID No: 8, 9, 10, 12, VAT, 13 respectively, and
g. SEQ ID No: 15, 16, 17, 19, FAK, 20, respectively, and a second antibody comprising a second antigen-binding region capable of binding to human CD20 comprising a VH comprising three CDR sequences HCDR1, HCDR2 and HCDR3 and a VL comprising three CDR sequences LCDR1, LCDR2 and LCDR3 selected from the group consisting of:

h. SEQ ID No: 60, 61, 62,64, DAS, 65, respectively [7D8],
i. SEQ ID No: 67, 68, 69, 64, DAS, 71, respectively [1B8],
j. SEQ ID No: 73, 74, 62, 64, DAS, 65, respectively [Ofatumumab],
k. SEQ ID No: 76, 77, 78, 80, ATS, 81, respectively [Rituximab], and
l. SEQ ID No: 83, 84, 85, 87, QMS, 88 respectively, and wherein the first and second Fc region comprises an S440Y or S440W substitution.

In one embodiment of the invention the composition comprises a first antibody comprising a first Fc region and a first antigen binding region capable of binding to human CD37 comprising a VH comprising three CDR sequences HCDR1, HCDR2 and HCDR3 and a VL comprising three CDR sequences LCDR1, LCDR2 and LCDR3 selected from the group consisting of a. VH SEQ ID No: 49, and VL SEQ ID No 50, respectively [004], b. VH SEQ ID No 51, and VL SEQ ID No 52, respectively [005],
c. VH SEQ ID No 53, and VL SEQ ID No 54, respectively [010],
d. VH SEQ ID No 55, and VL SEQ ID No 56, respectively [016],
e. VH SEQ ID No 55, and VL SEQ ID No 57, respectively [016-C90S],
f. VH SEQ ID No 7, and VL SEQ ID No 11, respectively, and
g. VH SEQ ID No 14, and VL SEQ ID No 18, respectively.

In one embodiment of the invention the composition comprises a first antibody comprising a first antigen binding region capable of binding to human CD37 comprising VH and VL sequences selected from the group consisting of:
a. VH SEQ ID No: 49, and VL SEQ ID No 50, respectively [004],
b. VH SEQ ID No 51, and VL SEQ ID No 52, respectively [005],
c. VH SEQ ID No 53, and VL SEQ ID No 54, respectively [010],
d. VH SEQ ID No 55, and VL SEQ ID No 56, respectively [016],
e. VH SEQ ID No 55, and VL SEQ ID No 57, respectively [016-C90S],
f. VH SEQ ID No 7, and VL SEQ ID No 11, respectively, and
g. VH SEQ ID No 14, and VL SEQ ID No 18, respectively, and a second antibody comprising a second antigen-binding region capable of binding to human CD20 comprising VH and VL sequences selected form the group consisting of:
h. VH SEQ ID No: 59, and VL SEQ ID No: 63 [7D8],
i. VH SEQ ID No: 66, and VL SEQ ID No: 70 [11B8],
j. VH SEQ ID No: 72, and VL SEQ ID No: 63 [Ofatumumab]
k. VH SEQ ID No: 75, and VL SEQ ID No: 79 [Rituximab],
l. VH SEQ ID No: 82, and VL SEQ ID No: 86 [Obinutuzumab].

In one embodiment of the invention the composition comprises a first antibody comprising a first Fc region and a first antigen binding region capable of binding to human CD37 comprising VH and VL sequences selected from the group consisting of:
a. VH SEQ ID No: 49, and VL SEQ ID No 50, respectively [004],
b. VH SEQ ID No 51, and VL SEQ ID No 52, respectively [005],
c. VH SEQ ID No 53, and VL SEQ ID No 54, respectively [010],
d. VH SEQ ID No 55, and VL SEQ ID No 56, respectively [016],
e. VH SEQ ID No 55, and VL SEQ ID No 57, respectively [016-C90S],
f. VH SEQ ID No 7, and VL SEQ ID No 11, respectively, and
g. VH SEQ ID No 14, and VL SEQ ID No 18, respectively and a second antibody comprising a second antigen-binding region capable of binding to human CD20 comprising VH and VL sequences selected form the group consisting of:
h. VH SEQ ID No: 59, and VL SEQ ID No: 63 [7D8],
i. VH SEQ ID No: 66, and VL SEQ ID No: 70 [11B8],
j. VH SEQ ID No: 72, and VL SEQ ID No: 63 [Ofatumumab]
k. VH SEQ ID No: 75, and VL SEQ ID No: 79 [Rituximab],
l. VH SEQ ID No: 82, and VL SEQ ID No: 86 [Obinutuzumab] and wherein the first and second Fc region comprises a substitution of an amino acid at a position corresponding to E430.

In one embodiment of the invention the composition comprises a first antibody comprising a first Fc region and a first antigen binding region capable of binding to human CD37 comprising VH and VL sequences selected from the group consisting of:
a. VH SEQ ID No: 49, and VL SEQ ID No 50, respectively [004],
b. VH SEQ ID No 51, and VL SEQ ID No 52, respectively [005],
c. VH SEQ ID No 53, and VL SEQ ID No 54, respectively [010],
d. VH SEQ ID No 55, and VL SEQ ID No 56, respectively [016],
e. VH SEQ ID No 55, and VL SEQ ID No 57, respectively [016-C90S],
f. VH SEQ ID No 7, and VL SEQ ID No 11, respectively, and
g. VH SEQ ID No 14, and VL SEQ ID No 18, respectively and a second antibody comprising a second antigen-binding region capable of binding to human CD20 comprising VH and VL sequences selected form the group consisting of:
h. VH SEQ ID No: 59, and VL SEQ ID No: 63 [7D8],
i. VH SEQ ID No: 66, and VL SEQ ID No: 70 [11B8],
j. VH SEQ ID No: 72, and VL SEQ ID No: 63 [Ofatumumab]
k. VH SEQ ID No: 75, and VL SEQ ID No: 79 [Rituximab],
lp l. VH SEQ ID No: 82, and VL SEQ ID No: 86 [Obinutuzumab] and wherein a first and second Fc region comprises an E430G substitution.

In one embodiment of the invention the composition comprises a first antibody comprising a first Fc region and a first antigen binding region capable of binding to human CD37 comprising VH and VL sequences selected from the group consisting of:
a. VH SEQ ID No: 49, and VL SEQ ID No 50, respectively [004],
b. VH SEQ ID No 51, and VL SEQ ID No 52, respectively [005],
c. VH SEQ ID No 53, and VL SEQ ID No 54, respectively [010],
d. VH SEQ ID No 55, and VL SEQ ID No 56, respectively [016],
e. VH SEQ ID No 55, and VL SEQ ID No 57, respectively [016-C90S],
f. VH SEQ ID No 7, and VL SEQ ID No 11, respectively, and
g. VH SEQ ID No 14, and VL SEQ ID No 18, respectively and a second antibody comprising a second antigen-binding region capable of binding to human CD20 comprising VH and VL sequences selected form the group consisting of:
h. VH SEQ ID No: 59, and VL SEQ ID No: 63 [7D8],
i. VH SEQ ID No: 66, and VL SEQ ID No: 70 [11B8],
j. VH SEQ ID No: 72, and VL SEQ ID No: 63 [Ofatumumab]
k. VH SEQ ID No: 75, and VL SEQ ID No: 79 [Rituximab], l. VH SEQ ID No: 82, and VL SEQ ID No: 86 [Obinutuzumab] and wherein a first and second Fc region comprises a substitution of an amino acid at a position corresponding to E345.

In one embodiment of the invention the composition comprises a first antibody comprising a first Fc region and a first antigen binding region capable of binding to human CD37 comprising VH and VL sequences selected from the group consisting of:
 a. VH SEQ ID No: 49, and VL SEQ ID No 50, respectively [004],
 b. VH SEQ ID No 51, and VL SEQ ID No 52, respectively [005],
 c. VH SEQ ID No 53, and VL SEQ ID No 54, respectively [010],
 d. VH SEQ ID No 55, and VL SEQ ID No 56, respectively [016],
 e. VH SEQ ID No 55, and VL SEQ ID No 57, respectively [016-C90S],
 f. VH SEQ ID No 7, and VL SEQ ID No 11, respectively, and
 g. VH SEQ ID No 14, and VL SEQ ID No 18, respectively and a second antibody comprising a second antigen-binding region capable of binding to human CD20 comprising VH and VL sequences selected form the group consisting of:
 h. VH SEQ ID No: 59, and VL SEQ ID No: 63 [7D8],
 i. VH SEQ ID No: 66, and VL SEQ ID No: 70 [11B8],
 j. VH SEQ ID No: 72, and VL SEQ ID No: 63 [Ofatumumab]
 k. VH SEQ ID No: 75, and VL SEQ ID No: 79 [Rituximab],
 l. VH SEQ ID No: 82, and VL SEQ ID No: 86 [Obinutuzumab] and wherein a first and second Fc region comprises an E345K substitution.

In one embodiment of the invention the composition comprises a first antibody comprising a first Fc region and a first antigen binding region capable of binding to human CD37 comprising VH and VL sequences selected from the group consisting of:
 a. VH SEQ ID No: 49, and VL SEQ ID No 50, respectively [004],
 b. VH SEQ ID No 51, and VL SEQ ID No 52, respectively [005],
 c. VH SEQ ID No 53, and VL SEQ ID No 54, respectively [010],
 d. VH SEQ ID No 55, and VL SEQ ID No 56, respectively [016],
 e. VH SEQ ID No 55, and VL SEQ ID No 57, respectively [016-C90S],
 f. VH SEQ ID No 7, and VL SEQ ID No 11, respectively, and
 g. VH SEQ ID No 14, and VL SEQ ID No 18, respectively and a second antibody comprising a second antigen-binding region capable of binding to human CD20 comprising VH and VL sequences selected form the group consisting of:
 h. VH SEQ ID No: 59, and VL SEQ ID No: 63 [7D8],
 i. VH SEQ ID No: 66, and VL SEQ ID No: 70 [11B8],
 j. VH SEQ ID No: 72, and VL SEQ ID No: 63 [Ofatumumab
 k. VH SEQ ID No: 75, and VL SEQ ID No: 79 [Rituximab],
 l. VH SEQ ID No: 82, and VL SEQ ID No: 86 [Obinutuzumab] and wherein a first and second Fc region comprises an E345R substitution.

In one embodiment of the invention the composition comprises a first antibody comprising a first Fc region and a first antigen binding region capable of binding to human CD37 comprising VH and VL sequences selected from the group consisting of:
 a. VH SEQ ID No: 49, and VL SEQ ID No 50, respectively [004],
 b. VH SEQ ID No 51, and VL SEQ ID No 52, respectively [005],
 c. VH SEQ ID No 53, and VL SEQ ID No 54, respectively [010],
 d. VH SEQ ID No 55, and VL SEQ ID No 56, respectively [016],
 e. VH SEQ ID No 55, and VL SEQ ID No 57, respectively [016-C90S],
 f. VH SEQ ID No 7, and VL SEQ ID No 11, respectively, and
 g. VH SEQ ID No 14, and VL SEQ ID No 18, respectively and a second antibody comprising a second antigen-binding region capable of binding to human CD20 comprising VH and VL sequences selected form the group consisting of:
 h. VH SEQ ID No: 59, and VL SEQ ID No: 63 [7D8],
 i. VH SEQ ID No: 66, and VL SEQ ID No: 70 [1188],
 j. VH SEQ ID No: 72, and VL SEQ ID No: 63 [Ofatumumab]
 k. VH SEQ ID No: 75, and VL SEQ ID No: 79 [Rituximab],
 l. VH SEQ ID No: 82, and VL SEQ ID No: 85 [Obinutuzumab] and wherein a first and second Fc region comprises an S440Y or S440W substitution.

In one embodiment of the invention the composition comprises a first and/or second antibody which is a human, humanized or chimeric antibody.

In one embodiment of the invention the composition comprises a first antibody which is humanized and a second antibody which is human.

In one embodiment of the invention the composition comprises a first and/or second antibody which is a monoclonal antibody.

In one embodiment of the invention the composition comprises a first antibody which is a monoclonal antibody. In one embodiment of the invention the composition comprises a second antibody which is a monoclonal antibody.

In one embodiment of the invention the composition comprises a first antibody and/or a second antibody which is bivalent antibody.

In one embodiment of the invention the composition comprises a first and/or second antibody, which is a human IgG isotype.

In one embodiment of the invention the composition comprises a first and/or second antibody which is a human IgG1, IgG2, IgG3 or IgG4 isotype.

In one embodiment of the invention the composition comprises a first and/or second antibody which is an IgG1 isotype.

In on embodiment of the invention the composition comprises a first and/or second antibody which is a full-length antibody.

In one embodiment of the invention the composition comprises a first and/or second antibody which is an IgG1m (f), IgG1m(a), IgG1m(z), IgG1m(x) allotype or mixed allotype.

In one embodiment of the invention a first antibody and a second antibody are present in the composition at a 1:50 to 50:1 molar ratio, such as about a 1:1 molar ratio, about a 1:2 molar ratio, about a 1:3 molar ratio, about a 1:4 molar ratio, about a 1:5 molar ratio, about a 1:6 molar ratio, about a 1:7 molar ratio, about a 1:8 molar ratio, about a 1:9 molar ratio, about a 1:10 molar ratio, about a 1:15 molar ratio, about a 1:20 molar ratio, about a 1:25 molar ratio, about a 1:30 molar ratio, about a 1:35 molar ratio, about a 1:40 molar ratio, about a 1:45 molar ratio, about a 1:50 molar ratio, about a 50:1 molar ratio, about a 45:1 molar ratio, about a 40:1 molar ratio, about a 35:1 molar ratio, about a 30:1 molar ratio, about a 25:1 molar ratio, about a 20:1 molar ratio, about a 15:1 molar ratio, about a 10:1 molar ratio, about a 9:1 molar ratio, about a 8:1 molar ratio, about a 7:1 molar ratio, about a 6:1 molar ratio, about a 5:1 molar ratio, about a 4:1 molar ratio, about a 3:1 molar ratio, about a 2:1 molar ratio.

In one embodiment of the invention the pharmaceutical composition comprises a first and a second antibody, wherein said first antibody and said second antibody are present in the composition at about a 1:50 to 50:1 molar ratio, about a 1:45 to 45:1 molar ratio, about a 1:40 to 40:1 molar ratio, about a 1:35 to 35:1 molar ratio, about a 1:30 to 30:1 molar ratio, about a 1:25 to 25:1 molar ratio, about a 1:20 to 20:1 molar ratio, about a 1:15 to 15:1 molar ratio, about a 1:10 to 10:1 molar ratio, or about a 1:5 to 5:1 molar ratio.

In one embodiment of the invention the pharmaceutical composition comprises a first and a second antibody, wherein said first antibody and said second antibody are present in the composition at a 1:9 to 9:1 molar ratio.

In one embodiment of the invention the pharmaceutical composition comprises a first and a second antibody, wherein said first antibody and said second antibody are present in the composition at about a 1:9 to 9:1 molar ratio.

In one embodiment of the invention the pharmaceutical composition comprises a first and a second antibody, wherein said first antibody and said second antibody are present in the composition at about a 1:4 to 4:1 molar ratio, such as about a 1:3 to 3:1 molar ratio, such as about a 1:2 to 2:1 molar ratio.

In one embodiment of the invention the pharmaceutical composition comprises a first and a second antibody, wherein said first antibody and said second antibody are present in the composition at approximately a 1:1 molar ratio.

In one embodiment of the invention a first antibody and a second antibody are present in the composition at a molar ratio of 1:1.

In one embodiment of the invention a first antibody and a second antibody are present in the composition at an equimolar ratio.

In one embodiment of the invention a first antibody and a second antibody and an additional antibody/or polypeptide are present in the composition at an equimolar ratio.

In one embodiment of the invention the composition further comprises a pharmaceutical carrier or excipient.

In one embodiment of the present invention the composition according to any aspect or embodiment is a pharmaceutical composition.

Pharmaceutical compositions of the present invention may comprise antibodies such as monoclonal antibodies according to any aspect or embodiment of the present invention.

The pharmaceutical compositions may be formulated with pharmaceutically acceptable carriers or diluents as well as any other known adjuvants and excipients in accordance with conventional techniques such as those disclosed in (Rowe et al., Handbook of Pharmaceutical Excipients, 2012 June, ISBN 9780857110275).

The pharmaceutically acceptable carriers or diluents as well as any other known adjuvants and excipients should be suitable for the antibody of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.) upon antigen binding).

A pharmaceutical composition of the present invention may also include diluents, fillers, salts, buffers, detergents (e.g., a nonionic detergent, such as Tween-20 or Tween-80), stabilizers (e.g., sugars or protein-free amino acids), preservatives, tissue fixatives, solubilizers, and/or other materials suitable for inclusion in a pharmaceutical composition.

The actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. Suitable routes of administering a compound of the present invention in vivo and in vitro are well known in the art and may be selected by those of ordinary skill in the art.

In one embodiment, the pharmaceutical composition of the present invention is administered parenterally.

The terms "parenteral administration" and "administered parenterally" as used herein refers to modes of administration other than enteral and topical administration, usually by injection, and include epidermal, intravenous, intramuscular, intra-arterial, intrathecal, intracapsular, intra-orbital, intracardiac, intradermal, intraperitoneal, intratendinous, transtracheal, subcutaneous, subcuticular, intra-articular, subcapsular, subarachnoid, intraspinal, intracranial, intrathoracic, epidural and intrasternal injection and infusion.

In one embodiment, the pharmaceutical composition of the present invention is administered by intravenous or subcutaneous injection or infusion.

In one embodiment of the present invention the pharmaceutical composition comprises a first and a second antibody according to the invention such as monoclonal antibodies together with a pharmaceutical carrier.

Pharmaceutically acceptable carriers include any and all suitable solvents, dispersion media, coatings, antibacterial and antifungal agents, isotonicity agents, antioxidants and absorption-delaying agents, and the like that are physiologically compatible with a compound of the present invention.

Examples of suitable aqueous and non-aqueous carriers which may be employed in the pharmaceutical compositions of the present invention include water, saline, phosphate-buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and micro-encapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, poly-ortho-esters, and polylactic acid alone or with a wax, or other materials well known in the art. Methods for the preparation of such formulations are generally known to those skilled in the art.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Other active or therapeutic compounds may also be incorporated into the compositions.

Pharmaceutical compositions for injection or infusion must typically be sterile and stable under the conditions of manufacture and storage. The composition may be formulated as a solution, micro-emulsion, liposome, or other ordered structure suitable to high drug concentration. The carrier may be an aqueous or a non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum-drying and freeze-drying (lyophilization) that yield a powder of the active ingredient plus any additional desired ingredient from a previously sterile-filtered solution thereof.

The pharmaceutical composition of the present invention may contain one or more monoclonal antibodies or one or more bispecific antibodies of the present invention, a combination of an antibody or a bispecific antibody according to the invention with another therapeutic compound, or a combination of compounds of the present invention.

Therapeutic Applications

The compositions according to any aspect or embodiment of the present invention may be uses as a medicament, i.e. for therapeutic applications.

In one embodiment the invention relates to the composition for use as a medicament.

In one embodiment the invention relates to the composition for use in treatment of cancer, autoimmune disease or inflammatory disorders.

In one embodiment the invention relates to the composition for use in treatment of allergy.

In one embodiment the invention relates to the composition for use in treatment of transplant rejection.

In one embodiment the invention relates to the composition for use in treatment of a B-cell malignancy.

In one embodiment the invention relates to the composition for use in treatment of solid tumors and/or hematological tumors.

In a preferred embodiment the invention relates to the composition for use in treatment of hematological tumors.

In one embodiment the invention relates to the composition for use in treatment of hematological tumors such as, leukemia, chronic lymphocytic leukemia, myeloid leukemia, acute myeloid leukemia, chronic myeloid leukemia, lymphoma, Non-Hodgkin lymphoma or multiple myeloma, Hodgkin Lymphoma or myelodysplastic syndromes.

In one embodiment the invention relates to the composition for use in treatment of follicular lymphoma, mantel cell lymphoma, plasma cell leukemia, diffuse large B-cell lymphoma, or acute lymphoblastic leukemia.

In one embodiment the invention relates to the composition for use in treatment of rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylids) systemic lupus erythematosus (SLE) such as cutaneous SLE or subacute cutaneous SLE, neonatal lupus syndrome (NLE), and lupus erythematosis disseminates, multiple sclerosis, inflammatory bowel disease (IBD) which includes ulcerative colitis and Crohn's disease, Chronic obstructive pulmonary disease (COPD), psoriasis, IgA nephropathy, IgM polyneuropathies, myasthenia gravis, diabetes mellitus, Reynaud's syndrome, and glomerulonephritis, pustulosis palmoplantaris (PPP), erosive lichen planus, pemphigus bullosa, epidermolysis bullosa, contact dermatitis and atopic dermatitis, polyradiculitis including Guillain-Barre syndrome.

In another aspect the invention relates to use of the composition for the manufacture of a medicament.

In one embodiment the invention relates to the use of the composition for the manufacture of a medicament for treatment of solid tumors and/or hematological tumors.

In one embodiment the invention relates to the use of the composition in combination with a further therapeutic treatment, including but not limited to chemotherapy, radiation, immunotherapy, targeted therapy, stem cell transplantation or surgery.

In one embodiment the invention relates to the use of the composition in combination with a chemotherapeutic agent, including but not limited to alkylating agents (including but not limited to cyclophosphamide, chlorambucil, bendamustine, ifosfamide, cisplatin, carboplatin, oxaliplatin, carmustine), corticosteroids (including but not limited to prednisone, dexamethasone), purine analogs (including but not limited to fludarabine, pentostatin, cladribine), pyrimidine analogs (including but not limited to fluorouracil, gemcitabine), other anti-metabolites (including but not limited to cytarabine, methotrexate, pralatrexate, fludarabine, gemcitabine), microtubule inhibitors (including but not limited to vincristine, paclitaxel, docetaxel), topoisomerase inhibitors (including but not limited to doxorubicin, mitoxantrone, etoposide, topotecan, irinotecan), other anti-tumor antibiotics (including but not limited to bleomycin).

In one embodiment the invention relates to the use of the composition in combination with an immunotherapeutic agent, including but not limited to monoclonal antibodies (including but not limited to CD52-specific alemtuzumab, CD30-specific brentuximab, JNJ-63709178, JNJ-64007957, HuMax-IL8, anti-DR5, anti-VEGF, anti-CD38, anti-PD-1, anti-PD-L1, anti-CTLA4, anti-CD40, anti-CD137, anti-GITR, anti-VISTA or antibodies specific for other immunomodulatory targets), antibody-drug conjugates (including but not limited to brentuximab vedotin, HuMax-TAC-ADC), Interferon, immunomodulating drugs (including but not limited to thalidomide, lenalidomide), chimeric antigen receptor (CAR) T-cell therapy (including but not limited to Axicabtagene ciloleucel).

In one embodiment the invention relates to the use of the composition in combination with targeted therapy, including but not limited to proteasome inhibitors (including but not limited to bortezomib), Histone deacetylase (HDAC) inhibitors (including but not limited to romidepsin, belinostat, vorinostat), kinase inhibitors (including but not limited to Bruton's tyrosine kinase (BTK) inhibitors such as ibrutinib or acalabrutinib; PI3K inhibitors such as idelalisib or copanlisib;, tyrosine kinase inhibitors such as sorafenib, sunitinib, everolimus, apoptosis-modulating agents (including but not limited to recombinant human TRAIL or SMAC mimetic birinapant or venetoclax).

In one embodiment the invention relates to the use of the composition in combination with a further therapeutic agent.

In one embodiment of the invention the further therapeutic agent is a chemotherapeutic agent.

In one embodiment the invention relates to the use of the composition in combination with a further therapeutic agent selected from the group comprising: anthracyclines, alkylating agents, corticosteroids, anti-metabolites, microtubule inhibitors, topoisomerase inhibitors, anti-tumor antibiotics, monoclonal antibodies, antibody mimetics, antibody-drug conjugates (ADC), Interferon, immunomodulating drugs, Chimeric antigen receptor (CAR) T-cell therapeutic agents, kinase inhibitors, proteasome inhibitors, histon deacetylase (HDAC) inhibitors, apoptosis-modulating agents.

In one embodiment of the invention the further therapeutic agent is selected from the group comprising: cyclophosphamide, chlorambucil, bendamustine, ifosfamide, cisplatin, carboplatin, oxaliplatin, carmustine, prednisone, dexamethasone, fludarabine, pentostatin, cladribine, fluorouracil, gemcitabine, cytarabine, methotrexate, pralatrexate, gemcitabine, vincristine, paclitaxel, docetaxel, doxorubicin, mitoxantrone, etoposide, topotecan, irinotecan, bleomycin, CD52-specific alemtuzumab, CD30-specific brentuximab, JNJ-63709178, JNJ-64007957, HuMax-IL8, anti-DR5, anti-VEGF, anti-CD38, anti-PD-1, anti-PD-L1, anti-CTLA4, anti-CD40, anti-CD137, anti-GITR, anti-VISTA, antibodies specific for other immunomodulatory targets, brentuximab vedotin, HuMax-TAC-ADC, Interferon, thalidomide, lenalidomide, Axicabtagene ciloleucel, bortezomib, romidepsin, belinostat, vorinostat, ibrutinib, acalabrutinib, idelalisib, copanlisib, sorafenib, sunitinib, everolimus, recombinant human TRAIL, birinapant, and venetoclax).

In one embodiment of the invention the further therapeutic agent is selected from the group comprising: doxorubicin, cisplatin, bleomycin, carmustine, cyclophosphamide, chlorambucil, bendamustine, vincristine, fludarabine, ibrutinib and venetoclax.

In another aspect the invention relates to a method of inducing cell death, or inhibiting growth and/or proliferation of a tumor expressing CD37 and CD20 comprising administering to an individual in need thereof a composition according to any aspect or embodiment disclosed herein.

In one embodiment the invention relates to a method of treating an individual having a solid tumor and/or hematological tumor, comprising administering to said individual an effective amount of the composition according to any aspect or embodiment disclosed herein.

In one embodiment of the invention the method relates to administering a further therapeutic agent in combination with a composition according to any aspect or embodiment disclosed herein.

In one embodiment of the invention the method relates to administering a further therapeutic agent is selected from the group consisting of: doxorubicin, cisplatin, bleomycin, carmustine, cyclophosphamide, chlorambucil, bendamustine, vincristine, fludarabine,ibrutinib and venetoclax.

Further Embodiments of the Invention

In a further aspect, the invention comprises a kit of parts comprising a first antibody and a second antibody, wherein said first antibody and said second antibody is in one or more separate containers such as one or more vials.

In one embodiment of the invention the kit of parts comprises a first anti-CD37 antibody and a second anti-CD20 antibody according to the invention is for simultaneous, separate or sequential use in therapy.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

In another aspect of the present invention, the invention comprises a nucleic acid construct encoding an antibody according to amino acid sequences set forth in table 1. That is in one embodiment, the present invention comprises, a nucleic acid construct encoding an antibody corresponding to the amino acid sequences set forth in SEQ ID Nos: 7 to 58 or 59 to 89. In one embodiment of the present invention, the nucleic acid construct encodes an antibody according to any embodiments disclosed herein.

In a further aspect, the present invention relates to a nucleic acid encoding an antibody according to the present invention, wherein the Fc region comprises a mutation of an amino acids position corresponding to E430, E345 or S440 in a human IgG1, EU numbering. It is further contemplated that the nucleic acid encoding an antibody according to the invention comprises the amino acid substitutions in the specific amino acid positions herein described. Thus, in one embodiment, the nucleic acid encodes an antibody having the sequence according to SEQ ID NO: 101, 102, 103, 104 or 105.

In another aspect, the invention relates to nucleic acids encoding a sequence of a human, humanized or chimeric anti-CD37 antibody for use in the invention, to expression vectors encoding the sequences of such an antibody, to host cells comprising such expression vectors, to hybridomas which produce such antibodies, and to methods of producing such an antibody by culturing such host cells or hybridomas under appropriate conditions whereby the antibody is produced and, optionally, retrieved. Humanized anti-CD37 antibodies may also be denoted as "huCD37".

In one embodiment, the invention provides an expression vector comprising a nucleotide sequence encoding one or more of the amino acid sequence according to SEQ ID NOs: 7 to 108 In another embodiment, the expression vector comprises a nucleotide sequence encoding a VH amino acid sequence selected from SEQ ID NOs: 7, 14, 21, 28, 35, 42, 49, 51, 53 and 55. In another embodiment, the expression vector comprises a nucleotide sequence encoding a VL amino acid sequence selected from SEQ ID NOs: 11, 18, 25, 32, 39, 46, 50, 52, 54, 56 and 57. In another embodiment, the expression vector comprises a nucleotide sequence encoding the constant region of a human antibody light chain, of a human antibody heavy chain, or both. In another embodiment, the expression vector comprising a nucleotide sequence encoding the constant region of a human antibody heavy chain selected from the group consisting of: SEQ ID NOs: 96, 97, 98, 99, 100, 101, 102, 103, 104, 105, 106 and 107.

In one embodiment of the invention, the expression vector comprising a nucleotide sequence encoding the constant region of a human antibody heavy chain selected from the group consisting of: SEQ ID NOs: 100, 101, 102, 103 and 104. In a preferred embodiment of the invention, the expression vector comprising a nucleotide sequence encoding the constant region of a human antibody heavy chain selected from the group consisting of: SEQ ID NOs: 100, 101 and 102.

In a particular embodiment, the expression vector comprises a nucleotide sequence encoding a variant of one or more of the above amino acid sequences, said variant having at most 25 amino acid modifications, such as at most 20, such as at most 15, 14, 13, 12, or 11 amino acid modifications, such as 10, 9, 8, 7, 6, 5, 4, 3, 2, or 1 amino acid modifications, such as deletions or insertions, preferably substitutions, such as conservative substitutions, or at least 80% identity to any of said sequences, such as at least 85% identity or 90% identity or 95% identity, such as 96% identity or 97% identity or 98% identity or 99% identity to any of the afore-mentioned amino acid sequences.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a humanized CD37 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a $CaPO_4$-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972). In one embodiment, the vector is suitable for expression of a humanized anti-CD37 antibody or a humanized anti-CD20 antibody, in a bacterial cell. Examples of such vectors include expression vectors such as BlueScript (Stratagene), pIN vectors (Van Heeke & Schuster, J Biol Chem 264, 5503-5509 (1989)), pET vectors (Novagen, Madison WI) and the like.

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art, and include secretion leader or signal peptides, organelle-targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

In an expression vector of the invention, anti-CD37 or anti-CD20 antibody-encoding nucleic acids and the first and the second polypeptides nucleic acids may comprise or be associated with any suitable promoter, enhancer, and other expression-facilitating elements. Examples of such elements include strong expression promoters (e.g., human CMV IE promoter/enhancer as well as RSV, SV40, SL3-3, MMTV, and HIV LTR promoters), effective poly (A) termination sequences, an origin of replication for plasmid product in $E.$ $coli$, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In one embodiment, the anti-CD37 antibody-encoding expression is positioned in and/or delivered to the host cell or host animal via a viral vector. In one embodiment, the anti-CD20 antibody-encoding expression is positioned in and/or delivered to the host cell or host animal via a viral vector.

Such expression vectors may be used for recombinant production of anti-CD37 or anti-CD20 antibodies.

In one aspect, the anti-CD37 or anti-CD20 antibodies of any aspect or embodiment described herein are provided by use of recombinant eukaryotic or prokaryotic host cell which produces the antibody. Accordingly, the invention provides a recombinant eukaryotic or prokaryotic host cell, such as a transfectoma, which produces an anti-CD37 antibody or an ani-CD20 antibody as defined herein. Examples of host cells include yeast, bacterial and mammalian cells, such as CHO or HEK-293 cells. For example, in one embodiment, the host cell comprises a nucleic acid stably integrated into the cellular genome that comprises a sequence coding for expression of an anti-CD37 antibody or an anti-CD20 antibody described herein. In one embodiment, the host cell comprises a nucleic acid stably integrated into the cellular genome that comprise a sequence coding for expression of a first or a second polypeptide described herein. In another embodiment, the host cell comprises a non-integrated nucleic acid, such as a plasmid, cosmid, phagemid, or linear expression element, which comprises a sequence coding for expression of a anti-DR5 antibody, a first or a second polypeptide described herein.

The term "recombinant host cell" (or simply "host cell"), as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK-293 cells, PER.C6, NSO cells, and lymphocytic cells, and prokaryotic cells such as $E.$ $coli$ and other eukaryotic hosts such as plant cells and fungi.

The term "transfectoma", as used herein, includes recombinant eukaryotic host cells expressing the antibody or a target antigen, such as CHO cells, PER.C6, NSO cells, HEK-293 cells, plant cells, or fungi, including yeast cells.

In a further aspect, the invention relates to a method for producing an antibody of the invention, said method comprising the steps of
a) culturing a hybridoma or a host cell of the invention as described herein above, and
b) retrieving and/or purifying the antibody of the invention from the culture media.

In a further aspect, the nucleotide sequence encoding a sequence of an antibody further encodes a second moiety, such as a therapeutic polypeptide. Exemplary therapeutic antibodies are described elsewhere herein. In one embodiment, the invention relates to a method for producing an antibody fusion protein, said method comprising the steps of
a) culturing a host cell comprising an expression vector comprising such a nucleotide sequence, and
b) retrieving and/or purifying the antibody fusion protein from the culture media.

In one aspect of the present invention, the invention comprises an expression vector comprising on or more nucleic acid constructs encoding an antibody according to any embodiment disclosed herein.

In a further aspect of the invention, the invention comprises a host cell comprising an expression vector.

In one embodiment of the invention the host cell is a recombinant host cell, such as a recombinant prokaryotic cell, recombinant eukaryotic cell or recombinant microbial host cell.

Sequences

TABLE 1

| SEQ ID NO: | Name | Sequence |
| --- | --- | --- |
| SEQ ID NO 1 | Human CD37 | MSAQESCLSLIKYFLFVFNLFFFVLGSLIFCFGIWILIDKTSFVSFVGLA FVPLQIWSKVLAISGIFTMGIALLGCVGALKELRCLLGLYFGMLLLLFAT QITLGILISTQRAQLERSLRDVVEKTIQKYGTNPEETAAEESWDYVQF QLRCCGWHYPQDWFQVLILRGNGSEAHRVPCSCYNLSATNDSTILD KVILPQLSRLGHLARSRHSADICAVPAESHIYREGCAQGLQKWLHNN LISIVGICLGVGLLELGFMTLSIFLCRNLDHVYNRLARYR |
| SEQ ID NO 2 | Cynomolgus monkey CD37 (mfCD37) | MSAQESCLSLIKYFLFVFNLFFFVLGSLIFCFGIWILIDKTSFVSFVGLA FVPLQIWSKVLAISGVFTMGLALLGCVGALKELRCLLGLYFGMLLLLFA TQITLGILISTQRAQLERSLQDIVEKTIQKYHTNPEETAAEESWDYVQF QLRCCGWHSPQDWFQVLTLRGNGSEAHRVPCSCYNLSATNDSTILD |

TABLE 1-continued

| SEQ ID NO: | Name | Sequence |
|---|---|---|
| | | KVILPQLSRLGQLARSRHSTDICAVPANSHIYREGCARSLQKWLHNN<br>LISIVGICLGVGLLELGFMTLSIFLCRNLDHVYNRLARYR |
| SEQ ID NO 3 | CD37EC2-<br>FcHis | MWWRLWWLLLLLLLLWPMVWARAQLERSLRDVVEKTIQKYGTNPEE<br>TAAEESWDYVQFQLRCCGWHYPQDWFQVLILRGNGSEAHRVPCSCY<br>NLSATNDSTILDKVILPQLSRLGHLARSRHSADICAVPAESHIYREGC<br>AQGLQKWLHNNPKSCDKTHTCPPCPAPEAEGAPSVFLFPPKPKDTLM<br>ISRTPEVTCVVVDVSHEDPEVKFNWYVDGVEVHNAKTKPREEQYNST<br>YRVVSVLTVLHQDWLNGKEYKCKVSNKALPAPIEKTISKAKGQPREP<br>QVYTLPPSREEMTKNQVSLTCLVKGFYPSDIAVEWESNGQPENNYKT<br>APPVLDSDGSFFLYSKLTVDKSRWQQGNVFSCSVMHEALHNHYTQK<br>SLSLSPGKHHHHHHHH |
| SEQ ID NO 4 | CD37mfEC2-<br>FcHis | MWWRLWWLLLLLLLLWPMVWARAQLERSLQDIVEKTIQKYHTNPEE<br>TAAEESWDYVQFQLRCCGWHSPQDWFQVLTLRGNGSEAHRVPCSCY<br>YNLSATNDSTILDKVILPQLSRLGQLARSRHSTDICAVPANSHIYREG<br>CARSLQKWLHNNPKSCDKTHTCPPCPAPEAEGAPSVFLFPPKPKDTL<br>MISRTPEVTCVVVDVSHEDPEVKFNWYVDGVEVHNAKTKPREEQYN<br>STYRVVSVLTVLHQDWLNGKEYKCKVSNKALPAPIEKTISKAKGQPRE<br>PQVYTLPPSREEMTKNQVSLTCLVKGFYPSDIAVEWESNGQPENNYK<br>TAPPVLDSDGSFFLYSKLTVDKSRWQQGNVFSCSVMHEALHNHYTQ<br>KSLSLSPGKHHHHHHHH |
| SEQ ID NO 5 | Human CD20 | MTTPRNSVNGTFPAEPMKGPIAMQSGPKPLFRRMSSLVGPTQSFFMR<br>ESKTLGAVQIMNGLFHIALGGLLMIPAGIYAPICVTVWYPLWGGIMYII<br>SGSLLAATEKNSRKCLVKGKMIMNSLSLFAAISGMILSIMDILNIKISH<br>FLKMESLNFIRAHTPYINIYNCEPANPSEKNSPSTQYCYSIQSLFLGILS<br>VMLIFAFFQELVIAGIVENEWKRTCSRPKSNIVLLSAEEKKEQTIEIKEE<br>VVGLTETSSQPKNEEDIEIIPIQEEEEEETETNFPEPPQDQESSPIENDS<br>SP |
| SEQ ID NO 6 | Cynomolgus<br>monkey<br>CD20 | MTTPRNSVNGTFPAEPMKGPIAMQPGPKPLLRRMSSLVGPTQSFFMR<br>ESKALGAVQIMNGLFHIALGGLLMIPAGIYAPICVTVWYPLWGGIMYII<br>SGSLLAATEKNSRKCLVKGKMIMNSLSLFAAISGMILSIMDILNIKISH<br>FLKMESLNFIRVHTPYINIYNCEPANPSEKNSPSTQYCYSIQSLFLGILS<br>VMLIFAFFQELVIAGIVENEWRRTCSRPKSSVVLLSAEEKKEQVIEIKE<br>EVVGLTETSSQPKNEEDIEIIPIQEEEEEETETNFPEPPQDQESSPIEND<br>SSP |
| SEQ ID NO 7 | VH CD37-<br>37.3 | QVQVKESGPGLVAPSQSLSITCTVSGFSLTTSGVSWVRQPPGKGLE<br>WLGVIWGDGSTNYHSALKSRLSIKKDHSKSQVFLKLNSLQTDDTAT<br>YYCAKGGYSLAHWGGTLVTVSA |
| SEQ ID NO 8 | VH CD37-<br>37.3 CDR1 | GFSLTTSG |
| SEQ ID NO 9 | VH CD37-<br>37.3 CDR2 | IWGDGST |
| SEQ ID NO 10 | VH CD37-<br>37.3 CDR3 | AKGGYSLAH |
| SEQ ID NO 11 | VL CD37-37.3 | DIQMTQSPASLSVSVGETVTITCRASENIRSNLAWYQQKQGKSPQL<br>LVNVATNLADGVPSRFSGSGSGTQYSLKINSLQSEDFGTYYCQHYW<br>GTTWTFGGGTKLEIK |
| SEQ ID NO 12 | VL CD37-37.3<br>CDR1 | ENIRSN |
| | VL CD37-37.3<br>CDR2 | VAT |
| SEQ ID NO 13 | VL CD37-37.3<br>CDR3 | QHYWGTTWT |
| SEQ ID NO 14 | VH CD37-<br>G28.1 | AVQLQQSGPELEKPGASVKISCKASGYSFTGYNMNWVKQNNGKSL<br>EWIGNIDPYYGGTTYNRKFKGKATLTVDKSSSTAYMQLKSLTSEDS<br>AVYYCARSVGPMDYWGGTSVTVSS |
| SEQ ID NO 15 | VH CD37-<br>G28.1 CDR1 | GYSFTGYN |
| SEQ ID NO 16 | VH CD37-<br>G28.1 CDR2 | IDPYYGGT |
| SEQ ID NO 17 | VH CD37-<br>G28.1 CDR3 | ARSVGPMDY |

TABLE 1-continued

| SEQ ID NO: | Name | Sequence |
|---|---|---|
| SEQ ID NO 18 | VL CD37-G28.1 | DIQMTQSPASLSASVGETVTITCRTSENVYSYLAWYQQKQGKSPQL LVSFAKTLAEGVPSRFSGSGSGTQFSLKISSLQPEDSGSYFCQHHSD NPWTFGGGTELEIK |
| SEQ ID NO 19 | VL CD37-G28.1 CDR1 | ENVYSY |
|  | VL CD37-G28.1 CDR2 | FAK |
| SEQ ID NO 20 | VL CD37-G28.1 CDR3 | QHHSDNPWT |
| SEQ ID NO 21 | VH CD37-004 | QSVEESGGRLVTPGTPLTLTCTVSGFSLSTYDMSWVRQAPGKGLEW IGIIYSSVGAYYASWAKGRFTFSKTSTTVDLKITSPTTEDTATYFCAR EYGASSSDYIFSLWGQGTLVTVSS |
| SEQ ID NO 22 | VH CD37-004 CDR1 | GFSLSTYD |
| SEQ ID NO 23 | VH CD37-004 CDR2 | IYSSVGA |
| SEQ ID NO 24 | VH CD37-004 CDR3 | AREYGASSSDYIFSL |
| SEQ ID NO 25 | VL CD37-004 | AQVLTQTPSPVSAAVGGTVTINCQASQSVYNSQNLAWYQQKPGQP PKLLIYEASKLASGVPSRFKGSGSGTQFTLTISGVQSDDAATYYCQG EFSCISADCTAFGGGTEVVVK |
| SEQ ID NO 26 | VL CD37-004 CDR1 | QSVYNSQN |
|  | VL CD37-004 CDR2 | EAS |
| SEQ ID NO 27 | VL CD37-004 CDR3 | QGEFSCISADCTA |
| SEQ ID NO 28 | VH CD37-005 | QSVEESGGRLVTPGTPLTLTCTVSGFSLSSNAMNWVRQAPGKGLEW IGLIYASGNTDYASWAKGRFTISKTSTTVDLKITSPTTEDTATYFCAR EGSVWGAAFDPWGPGTLVTVSS |
| SEQ ID NO 29 | VH CD37-005 CDR1 | GFSLSSNA |
| SEQ ID NO 30 | VH CD37-005 CDR2 | IYASGNT |
| SEQ ID NO 31 | VH CD37-005 CDR3 | AREGSVWGAAFDP |
| SEQ ID NO 32 | VL CD37-005 | AYDMTQTPASVEVAVGGTVTIKCQASQSISNWLAWYQQKPGQPPK QLIYAASTLASGVPSRFKGSGSGTQFTLTISGVESADAATYYCQQGY SNSNIDNTFGGGTEVVVK |
| SEQ ID NO 33 | VL CD37-005 CDR1 | QSISNW |
|  | VL CD37-005 CDR2 | AAS |
| SEQ ID NO 34 | VL CD37-005 CDR3 | QQGYSNSNIDNT |
| SEQ ID NO 35 | VH CD37-010 CDR1 | QSVEESGGRLVTPGTPLTLTCTVSGFSLSYNAMNWVRQAPGKGLEW IGIIFASGRTDYASWAKGRFTISKTSTTVELKITSPTTEDTATYFCAR EGSTWGDALDPWGPGTLVTVSS |
| SEQ ID NO 36 | VH CD37-010 CDR1 | GFSLSYNA |
| SEQ ID NO 37 | VH CD37-010 CDR2 | IFASGRT |
| SEQ ID NO 38 | VH CD37-010 CDR3 | AREGSTWGDALDP |

TABLE 1-continued

| SEQ ID NO: | Name | Sequence |
|---|---|---|
| SEQ ID NO 39 | VL CD37-010 | AYDMTQTPSSVEAAVGGTVTIKCQASQNIIDYLAWYQQKPGQPPQL LIHKASTLASGVPSRFKGSGSGTQFTLTISGVQSDDAATYYCQQGYS NSNIDNTFGGGTEVVVK |
| SEQ ID NO 40 | VL CD37-010 CDR1 | QNIIDY |
|  | VL CD37-010 CDR2 | KAS |
| SEQ ID NO 41 | VL CD37-010 CDR3 | QQGYSNSNIDNT |
| SEQ ID NO 42 | VH CD37-016 | QSVEESGGRLVTPGTPLTLTCTVSGFSLSNYNMGWVRQAPGKGLE WIGVIDASGTTYYATWAKRFTCSKTSSTVELKMTSLTTEDTATYFC ARELLYFGSSYYDLWGQGTLVTVSS |
| SEQ ID NO 43 | VH CD37-016 CDR1 | GFSLSNYN |
| SEQ ID NO 44 | VH CD37-016 CDR2 | IDASGTT |
| SEQ ID NO 45 | VH CD37-016 CDR3 | ARELLYFGSSYYDL |
| SEQ ID NO 46 | VL CD37-016 | DVVMTQTPASVSEPVGGTVTIKCQASQNIDSNLAWYQQKPGQPPKF LIYYASNLPFGVSSRFKGSGSGTQFTLTISDLESADAATYYCQCADV GSTYVAAFGGGTEVVVK |
| SEQ ID NO 47 | VL CD37-016 CDR1 | QNIDSN |
|  | VL CD37-016 CDR2 | YAS |
| SEQ ID NO 48 | VL CD37-016 CDR3 | QCADVGSTYVAA |
| SEQ ID NO 49 | VH CD37-004-H5 | EVQLVESGGGLVQPGGSLRLSCAASGFSLSTYDMSWVRQAPGKGL EWVSIIYSSVGAYYASWAKGRFTISRDNSKNTLYLQMNSLRAEDTA VYYCAREYGASSSDYIFSLWGQGTLVTVSS |
| SEQ ID NO 22 | VH CD37-004-H5 CDR1 | GFSLSTYD |
| SEQ ID NO 23 | VH CD37-004-H5 CDR2 | IYSSVGA |
| SEQ ID NO 24 | VH CD37-004-H5 CDR3 | AREYGASSSDYIFSL |
| SEQ ID NO 50 | VL CD37-004-L2 | AQVLTQSPSPLSASVGDRVTITCQASQSVYNSQNLAWYQQKPGKA PKLLIYEASKLASGVPSRFKGSGSGTEFTLTISSLQPDDFATYYCQGE FSCISADCTAFGGGTKVEIK |
| SEQ ID NO 26 | VL CD37-004-L2 CDR1 | QSVYNSQN |
|  | VL CD37-004-L2 CDR2 | EAS |
| SEQ ID NO 27 | VL CD37-004-L2 CDR3 | QGEFSCISADCTA |
| SEQ ID NO 51 | VH CD37-005-H1 | QSVVESGGGLVQPGGSLRLSCTVSGFSLSSNAMNWVRQAPGKGLE WIGLIYASGNTDYASWAKGRFTISKTSTTVYLKITSPTAEDTATYFCA REGSVWGAAFDPWGGTLVTVSS |
| SEQ ID NO 29 | VH CD37-005-H1 CDR1 | GFSLSSNA |
| SEQ ID NO 30 | VH CD37-005-H1 CDR2 | IYASGNT |
| SEQ ID NO 31 | VH CD37-005-H1 CDR3 | AREGSVWGAAFDP |

TABLE 1-continued

| SEQ ID NO: | Name | Sequence |
|---|---|---|
| SEQ ID NO 52 | VL CD37-005-L2 | AYDMTQSPSSVSASVGDRVTITCQASQSISNWLAWYQQKPGKAPK QLIYAASTLASGVPSRFKGSGSGTDFTLTISSLQPEDFATYYCQQGY SNSNIDNTFGGGTKVEIK |
| SEQ ID NO 33 | VL CD37-005-L2 CDR1 | QSISNW |
|  | VL CD37-005-L2 CDR2 | AAS |
| SEQ ID NO 34 | VL CD37-005-L2 CDR3 | QQGYSNSNIDNT |
| SEQ ID NO 53 | VH CD37-010-H5 | EVQLVESGGGLVQPGGSLRLSCAASGFSLSYNAMNWVRQAPGKGL EWVSIIFASGRTDYASWAKGRFTISRDNSKNTLYLQMNSLRAEDTA VYYCAREGSTWGDALDPWGQGTLVTVSS |
| SEQ ID NO 36 | VH CD37-010-H5 CDR1 | GFSLSYNA |
| SEQ ID NO 37 | VH CD37-010-H5 CDR2 | IFASGRT |
| SEQ ID NO 38 | VH CD37-010-H5 CDR3 | AREGSTWGDALDP |
| SEQ ID NO 54 | VL CD37-010-L2 | AYDMTQSPSTLSASVGDRVTITCQASQNIIDYLAWYQQKPGKAPKL LIHKASTLASGVPSRFKGSGSGTEFTLTISSLQPDDFATYYCQQGYS NSNIDNTFGGGTKVEIK |
| SEQ ID NO 40 | VL CD37-010-L2 CDR1 | QNIIDY |
|  | VL CD37-010-L2 CDR2 | KAS |
| SEQ ID NO 41 | VL CD37-010-L2 CDR3 | QQGYSNSNIDNT |
| SEQ ID NO 55 | VH CD37-016-H5 | EVQLVESGGGLVQPGGSLRLSCAASGFSLSNYNMGWVRQAPGKGL EWSVIDASGTTYYATWAKGRPTISRDNSKNTLYLQMNSLRAEDTA TYYCARELLYFGSSYYDLWGQGTLVTVSS |
| SEQ ID NO 43 | VH CD37-016-H5 CDR1 | GFSLSNYN |
| SEQ ID NO 44 | VH CD37-016-H5 CDR2 | IDASGTT |
| SEQ ID NO 45 | VH CD37-016-H5 CDR3 | ARELLYPGSSYYDL |
| SEQ ID NO 56 | VL CD37-CD37-016-L2 | DVVMTQSPSTLSASVGDRVTITCQASQNIDSNLAWYQQKPGKAPKF LIYYASNLPFGVPSRFKGSGSGTEFTLTISSLQPDDFATYYCQCADVG STYVAAFGGGTKVEIK |
| SEQ ID NO 47 | VL CD37-016-L2 CDR1 | QNIDSN |
|  | VL CD37-016-L2 CDR2 | YAS |
| SEQ ID NO 48 | VL CD37-016-L2 CDR3 | QCADVGSTYVAA |
| SEQ ID NO 57 | VL CD37-016-L2-C90S | DVVMTQSPSTLSASVGDRVTITCQASQNIDSNLAWYQQKPGKAPKF LIYYASNLPFGVPSRFKGSGSGTEFTLTISSLQPDDFATYYCQSADVG STYVAAFGGGTKVEIK |
| SEQ ID NO 47 | VL CD37-016-L2-C90S CDR1 | QNIDSN |
|  | VL CD37-016-L2-C90S CDR2 | YAS |

TABLE 1-continued

| SEQ ID NO: | Name | Sequence |
|---|---|---|
| SEQ ID NO 58 | VL CD37-016-L2-C90S CDR3 | QSADVGSTYVAA |
| SEQ ID NO 59 | VH CD20-7D8 | EVQLVESGGGLVQPDRSLRLSCAASGFTFHDYAMHWVRQAPGKGL EWVSTISWNSGTIGYADSVKGRFTISRDNAKNSLYLQMNSLRAEDT ALYYCAKDIQYGNYYYGMDVWGQGTTVTVSS |
| SEQ ID NO 60 | VH CD20-7D8 CDR1 | GFTFHDYA |
| SEQ ID NO 61 | VH CD20-7D8 CDR2 | ISWNSGTI |
| SEQ ID NO 62 | VH CD20-7D8 CDR3 | AKDIQYGNYYYGMDV |
| SEQ ID NO 63 | VL CD20-7D8 | EIVLTQSPATLSLSPGERATLSCRASQSVSSYLAWYQQKPGQAPRLLI YDASNRATGIPARFSGSGSGTDFTLTISSLEPEDFAVYYCQQRSNW PITFGQGTRLEIK |
| SEQ ID NO 64 | VL CD20-7D8 CDR1 | QSVSSY |
|  | VL CD20-7D8 CDR2 | DAS |
| SEQ ID NO 65 | VL CD20-7D8 CDR3 | QQRSNWPIT |
| SEQ ID NO 66 | VH CD20-11B8 | EVQLVQSGGGLVHPGGSLRLSCTGSGFTFSYHAMHWVRQAPGKGL EWVSIIGTGGVTYYADSVKGRFTISRDNVKNSLYLQMNSLRAEDMA VYYCARDYYGAGSFYDGLYGMDVWGGTTVTVSS |
| SEQ ID NO 67 | VH CD20-11B8 CDR1 | GFTFSYHA |
| SEQ ID NO 68 | VH CD20-11B8 CDR2 | IGTGGVT |
| SEQ ID NO 69 | VH CD20-11B8 CDR3 | ARDYYGAGSFYDGLYGMDV |
| SEQ ID NO 70 | VL CD20-11B8 | EIVLTQSPATLSLSPGERATLSCRASQSVSSYLAWYQQKPGQAPRLLI YDASNRATGIPARFSGSGSGTDFTLTISSLEPEDFAVYYCQQRSDW PLTFGGGTKVEIK |
| SEQ ID NO 64 | VL 1 CD20-11B8 CDR1 | QSVSSY |
|  | VL CD20-11B8 CDR2 | DAS |
| SEQ ID NO 71 | VL CD20-11B8 CDR3 | QQRSDWPLT |
| SEQ ID NO 72 | VH CD20-ofatumumab | EVQLVESGGGLVQPGRSLRLSCAASGFTFNDYAMHWVRQAPGKGL EWVSTISWNSGSIGYADSVKGRFTISRDNAKKSLYLQMNSLRAEDT ALYYCAKDIQYGNYYYGMDVWGQGTTVTVSS |
| SEQ ID NO 73 | VH CD20-ofatumumab CDR1 | GFTFNDYA |
| SEQ ID NO 74 | VH CD20-ofatumumab CDR2 | ISWNSGSI |
| SEQ ID NO 62 | VH CD20-ofatumumab CDR3 | AKDIQYGNYYYGMDV |
| SEQ ID NO 63 | VL CD20-ofatumumab | EIVLTQSPATLSLSPGERATLSCRASQSVSSYLAWYQQKPGQAPRLLI YDASNRATGIPARFSGSGSGTDFTLTISSLEPEDFAVYYCQQRSNW PITFGQGTRLEIK |

TABLE 1-continued

| SEQ ID NO: | Name | Sequence |
|---|---|---|
| SEQ ID NO 64 | VL CD20-ofatumumab CDR1 | QSVSSY |
|  | VL CD20-ofatumumab CDR2 | DAS |
| SEQ ID NO 65 | VL CD20-ofatumumab CDR3 | QQRSNWPIT |
| SEQ ID NO 75 | VH CD20-rituximab | QVQLQQPGAELVKPGASVKMSCKASGYTFTSYNMHWVKQTPGRGL EWIGAIYPGNGDTSYNQKFKGKATLTADKSSSTAYMQLSSLTSEDS AVYYCARST YYGGDWYFNVWGAGTTVTVSA |
| SEQ ID NO 76 | VH CD20-rituximab CDR1 | GYTFTSYN |
| SEQ ID NO 77 | VH CD20-rituximab CDR2 | IYPGNGDT |
| SEQ ID NO 78 | VH CD20-rituximab CDR3 | ARST YYGGDWYFNV |
| SEQ ID NO 79 | VL CD20-rituximab | QIVLSQSPAILSASPGEKVTMTCRASSSVSYIHWFQQKPGSSPKPW IYATSNLASGVPVRFSGSGSGTSYSLTISRVEAEDAATYYCQQWTSNPPTFGGGTKLEIK |
| SEQ ID NO 80 | VL CD20-rituximab CDR1 | SSVSY |
|  | VL CD20-rituximab CDR2 | ATS |
| SEQ ID NO 81 | VL CD20-rituximab CDR3 | QQWTSNPPT |
| SEQ ID NO 82 | VH CD20-obinutuzumab | QVQLVQSGAEVKKPGSSVKVSCKASGYAFSYSWINWVRQAPGQGL EWMGRIFPGDGDTDYNGKFKGRVTITADKSTSTAYMELSSLRSEDT AVYYCARNVFDGYWLVYWGQGTLVTVSS |
| SEQ ID NO 83 | VH CD20-obinutuzumab CDR1 | GYAFSYSW |
| SEQ ID NO 84 | VH CD20-obinutuzumab CDR2 | IFPGDGDT |
| SEQ ID NO 85 | VH CD20-obinutuzumab CDR3 | ARNVFDGYWLVY |
| SEQ ID NO 86 | VL CD20-obinutuzumab | DIVMTQTPLSLPVTPGEPASISCRSSKSLLHSNGITYLYWYLQKPGQ SPQLLIYQMSNLVSGVPDRFSGSGSGTDFTLKISRVEAEDVGVYYCA QNLELPYTFGGGTKVEIK |
| SEQ ID NO 87 | VL CD20-obinutuzumab CDR1 | KSLLHSNGITY |
|  | VL CD20-obinutuzumab CDR2 | QMS |
| SEQ ID NO 88 | VL CD20-obinutuzumab CDR3 | AQNLELPYT |

TABLE 1-continued

| SEQ ID NO: | Name | Sequence |
|---|---|---|
| SEQ ID NO 89 | VH gp120-b12 | QVQLVQSGAEVKKPGASVKVSCQASGYRFSNFVIHWVRQAPGQRF EWMGWINPYNGNKEFSAKFQDRVTFTADTSANTAYMELRSLRSAD TAVYYCARVGPYSWDDSPQDNYYMDVWGKGTTVIVSS |
| SEQ ID NO 90 | VH gp120-b12 CDR1 | GYRFSNFV |
| SEQ ID NO 91 | VH gp120-b12 CDR2 | INPYNGNK |
| SEQ ID NO 92 | VH gp120-b12 CDR3 | ARVGPYSWDDSPQDNYYMDV |
| SEQ ID NO 93 | VL gp120-b12 | EIVLTQSPGTLSLSPGERATFSCRSSHSIRSRRVAWYQHKPGQAPRL VIHGVSNRASGISDRFSGSGSGTDFTLTITRVEPEDFALYYCQVYGA SSYTFGQGTKLERK |
| SEQ ID NO 94 | VL gp120-b12 CDR1 | HSIRSRR |
|  | VL gp120-b12 CDR2 | GVS |
| SEQ ID NO 95 | VL gp120-b12-CDR3 | QVYGASSYT |
| SEQ ID NO 96 | constant region human HC IgG1m(f) | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPSR EEMTKNQVSLTCLVKGFYPSDIAVEWESNGQPENNYKTTPPVLDSDG SFFLYSKLTVDKSRWQQGNVFSCSVMHEALHNHYTQKSLSLSPGK |
| SEQ ID NO 97 | constant region human HC IgG1m(z) | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KKVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPSR EEMTKNQVSLTCLVKGFYPSDIAVEWESNGQPENNYKTTPPVLDSDG SFFLYSKLTVDKSRWQQGNVFSCSVMHEALHNHYTQKSLSLSPGK |
| SEQ ID NO 98 | constant region human HC IgG1m(a) | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KPVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPSR DELTKNQVSLTCLVKGFYPSDIAVEWESNGQPENNYKTTPPVLDSDG SFFLYSKLTVDKSRWQQGNVFSCSVMHEALHNHYTQKSLSLSPGK |
| SEQ ID NO 99 | constant region human HC IgG1m(x) | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KPVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPSR EEMTKNQVSLTCLVKGFYPSDIAVEWESNGQPENNYKTTPPVLDSDG SFFLYSKLTVDKSRWQQGNVFSCSVMHEGLHNHYTQKSLSLSPGK |
| SEQ ID NO 100 | constant region human HC IgG1m(f)-E430G | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPREPQVYTLPPSR EEMTKNQVSLTCLVKGFYPSDIAVEWESNGQPENNYKTTPPVLDSDG SFFLYSKLTVDKSRWQQGNVFSCSVMHGALHNHYTQKSLSLSPGK |
| SEQ ID NO 101 | constant region human HC IgG1m(f)-E345K | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT VLHQDWLNGKEYKCKVSNKALPAPIEKTISKAKGQPRKPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| SEQ ID NO 102 | constant region human HC IgG1m(f)-E345R | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVD KRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLT |

TABLE 1-continued

| SEQ ID NO: | Name | Sequence |
|---|---|---|
| | | VLHQDWLNGKEYKCKVSNKALPAPIEKTISKAKGQPRRPQVYTLPPS<br>REEMTKNQVSLTCLVKGFYPSDIAVEWESNGQPENNYKTTPPVLDSD<br>GSFFLYSKLTVDKSRWQQGNVFSCSVMHEALHNHYTQKSLSLSPGK |
| SEQ ID NO 103 | constant region human HC IgG1m(f)-K439E | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVD<br>KRVEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSR<br>EEMTKNQVSLTCLVKGFYPSDIAVEWESNGQPENNYKTTPPVLDSDG<br>SFFLYSKLTVDKSRWQQGNVFSCSVMHEALHNHYTQESLSLSPGK |
| SEQ ID NO 104 | constant region human HC IgG1m(f)-S440K | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVD<br>KRVEPKSCDKTHTCPPCPAPELLGGPSVFLFPPKPKDTLMISRTPEVTC<br>VVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSR<br>EEMTKNQVSLTCLVKGFYPSDIAVEWESNGQPENNYKTTPPVLDSDG<br>SFFLYSKLTVDKSRWQQGNVFSCSVMHEALHNHYTQKKLSLSPGK |
| SEQ ID NO 105 | constant region human HC IgG2 | ASTKGPSVFPLAPCSRSTSESTAALGCLVKDYFPEPVTVSWNSGALTS<br>GVHTFPAVLQSSGLYSLSSVVTVPSSNFGTQTYTCNVDHKPSNTKVD<br>KTVERKCCVECPPCPAPPVAGPSVFLFPPKPKDTLMISRTPEVTCVVVD<br>VSHEDPEVQFNWYVDGVEVHNAKTKPREEQFNSTFRVVSVLTVVHQ<br>DWLNGKEYKCKVSNKGLPAPIEKTISKTKGQPREPQVYTLPPSREEMT<br>KNQVSLTCLVKGFYPSDIAVEWESNGQPENNYKTTPPMLDSDGSFFL<br>YSKLTVDKSRWQQGNVFSCSVMHEALHNHYTQKSLSLSPGK |
| SEQ ID NO 106 | constant region human HC IgG3 | ASTKGPSVFPLAPCSRSTSGGTAALGCLVKDYFPEPVTVSWNSGALT<br>SGVHTFPAVLQSSGLYSLSSVVTVPSSSLGTQTYTCNVNHKPSNTKV<br>DKRVELKTPLGDTTHTCPRCPEPKSCDTPPPCPRCPEPKSCDTPPPCP<br>RCPEPKSCDTPPPCPRCPAPELLGGPSVFLFPPKPKDTLMISRTPEVTC<br>VVVDVSHEDPEVQFKWYVDGVEVHNAKTKPREEQYNSTFRVVSVLT<br>VLHQDWLNGKEYKCKVSNKALPAPIEKTISKTKGQPREPQVYTLPPSR<br>EEMTKNQVSLTCLVKGFYPSDIAVEWESSGQPENNYNTTPPMLDSDG<br>SFFLYSKLTVDKSRWQQGNIFSCSVMHEALHNRFTQKSLSLSPGK |
| SEQ ID NO 107 | constant region human HC IgG4 | ASTKGPSVFPLAPCSRSTSESTAALGCLVKDYFPEPVTVSWNSGALTS<br>GVHTFPAVLQSSGLYSLSSVVTVPSSSLGTKTYTCNVDHKPSNTKVD<br>KRVESKYGPPCPSCPAPEFLGGPSVFLFPPKPKDTLMISRTPEVTCVVV<br>DVSQEDPEVQFNWYVDGVEVHNAKTKPREEQFNSTYRVVSVLTVLH<br>QDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSF<br>FLYSRLTVDKSRWQEGNVFSCSVMHEALHNHYTQKSLSLSLGK |
| SEQ ID NO 108 | Constant region human kappa LC | RTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGL<br>SSPVTKSFNRGEC |

EXAMPLES

Example 1

Antibody Production and Purification
Antibody Expression Constructs

For the expression of human and humanized antibodies used herein, variable heavy (VH) chain and variable light (VL) chain sequences were prepared by gene synthesis (GeneArt Gene Synthesis; ThermoFisher Scientific) and cloned in pcDNA3.3 expression vectors (ThermoFisher Scientific) containing IgG1 heavy chain (HC) and light chain (LC) constant regions. Desired mutations were introduced by gene synthesis. CD20 antibodies in this application have VH and VL sequences derived from previously described CD20 antibodies IgG1-CD20-7D8 (WO2004/035607; VH: SEQ ID NO 59; VL: SEQ ID NO 63), IgG1-CD20-11B8 (WO2004/035607; VH: SEQ ID NO 66; VL: SEQ ID NO 70), ofatumumab (WO2004/035607; VH: SEQ ID NO 72; VL: SEQ ID NO 63), rituximab (WO2005/103081; VH: SEQ ID NO 75; VL: SEQ ID NO 79) and obinutuzumab (GA101; U.S. Pat. No. 8.883.980; VH: SEQ ID NO 82; VL: SEQ ID NO 86). CD37 antibodies in this application have VH and VL sequences derived from previously described CD37 antibodies IgG1-CD37-37.3 (WO2011/112978; VH: SEQ ID NO 7; VL: SEQ ID NO 11) and IgG1-CD37-G28.1 (EP2241577; VH: SEQ ID NO 14; VL: SEQ ID NO 18). The generation and VH and VL sequences of the panel of chimeric CD37 antibodies IgG1-CD37-004, IgG1-CD37-005, IgG1-CD37-010 and IgG1-CD37-016 and of the corresponding humanized variants IgG1-CD37-004-H5L2, IgG1-CD37-005-H1L2, IgG1-CD37-010-H5L2, IgG1-CD37-016-H5L2 and IgG1-CD37-016-H5L2-C90S are described further below in this Example. The human IgG1 antibody b12, an HIV gp120-specific antibody was used as a negative control in some experiments (Barbas et al., J Mol Biol. 1993 Apr. 5;230(3):812-23; VH: SEQ ID NO 89; VL: SEQ ID NO 93).

Transient Expression Antibody Constructs

Antibodies were expressed as IgG1K. Plasmid DNA mixtures encoding both heavy and light chains of antibodies were transiently transfected in Expi293F cells (Gibco, Cat No A14635) using 293fectin (Life Technologies) essentially as described by Vink et al. (Vink et al., 2014 Methods, 65(1):5-10). Antibody concentrations in the supernatants were measured by absorbance at 280 nm. Antibody-containing supernatants were either directly used in in vitro assays, or antibodies were purified as described below.

Antibody Purification and Quality Assessment

Antibodies were purified by Protein A affinity chromatography. Culture supernatants were filtered over a 0.20 μM dead-end filter and loaded on 5 mL MabSelect SuRe columns (GE Healthcare), washed and eluted with 0.02 M sodium citrate-NaOH, pH 3. The eluates were loaded on a HiPrep Desalting column (GE Healthcare) immediately after purification and the antibodies were buffer exchanged into 12.6 mM $NaH_2PO_4$, 140 mM NaCl, pH 7.4 buffer (B. Braun or Thermo Fisher). After buffer exchange, samples were sterile filtered over 0.2 μm dead-end filters. Purified proteins were analyzed by a number of bioanalytical assays including capillary electrophoresis on sodium dodecyl sulfate-polyacrylamide gels (CE-SDS) and high-performance size exclusion chromatography (HP-SEC). Concentration was measured by absorbance at 280 nm. Purified antibodies were stored at 2-8° C.

Generation of CD37-Specific Antibodies

CD37 Antigen Expression and Purification

Codon-optimized constructs for expression of full length human (Homo sapiens) CD37 (Genbank accession No. NP_001765) (SEQ ID NO 1) and cynomolgus monkey (*Macaca fascicularis*) CD37 (mfCD37) (Genbank accession No. XP_005589942) (SEQ ID NO 2) were generated. In addition, the following codon-optimized constructs for expression of various variants of the extracellular domain (ECD) of CD37 were generated: a signal peptide encoding sequence followed by the second extracellular domain (EC2) of human CD37 (aa 112-241), fused to the Fc (CH2-CH3) domain of human IgG with a C-terminal His-tag (CD37EC2-FcHis, SEQ ID NO 3), and a similar construct for mfCD37 (CD37mfEC2-FcHis, SEQ ID NO 4). The constructs contained suitable restriction sites for cloning and an optimal Kozak (GCCGCCACC) sequence (Kozak et al., 1999 Gene 234:187-208). The constructs were cloned in the mammalian expression vector pcDNA3.3 (Invitrogen) or an equivalent vector.

The CD37 constructs were transiently transfected in Freestyle 293-F (HEK293F) cells (Life Technologies) using 293fectin (Life Technologies) essentially as described by the manufacturer, or in Freesyle CHO-S cells (CHO) (Life Technologies) by using the Freestyle Max reagent (Life Technologies) essentially as described by the manufacturer. Soluble proteins were transiently expressed in Expi293 cells (Life technologies) by using the ExpiFectamine 293 reagent (Life Technologies), essentially as described by the manufacturer.

The Fc fusion proteins (CD37EC2-FcHis and CD37mfEC2-FcHis) were purified from cell culture supernatant using Protein A affinity chromatography.

Generation of CD37-Specific Antibodies in Rabbits

Immunization of rabbits was performed at MAB Discovery GMBH (Neuried, Germany). Rabbits were repeatedly immunized with a mixture of CD37EC2-FcHis and CD37mfEC2-FcHis or HEK293F cells transiently expressing human CD37 or mfCD37. The blood of these animals was collected and B lymphocytes were isolated. Using a MAB Discovery proprietary process, single B cells were sorted into wells of microtiter plates and further propagated. The supernatants were analyzed for specific binding to human and mfCD37 transiently expressed on CHO-S cells (CHO-CD37 and CHO-mfCD37). Upon analyzing the primary screening results, primary hits were selected for sequencing.

Unique variable heavy chain (VH) and variable light chain (VL) encoding regions were gene synthesized and cloned into mammalian expression vectors encoding the human IgG1m(f) constant heavy chain region containing an E430G (EU numbering) hexamerization-enhancing mutation (SEQ ID NO 100) and the human kappa light chain constant region (SEQ ID NO 108). An unfavorable, unpaired cysteine in some antibody light chains was replaced by a serine during this process. The resulting recombinant rabbit/human chimeric antibodies were produced in Expi293 cells by transiently cotransfecting the heavy chain (HC) and light chain (LC) encoding expression vectors. Immunoglobulin-containing supernatants were either directly used in in vitro assays, or immunoglobulins were purified from the cell supernatant using Protein A affinity purification on a Dionex Ultimate 3000 HPLC system. The reactivity of the produced chimeric (variable domains rabbit, constant domains human containing mutation E430G) monoclonal antibodies was re-analyzed for binding to CHO-CD37 and CHO-mfCD37 cells. In addition, binding to the human lymphoma cell line Daudi was analyzed and an in vitro CDC functionality assay using Daudi cells was performed.

The amino acid sequences of the variable regions of the four chimeric CD37 antibodies used herein are listed in Table 1 and comprise the following CDRs:

|  | Sequence (IMGT) | SEQ ID NO |
|---|---|---|
| VH CD37-004 | | |
| CDR1 | GFSLSTYD | SEQ ID NO 22 |
| CDR2 | IYSSVGA | SEQ ID NO 23 |
| CDR3 | AREYGASSSDYIFSL | SEQ ID NO 24 |
| VL CD37-004 | | |
| CDR1 | QSVYNSQN | SEQ ID NO 26 |
| CDR2 | EAS | |
| CDR3 | QGEFSCISADCTA | SEQ ID NO 27 |
| VH CD37-005 | | |
| CDR1 | GFSLSSNA | SEQ ID NO 29 |
| CDR2 | IYASGNT | SEQ ID NO 30 |
| CDR3 | AREGSVWGAAFDP | SEQ ID NO 31 |
| VL CD37-005 | | |
| CDR1 | QSISNW | SEQ ID NO 33 |
| CDR2 | AAS | |
| CDR3 | QQGYSNSNIDNT | SEQ ID NO 34 |
| VH CD37-010 | | |
| CDR1 | GFSLSYNA | SEQ ID NO 36 |
| CDR2 | IFASGRT | SEQ ID NO 37 |
| CDR3 | AREGSTWGDALDP | SEQ ID NO 38 |

|  |  | Sequence (IMGT) | SEQ ID NO |
|---|---|---|---|
| VL CD37-010 | | | |
| | CDR1 | QNIIDY | SEQ ID NO 40 |
| | CDR2 | KAS | |
| | CDR3 | QQGYSNSNIDNT | SEQ ID NO 41 |
| VH CD37-016 | | | |
| | CDR1 | GFSLSNYN | SEQ ID NO 43 |
| | CDR2 | IDASGTT | SEQ ID NO 44 |
| | CDR3 | ARELLYFGSSYYDL | SEQ ID NO 45 |
| VL CD37-016 | | | |
| | CDR1 | QNIDSN | SEQ ID NO 47 |
| | CDR2 | YAS | |
| | CDR3 | QCADVGSTYVAA | SEQ ID NO 48 |

Humanization of the CD37-Specific Rabbit VH and VL Antibody Sequences

Humanization of the VH and VL antibody sequences from rabbit antibody clones CD37-004, CD37-005, CD37-010 and CD37-016 was performed at Antitope (Cambridge, UK) using germline humanization (CDR-grafting) technology. Humanized V region genes were designed based on human germline sequences that showed closest homology to the VH and VK amino acid sequences of the rabbit antibody sequences.

The heavy and light chain V region amino acid sequence were compared against a database of human germline V and J segment sequences in order to identify the heavy and light chain human sequences with the greatest degree of homology for use as human variable domain frameworks. The germline framework sequences used as the basis for the humanized designs are shown in Table 2.

TABLE 2

Closest matching human germline V segment and J segment sequences.

| | Heavy chain | | Light chain (κ) | |
|---|---|---|---|---|
| Rabbit anti-CD37 clone | Human V region germline segment | Human J region germline segment | Human V region germline segment | Human J region germline segment |
| 004 | IGHV3-53*04 | IGHJ4 | IGKV1-5*01 | IGKJ4 |
| 005 | IGHV3-53*04 | IGHJ4 | IGKV1-12*01 | IGKJ4 |
| 010 | IGHV3-53*04 | IGHJ4 | IGKV1-5*03 | IGKJ4 |
| 016 | IGHV3-53*04 | IGHJ4 | IGKV1-12*01 | IGKJ4 |

Structural models of the rabbit antibody V regions were generated using Swiss PDB and analyzed in order to identify amino acids in the V region frameworks that may be important for the binding properties of the antibody.

Series of four to six humanized VH and four or five humanized VK (VL) sequences were then designed for each of the rabbit clones by grafting the CDRs onto the frameworks and, if necessary, by back-mutating residues which may be critical for the antibody binding properties, as identified in the structural modelling, to rabbit residues. Variant sequences with the lowest incidence of potential T cell epitopes were then selected using Antitope's proprietary in silico technologies, iTope and TCED (T Cell Epitope Database) (Perry et al., New approaches to prediction of immune responses to therapeutic proteins during preclinical development (2008) Drugs in R&D, 9(6):385-96; Bryson et al., Prediction of immunogenicity of therapeutic proteins (2010) Biodrugs 24(1):1-8). For antibody IgG1-016-H5L2 a variant with a point mutation in the variable domain was generated to replace a free cysteine: IgG1-016-H5L2-LC90S. Finally, the nucleotide sequences encoding the designed variants have been codon-optimized.

The amino acid sequences of the variable regions of the selected humanized CD37 antibodies are listed in Table 1 and comprise the following CDRs:

|  |  | Sequence (IMGT) | SEQ ID NO |
|---|---|---|---|
| VH CD37-004-H5 | | | |
| | CDR1 | GFSLSTYD | SEQ ID NO 22 |
| | CDR2 | IYSSVGA | SEQ ID NO 23 |
| | CDR3 | AREYGASSSDYIFSL | SEQ ID NO 24 |
| VL CD37-004-L2 | | | |
| | CDR1 | QSVYNSQN | SEQ ID NO 26 |
| | CDR2 | EAS | |
| | CDR3 | QGEFSCISADCTA | SEQ ID NO 27 |
| VH CD37-005-H1 | | | |
| | CDR1 | GFSLSSNA | SEQ ID NO 29 |
| | CDR2 | IYASGNT | SEQ ID NO 30 |
| | CDR3 | AREGSVWGAAFDP | SEQ ID NO 31 |
| VL CD37-005-L2 | | | |
| | CDR1 | QSISNW | SEQ ID NO 33 |
| | CDR2 | AAS | |
| | CDR3 | QQGYSNSNIDNT | SEQ ID NO 34 |
| VH CD37-010-H5 | | | |
| | CDR1 | GFSLSYNA | SEQ ID NO 36 |
| | CDR2 | IFASGRT | SEQ ID NO 37 |
| | CDR3 | AREGSTWGDALDP | SEQ ID NO 38 |
| VL CD37-010-L2 | | | |
| | CDR1 | QNIIDY | SEQ ID NO 40 |
| | CDR2 | KAS | |
| | CDR3 | QQGYSNSNIDNT | SEQ ID NO 41 |
| VH CD37-016-H5 | | | |
| | CDR1 | GFSLSNYN | SEQ ID NO 43 |
| | CDR2 | IDASGTT | SEQ ID NO 44 |
| | CDR3 | ARELLYFGSSYYDL | SEQ ID NO 45 |

-continued

|      | Sequence (IMGT) | SEQ ID NO |
|------|-----------------|-----------|
|      | VL CD37-016-L2  |           |
| CDR1 | QNIDSN          | SEQ ID NO 47 |
| CDR2 | YAS             |           |
| CDR3 | QCADVGSTYVAA    | SEQ ID NO 48 |
|      | VL CD37-016-L2-C90S |       |
| CDR1 | QNIDSN          | SEQ ID NO 47 |
| CDR2 | YAS             |           |
| CDR3 | QSADVGSTYVAA    | SEQ ID NO 58 |

Example 2

Complement-Mediated Cytotoxicity by Mixtures of Wild Type CD37 and CD20 Antibodies Complement recruitment is a key characteristic distinction between type I CD20 antibodies, which mediate strong complement-dependent cytotoxicity (CDC) and type II CD20 antibodies, which only mediate weak CDC activity in cellular assays (Cragg and Glennie 2004 Blood 103:2738-43). Here, the effect of combining a wild type (WT) type I CD20 antibody or a WT type II CD20 antibody with a WT CD37 antibody was tested in a CDC assay using Daudi cells. Daudi cells were cultured in RPMI 1640 supplemented with 10% heat-inactivated fetal bovine serum (FBS), 1 U/mL penicillin, 1 µg/mL streptomycin, and 4 mM L-glutamine. For the in vitro CDC assay, $0.1 \times 10^6$ Daudi cells (ATCC, Cat No CCL-213) were pre-incubated in polystyrene round-bottom 96-well plates (Greiner bio-one, Cat No 650101) with a concentration dilution series of purified antibodies in a total volume of 80 µL RPMI culture medium supplemented with 0.2% bovine serum albumin (BSA) for 15 min on a shaker at room temperature (RT). Next, 20 µL normal human serum (NHS; Sanquin, Ref No M0008) was added as a source of complement and incubated in a 37° C. incubator for 45 min (20% final NHS concentration; 1:1 antibody mixtures at final total concentrations of 0.06-8.0 µg/mL in 2-fold dilutions). Next, 20 µL of 2 µg/mL propidium iodide solution (PI; Sigma Aldrich) was added and incubated for 5 minutes on a shaker at RT. The cells were pelleted by centrifugation for 3 minutes at 1,200 rpm and resuspended in FACS buffer (PBS/0.1% BSA/0.01% Na-Azide). The number of PI-positive cells was determined by flow cytometry on an iQue screener (Intellicyt). The data were analyzed using best-fit values of a non-linear dose-response fit using log-transformed concentrations using GraphPad PRISM software. The percentage lysis was calculated as (number of PI-positive cells total number of cells)×100%.

As expected for a type I CD20 antibody IgG1-CD20-7D8 already showed potent CDC activity as a single agent whereas the CD37 antibody IgG1-CD37-37.3 did not (FIG. 1A). The mixture of both antibodies induced dose-dependent killing comparable to the single IgG1-CD20-7D8 antibody samples, even though the total concentration of CD20 antibody in the mixture was half that of in the IgG1-CD20-7D8 single agent sample.

Figure 1B:
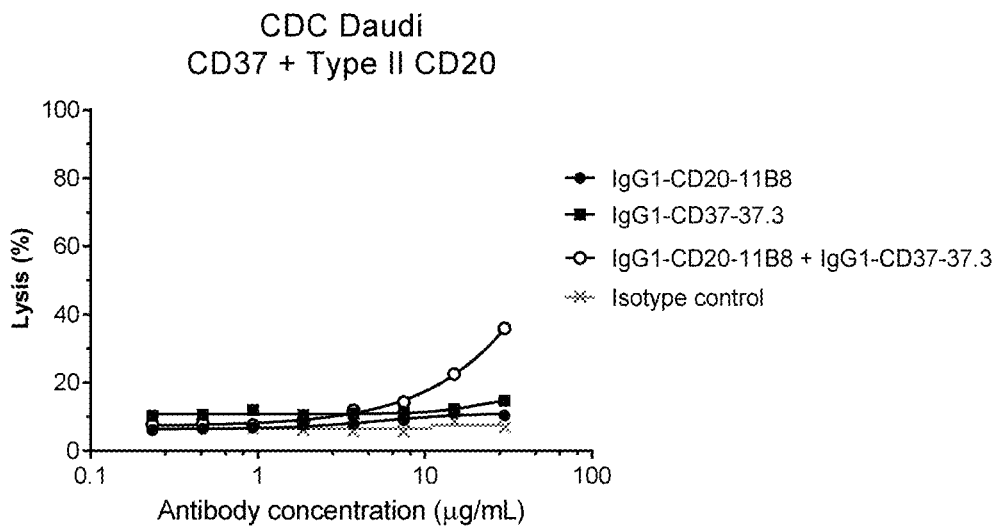

Although neither the WT type II CD20 antibody IgG1-CD20-11B8 nor the CD37 antibody IgG1-CD37-37.3 induced CDC by itself as single agents, the mixture of both antibodies did induce CDC on Daudi cells (FIG. 1B).

Example 3

CDC Synergy Analysis for Mixtures of CD37 and CD20 Antibodies with a Hexamerization-Enhancing Mutation The potential synergy between CD37 and CD20 antibodies with a hexamerization-enhancing mutation (E430G; WO2013/004842) was analyzed in CDC assays using Daudi cells. In vitro CDC assays were performed, essentially as described in Example 2, using a full concentration dilution series matrix (8×8 grid) of mixtures of hexamerization-enhanced CD37 antibody IgG1-CD37-37.3-E430G (Hx-CD37-37.3) (0.0125-0.8 µg/mL in 2-fold dilutions) with hexamerization-enhanced CD20 antibody IgG1-CD20-11B8-E430G (Hx-CD20-11B8) (0.125-8 µg/mL in 2-fold dilutions) or hexamerization-enhanced CD20 antibody IgG1-CD20-7D8-E430G (Hx-CD20-7D8) (0.0125-0.8 µg/mL in 2-fold dilutions). Hx-CD20-11B8 was derived from a type II CD20 antibody, and Hx-CD20-7D8 was derived from a type I CD20 antibody. The degree of synergy between the hexamerization-enhanced CD20 and CD37 antibodies in the CDC assays was determined using the Loewe additivity-based Combination Index (CI) score calculated by CompuSyn, whereby effects were categorized as additive (CI=1), synergistic (CI<1) or antagonistic (CI>1) (Chou et al., 2006 Pharmacological Reviews 58(3):621).

The hexamerization-enhanced CD37 antibody Hx-CD37-37.3 showed synergistic activity with each of the hexamerization-enhanced CD20 antibodies, Hx-CD20-7D8 (FIG. 2A) and Hx-CD20-11B8 (FIG. 2B), with average CI values of 0.37 and 0.31 (effective dose—ED95), respectively. At the lower range of the tested antibody concentrations, the mixtures of Hx-CD37-37.3 with Hx-CD20-11B8 (FIG. 2D) showed higher CI values than the mixtures of Hx-CD37-37.3 with Hx-CD20-7D8, indicating higher synergistic activity for the mixture of Hx-CD37-37.3 with the type II CD20 antibody-derived Hx-CD20-11B8 than with the type I CD20 antibody-derived Hx-CD20-7D8 (FIG. 2C).

Example 4

Efficiency of C1q Binding and using Bound C1q to Activate Complement and Induce CDC by Mixtures of Hexamerization-Enhanced CD37 and CD20 Antibodies The capacity of the mixtures of a hexamerization-enhanced CD37 antibody (Hx-CD37-37.3) and hexamerization-enhanced CD20 antibodies (Hx-CD20-7D8 or Hx-CD20-11B8) to bind and use C1q to activate complement and induce CDC on target cells was measured in vitro. To assess the efficiency of C1q binding by membrane-bound antibodies, Daudi cells were incubated with a fixed antibody concentration and serial dilutions of purified C1q. $0.1 \times 10^6$ cells were incubated in polystyrene round-bottom 96-well plates with purified C1q (0.001-10 µL/mL final concentrations in 3-fold dilutions; Quidel, Cat No A400) and 10 µg/mL antibodies in a total volume of 100 µL RPMI/0.2% BSA per well for 15 min on a shaker at RT, followed by 45 minutes at 37° C. The plates were put on ice, the cells were washed once with FACS buffer and then incubated with a Fluorescein isothiocyanate (FITC)-labeled rabbit anti-human C1q secondary antibody (1:80; DAKO, Cat No 0254)

in a total volume of 50 μL RPMI/0.2% BSA for 30 minutes at 4° C. Cells were pelleted, washed twice, resuspended in 120 μL FACS buffer and analyzed by flow cytometry on a FACS Canto II flow cytometer (BD Biosciences). To assess the efficiency of hexamerization-enhanced antibody (mixtures) to use bound C1q to activate complement and induce CDC, also referred to here as the CDC efficacy, was assessed in vitro using Daudi cells with a fixed antibody concentration and serial dilutions of purified C1q in C1q-depleted serum. $0.1 \times 10^6$ Daudi cells were pre-incubated with antibodies in a total volume of 100 μL RPMI/0.2% BSA per well for 15 min on a shaker at RT. Next, C1q-depleted serum (Quidel, Cat No A509) and a concentration dilution series of purified C1q were added to the pre-incubated cells to a final volume of 100 μL (10 μg/mL antibody; 20% C1q-depleted serum; 0.001-10 μg/mL C1q in 3-fold dilutions) and incubated for 45 minutes at 37° C. The reaction was stopped by putting the plates on ice before centrifugation and resuspending the cells in 20 μL PI (2 μg/mL). CDC was calculated as the fraction PI-positive cells (%) determined by flow cytometry using a FACS Canto II flow cytometer. Log-transformed data were analyzed using best-fit values of a non-linear dose-response fit using GraphPad PRISM software.

Figure 3A:
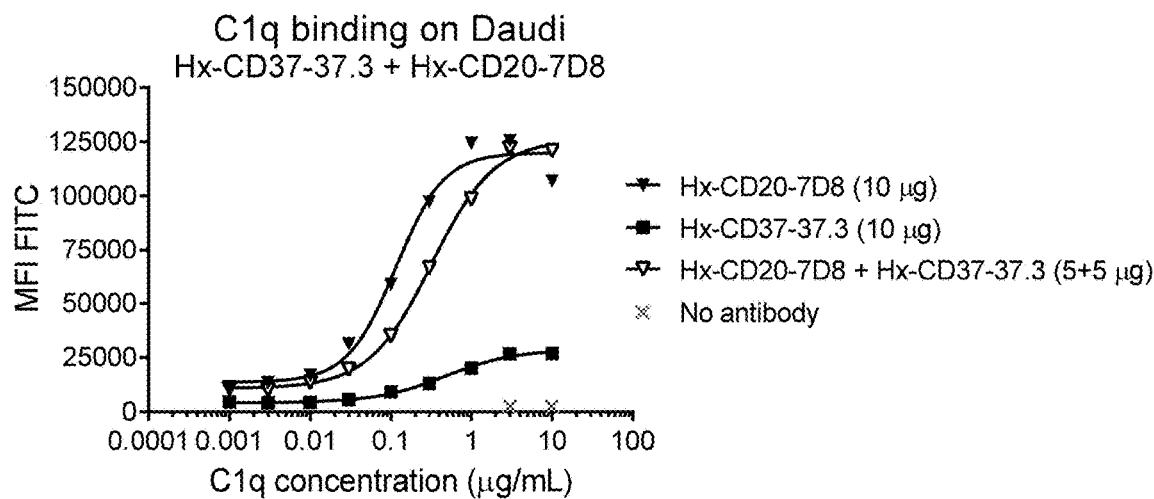
FIGS. 3A-3D show the complement binding and activating capacities for mixtures of hexamerization-enhanced CD37 and CD20 antibodies on Daudi cells.
Figure 3B:
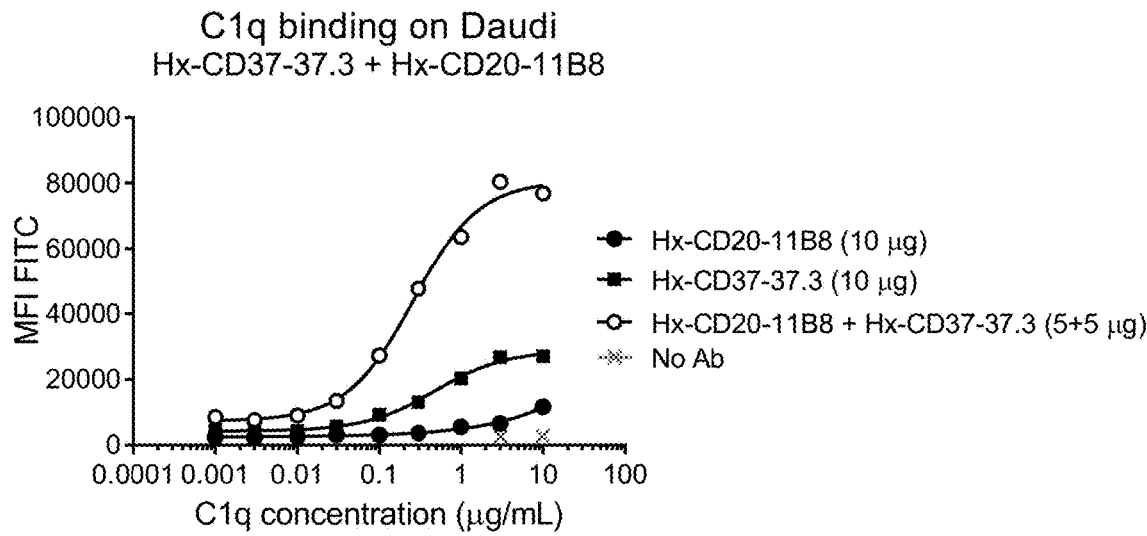
Figure 3C:
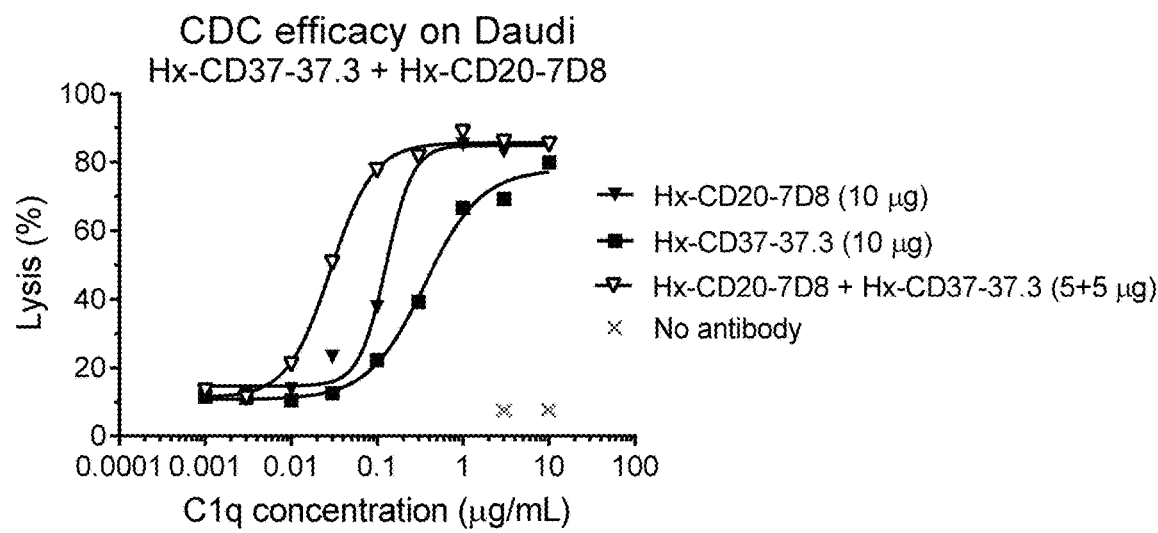
Figure 3D:
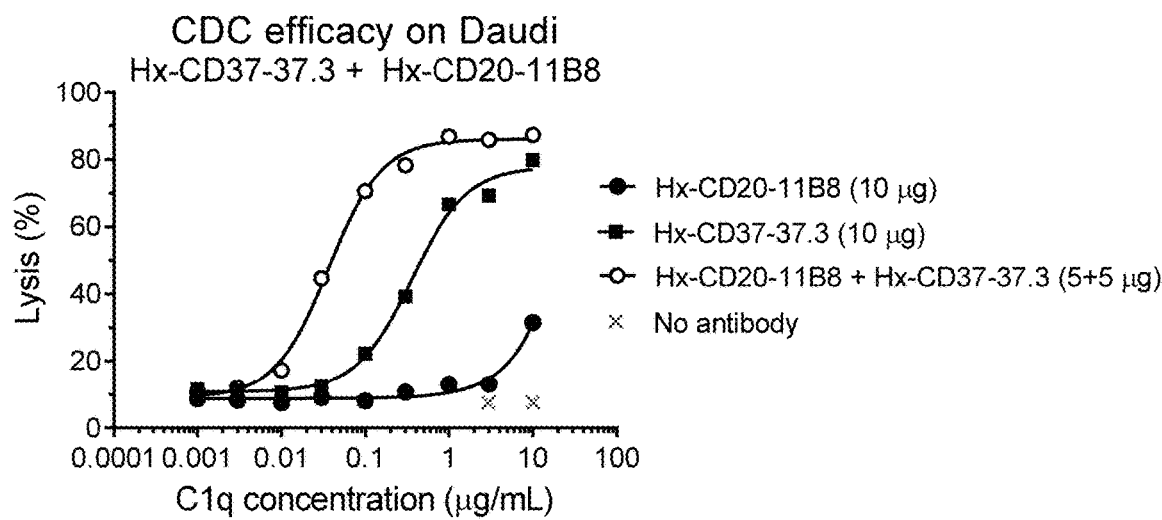

The hexamerization-enhanced CD37 antibody IgG1-CD37-37.3-E430G (Hx-CD37-37.3) showed limited C1q binding when bound to Daudi cells and did not significantly contribute to C1q binding in a mixture with the hexamerization-enhanced type I CD20 antibody-derived IgG1-CD20-7D8-E430G (Hx-CD20-7D8), which already showed efficient dose-dependent C1q binding as a single agent (FIG. 3A). However, the mixture Hx-CD37-37.3+Hx-CD20-7D8 used C1q more efficiently to activate complement and induce CDC compared to the single antibodies, as shown by enhanced CDC at lower C1q concentrations (lower EC50) while the total antibody concentration was the same (FIG. 3C). The mixture of Hx-CD37-37.3 with the type II CD20 antibody-derived Hx-CD20-11B8 resulted in substantially increased dose-dependent C1q binding compared to the single antibodies (FIG. 3B). In addition, C1q was efficiently used by the mixture of Hx-CD37-CD37.3 and Hx-CD20-11B8 as shown by increased CDC efficacy compared to the single antibodies (FIG. 3D). Together, these data illustrate that upon antigen binding on the cell surface, the mixtures of the hexamerization-enhanced CD37 and CD20 antibodies show substantial C1q recruitment and complement activation on the cell surface resulting in higher CDC-mediated killing of the target cells compared to the single antibodies, both for type I and type II CD20 antibody-derived hexamerization-enhanced molecules.

Example 5

FRET Analysis to Assess the Colocalization of IgG1-CD20-11B8 and IgG1-CD37-37.3 Antibody Variants on the Cell Membrane of Daudi Cells The molecular proximity of CD20 antibody variants of IgG1-CD20-11B8 and CD37 antibody variants of IgG1-CD37-37.3 bound to the cell membrane of Daudi cells was analyzed by fluorescence resonance energy transfer (FRET) analysis. The principle of FRET involves distance-dependent transfer of energy from an excited molecular fluorophore from the donor molecule (D) to another fluorophore on the acceptor molecule (A) (Forster 1965 Modern Quantum Chemistry Vol.3:93-137), which can be for example antibodies conjugated with donor and acceptor fluorophores.

Antibodies were directly conjugated to donor Alexa Fluor 555 (A555, Life Technologies, Cat No A37571) or acceptor Alexa Fluor 647 (A647, Life Technologies, Cat No A20186) essentially as described by the manufacturer. The labeled antibodies were purified using PD10-Sephadex G25 columns (GE Healthcare, Cat No GE17-0853-01) with 1× Tris buffer+azide (50 mM Tris, 100 mM NaCl, 0.01% azide, pH 8.0) as mobile phase. The degree of labeling (DOL) was determined from the absorption spectrum of the labeled antibodies (Nanodrop photospectrometer, Thermo Fisher Scientific) to be 3 dye molecules per antibody molecule on average.

$0.5 \times 10^6$ Daudi cells/well were incubated with 10 μg/mL A555-conjugated donor antibodies and/or 10 μg/mL A647-conjugated acceptor antibodies in a total volume of 100 μL RPMI/0.2% BSA in 96-well round-bottom plates (Greiner Bio-One, Cat No 650101) for 15 minutes at 37° C. in a water bath. Cells were washed twice with FACS buffer, pelleted by centrifugation (3 min at 300×g) and resuspended in 200 μL PBST. Mean fluorescence intensities (MFI) were determined by flow cytometry on a FACS Canto II (BD Biosciences) by recording 10,000 events at 585/42 nm (FL2, donor A555) and ≥6.70 nm (FL3), both excited at 488 nm, and at 660/20 nm (FL4, acceptor A647), excited at 635 nm. Unquenched donor fluorescence intensity was determined from cells incubated with only A555-conjugated donor antibodies, and non-enhanced acceptor intensity was determined from cells incubated with only A647-conjugated acceptor antibodies. Proximity-induced FRET was determined by measuring the energy transfer between cells incubated with both A555-conjugated donor and A647-conjugated acceptor antibodies. MFI values were used to calculate FRET according to the following equation: energy transfer (ET)=FL3(D,A)−FL2(D,A)/a−FL4(D,A)/b, wherein a=FL2(D)/FL3(D), b=FL4(A)/FL3(A), D is donor, A is acceptor and FLn (D,A)=donor+acceptor. ET values obtained were normalized according to the following equation: normalized energy transfer (%)=100*ET/FL3(D, A).

Figure 4A:
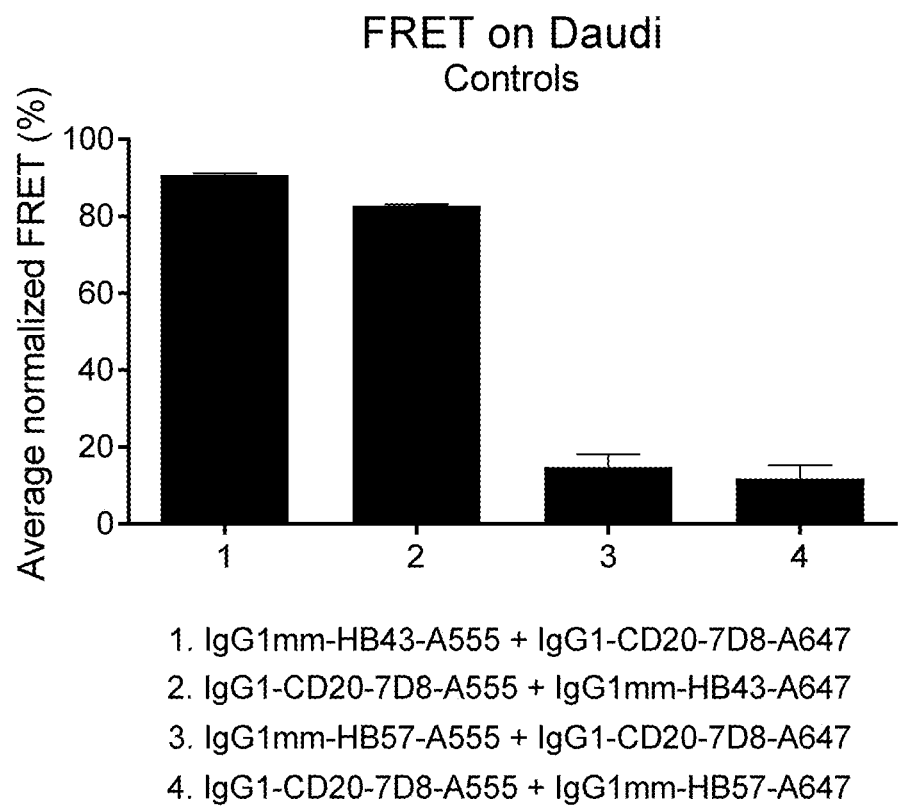
FIGS. 4A-4E show fluorescence resonance energy transfer (FRET) analysis of the molecular proximity between IgG1-CD20-11B8 and IgG1-CD37-37.3 antibody variants on the cell membrane of Daudi cells.

First, the dynamic range of FRET analysis by flow cytometry in this example was determined using control antibodies. The mouse anti-human IgG1 antibody HB43 (IgG1 mm-HB43; a gift from Ron Taylor, University of Virginia, Charlottesville, VA) was used as a positive control for proximity-induced FRET by virtue of its ability to directly bind, and thus colocalize with a human IgG1 antibody, such as the WT CD20 antibody IgG1-CD20-7D8 on the cell surface. As binding of A555- or A647-conjugated HB43 requires a cell surface-bound IgG1 antibody, unconjugated IgG1-CD20-7D8 was used for primary binding in the single stainings (calculating the unquenched donor and non-enhanced acceptor fluorescence intensities) and A555- or A647-conjugated IgG1-CD20-7D8 antibody was used for primary binding in the combination stainings (calculating energy transfer efficiency). Using the same setup, the mouse anti-human IgM antibody HB57 (IgG1 mm-HB57; a gift from Ron Taylor, University of Virginia, Charlottesville, VA) was used as a negative control for proximity-induced FRET. HB57 is a murine antibody that binds membrane-bound human IgM (B cell receptor) on Daudi cells, and was expected to poorly colocalize with the human antibody IgG1-CD20-7D8. FIG. 4A shows that conjugated IgG1-CD20-7D8 and IgG1-HB43 efficiently colocalized with an energy transfer efficiency of 90%, while IgG1-CD20-7D8 and IgG1-HB57 poorly colocalized with ~10% energy transfer efficiency. These data validated the flow cytometry FRET analysis to assess antibody colocalization using A555- and A647-conjugated antibodies.

Figure 4B:
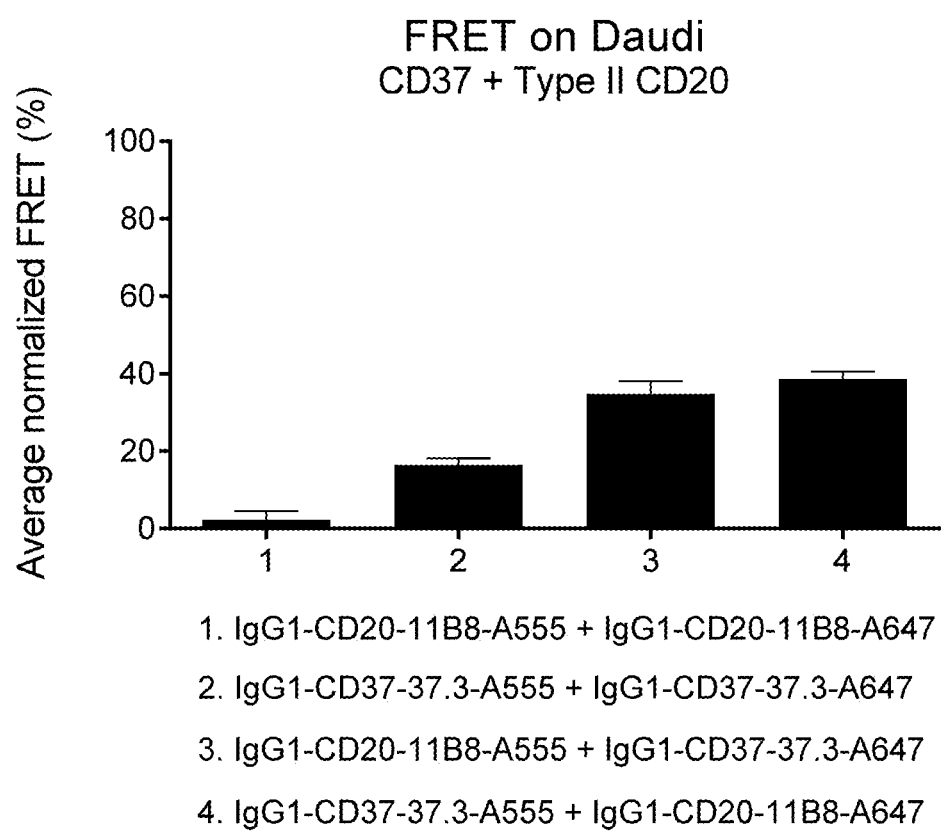
Figure 4C:
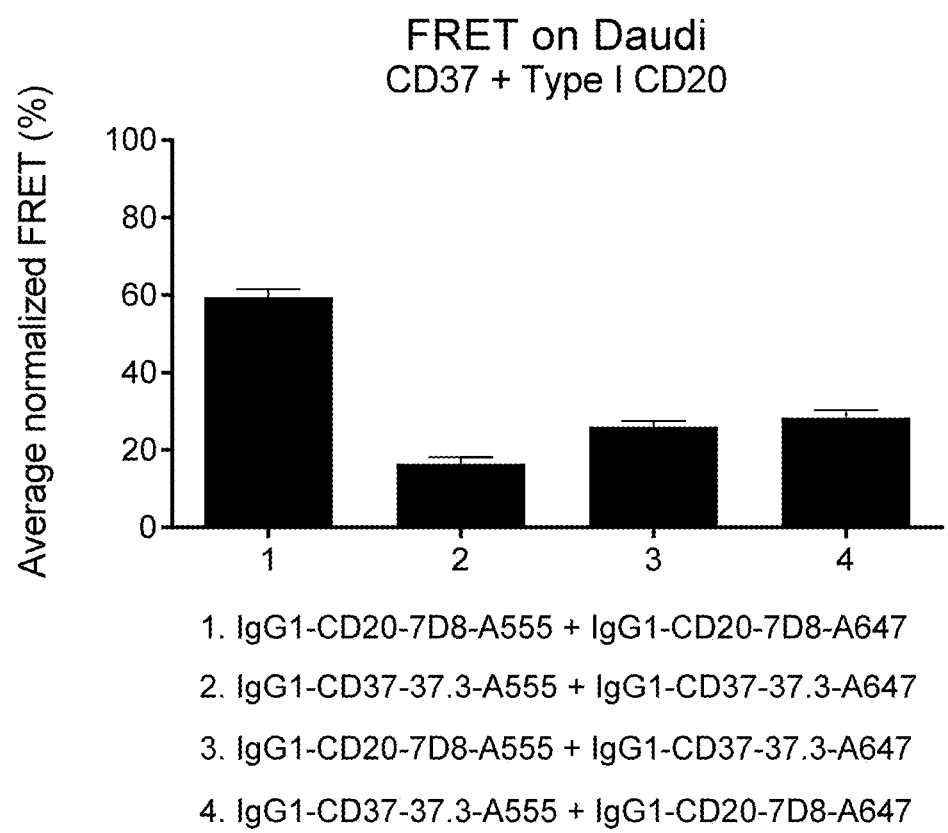

The proximity of WT CD37 antibody IgG1-CD37-37.3 and WT CD20 antibodies IgG1-CD20-7D8 and IgG1-CD20-11B8 on Daudi cells was evaluated for the single antibodies and the mixtures of the CD37 antibody with one of the CD20 antibodies. For the type II CD20 antibody IgG1-CD20-11B8, mixing donor and acceptor molecules did not result in proximity-induced FRET, whereas for the CD37 antibody IgG1-CD37-37.3, modest FRET was observed (FIG. 4B). In contrast, the mixture of donor-labeled IgG1-CD20-11B8 and acceptor-labeled IgG1-CD37-37.3 antibodies (and vice versa), showed increased FRET compared to each single antibody alone, indicating close proximity of the two antibodies on the cell surface. FIG. 4C shows that for the type I CD20 antibody IgG1-CD20-7D8, high FRET levels were observed for the CD20 antibody itself. The mixture of donor-labeled IgG1-CD20-7D8 and acceptor-labeled IgG1-CD37-37.3 antibodies (and vice versa) also demonstrated enhanced FRET levels, whereas FRET levels for IgG1-CD37-37.3 were low.

Figure 4D:
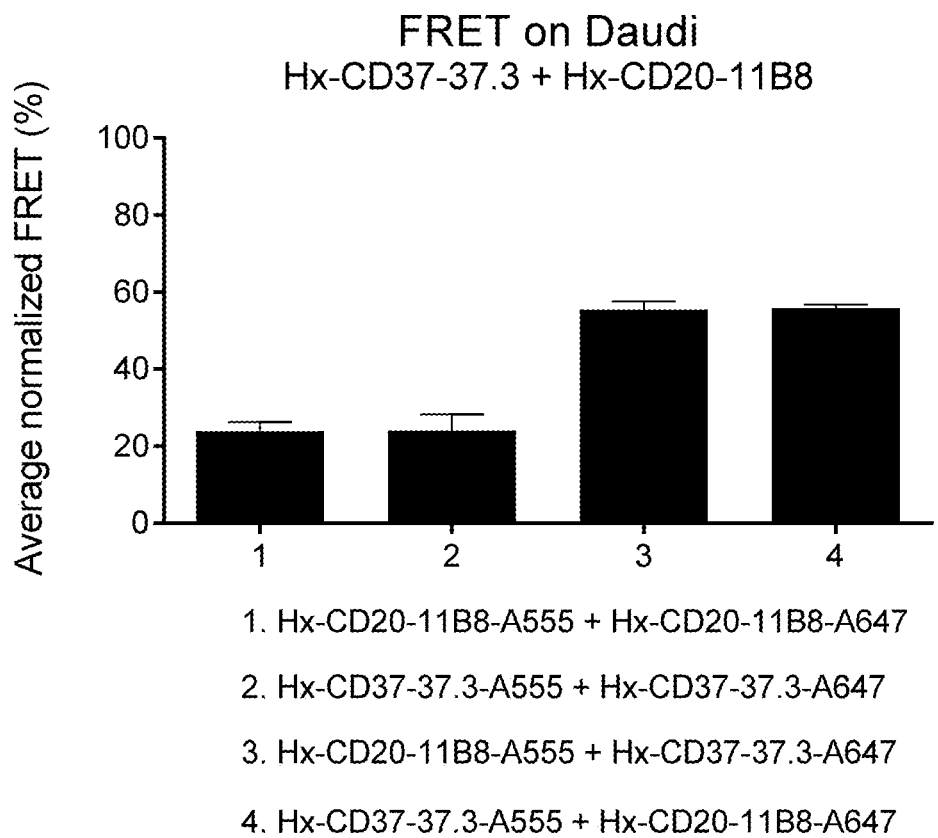
Figure 4E:
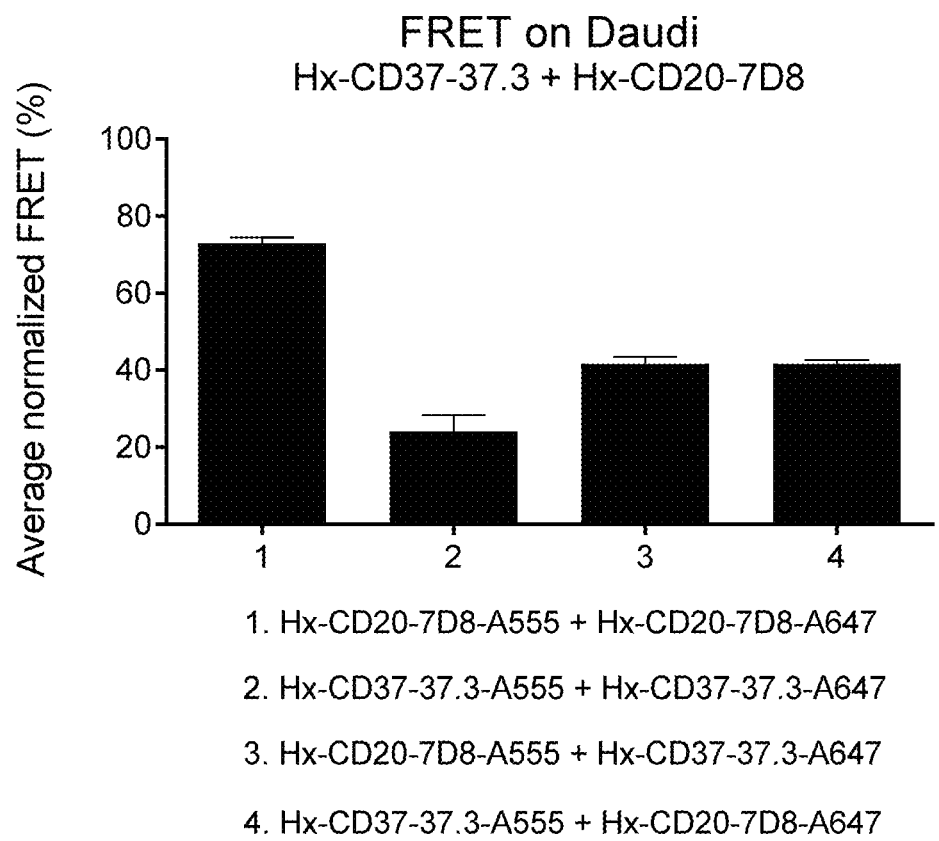

Next, the same approach was performed to analyze the proximity of hexamerization-enhanced CD37 antibody IgG1-CD37-37.3-E430G (Hx-CD37-37.3) and hexamerization-enhanced CD20 antibodes IgG1-CD20-7D8-E430G (Hx-CD20-7D8) and IgG1-CD20-11B8-E430G (Hx-CD20-11B8) on Daudi cells. Mixing donor and acceptor molecules of Hx-CD37-37.3 and mixing donor and acceptor molecules of Hx-CD20-11B8 showed low FRET levels (FIG. 4D). Increased FRET was observed for the mixture of donor-labeled Hx-CD20-11B8 and acceptor-labeled Hx-CD37-37.3 molecules (and vice versa). This indicates close molecular proximity between the hexamerization-enhanced CD20 and CD37 antibodies when allowed to bind together on Daudi cells. FIG. 4E shows that high FRET levels were observed for the CD20-targeting molecule Hx-CD20-7D8 by itself and low FRET levels for the CD37 targeting molecule Hx-CD37-37.3 by itself. Compared to the CD37 targeting molecule Hx-CD37-37.3 by itself, the mixture of donor-labeled Hx-CD20-7D8 and acceptor-labeled Hx-CD37-37.3 antibodies (and vice versa) demonstrated enhanced FRET levels.

Together, these data illustrate that both WT and hexamerization-enhanced antibodies in mixtures of CD37 antibodies with either type I or type II CD20 antibodies show binding in close proximity of each other on Daudi cells.

Example 6

Evaluation of Hetero-Hexamer Formation between Hexamerization-Enhanced CD37 and CD20 Antibodies on the Cell Surface of Malignant B cells using CDC Analysis K439E and S440K are complementary mutations that can be applied to modify intermolecular Fc-Fc interactions between surface target-bound antibodies. Antibodies carrying the K439E or S440K mutation show limited capacity to engage in Fc-Fc interactions and hexamer formation, whereas combining antibodies carrying the K439E mutation with antibodies carrying the S440K mutation rescues the capacity to engage in Fc-Fc interactions (WO2013/004842). The K439E and S440K mutations were introduced in Hx-CD20-11B8 and Hx-CD37-37.3 and the capacity of the mixtures of these variants to induce CDC was tested in vitro using Daudi and WIL2-S cells (ATCC, Cat No CRL-8885). $0.1 \times 10^6$ cells were pre-incubated in polystyrene round-bottom 96-well plates with concentration dilution series of purified antibody samples (final concentration range 0.03-10 µg/mL in 3-fold dilutions) in 80 µL culture medium [(RPMI 1640 with Hepes and L-Glutamine (Lonza, Cat No BE12-115F), supplemented with 10% Donor Bovine Serum with Iron (DBSI; Life Technologies, Cat No 10371-029) and 50 Units Penicillin/50 Units Streptomycin (Pen/Strep; Lonza, Cat No DE17-603E)] for 15 min on a shaker at RT. Next, 20 µL normal human serum (NHS, Sanquin, Ref No M0008) was added as a source of complement (20% final NHS concentration) and incubated for 45 minutes at 37° C. The reaction was stopped by putting the plates on ice before pelleting the cells by centrifugation and replacing the supernatant by 30 µL PI (2 µg/mL). CDC activity was determined by the percentage PI-positive cells measured by flow cytometry using an Intellicyt iQue screener. Log-transformed data were analyzed using best-fit values of a non-linear dose-response fit in GraphPad PRISM.

Figure 5A:
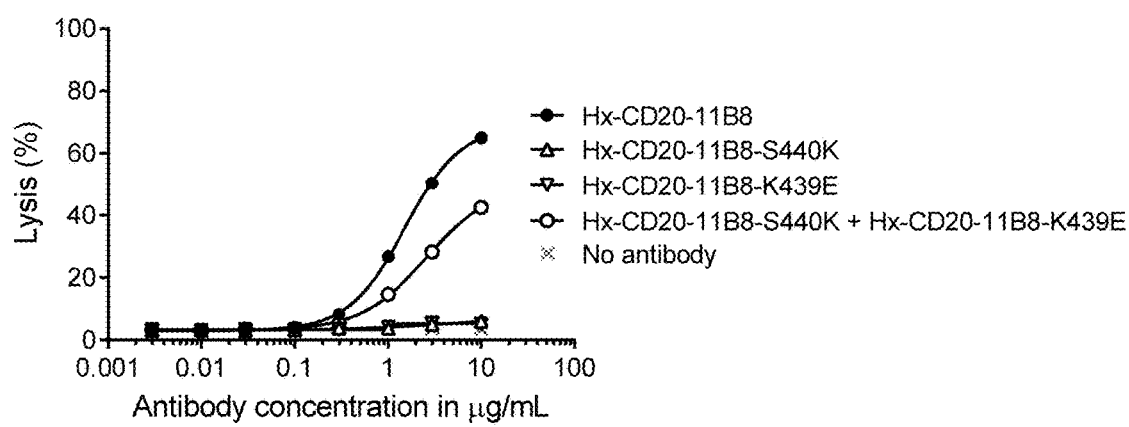
FIGS. 5A-5F show the effect of introducing the K439E and S440K mutations on the CDC activity of IgG1-CD20-11B8-E430G (Hx-CD20-11B8) on Daudi (FIG. 5A) and WIL2-S (FIG. 5B) cells, IgG1-CD37-37.3-E430G (Hx-CD37-37.3) on Daudi (FIG. 5C) and WIL2-S cells (FIG. 5D), and the antibody combinations on Daudi (FIG. 5E) and WIL2-S cells (FIG. 5F). Daudi and WIL2-S cells were incubated with concentration series of the CD20 and/or CD37 antibody variants in the presence of 20% NHS. CDC activity is presented as the percentage lysis determined by the percentage propidium iodide (PI)-positive cells. A sample without antibody was used as negative control for CDC activity.
Figure 5B:
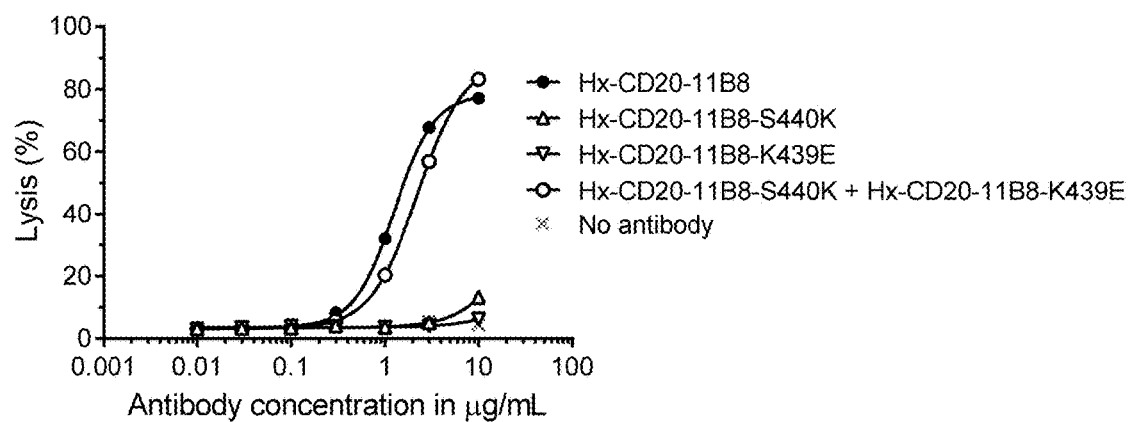
Figure 5C:
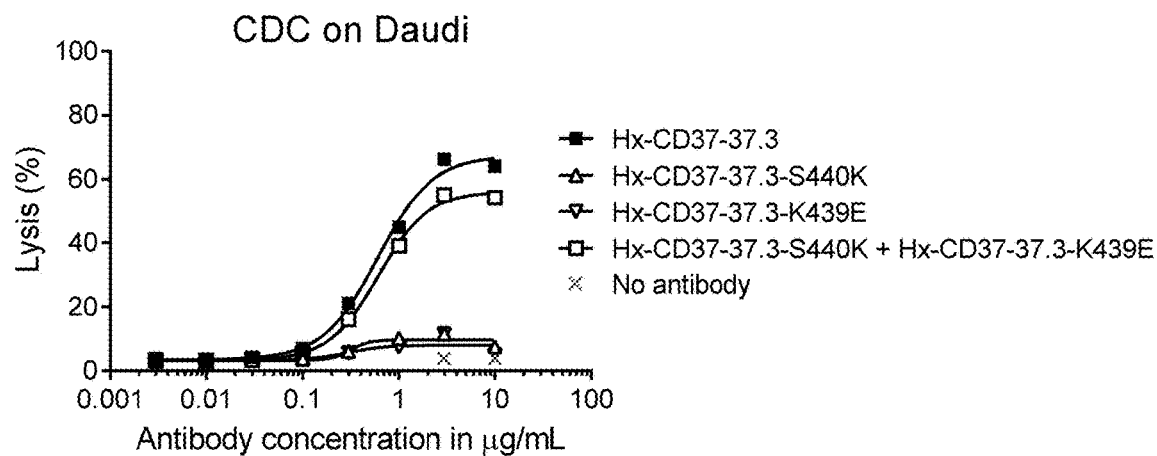
Figure 5D:
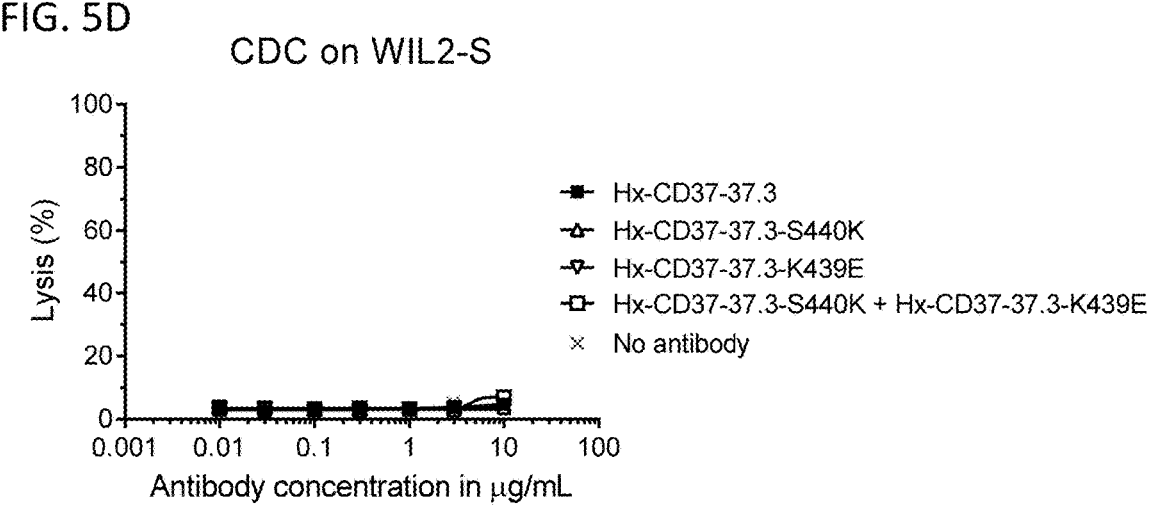
Figure 5E:
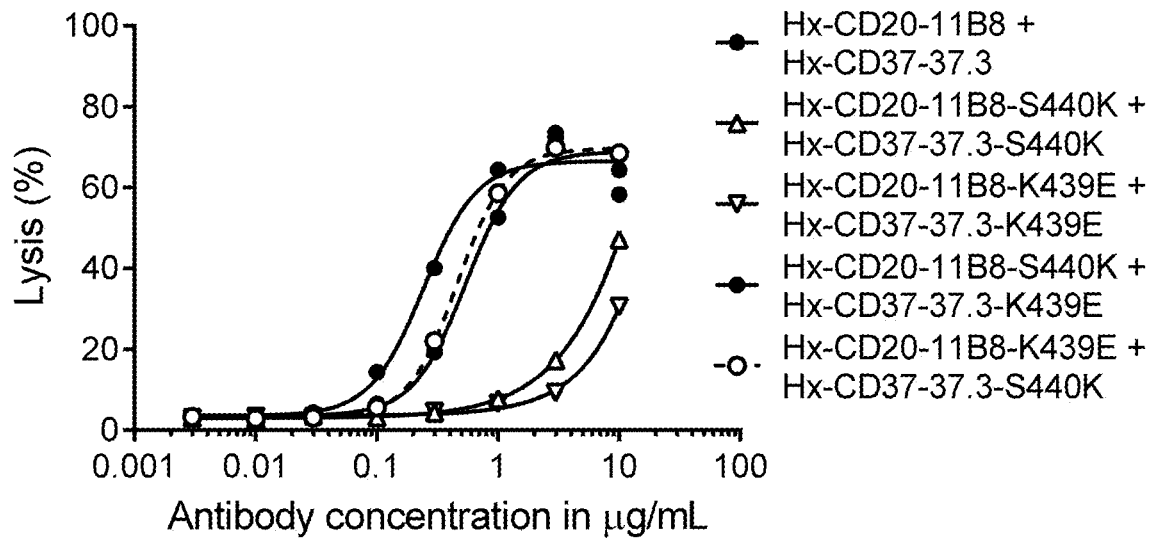
Figure 5F:
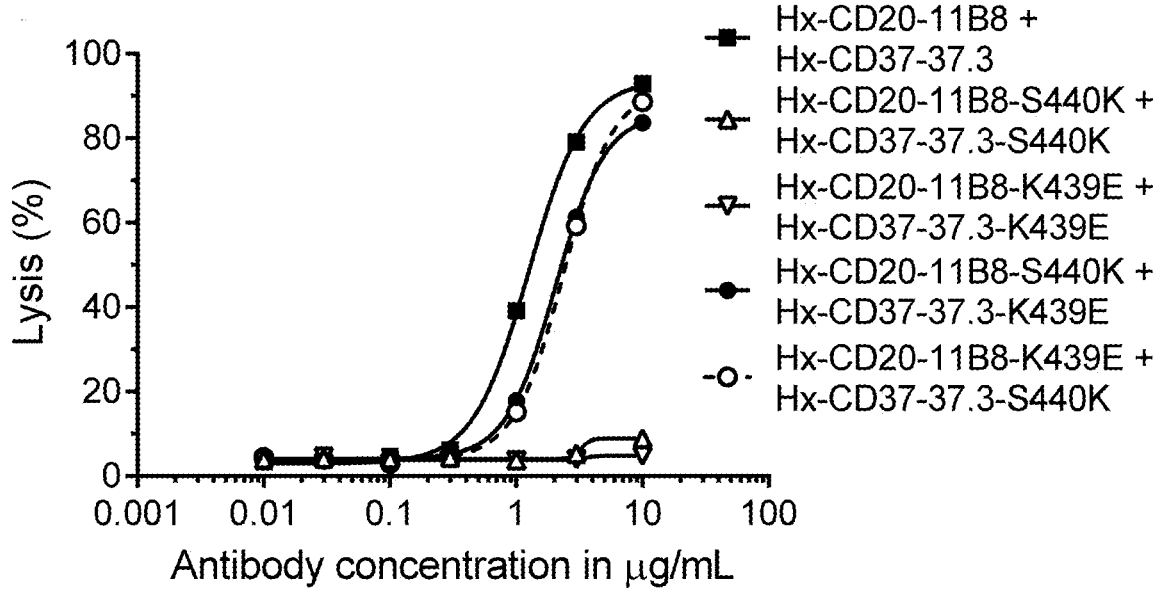

The CDC activity of hexamerization-enhanced CD20 antibody IgG1-CD20-11B8-E430G (Hx-CD20-11B8) was completely inhibited by introduction of either the K439E or S440K Fc-Fc inhibiting mutation, both on Daudi (FIG. 5A) and WIL2-S cells (FIG. 5B). As expected, CDC activity was restored when Fc-Fc inhibition was neutralized by combining the two anti-CD20 antibodies, each having one of the complementary mutations K439E or S440K. Similar results were found for the hexamerization-enhanced CD37 antibody IgG1-CD37-37.3-E430G (Hx-CD37-37.3) on Daudi cells (FIG. 5C). On WIL2-S cells (FIG. 5D), which have low CD37 expression (data not shown), none of the tested Hx-CD37-37.3 variants induced CDC. Combinations of Hx-CD20-11B8 and Hx-CD37-37.3 harboring both the same Fc-Fc interaction inhibiting mutation (K439E or S440K) showed strongly reduced CDC activity on Daudi cells (FIG. 5E) compared to the combination of Hx-CD20-11B8 and Hx-CD37-37.2 without the K439E or S440K mutations. In WIL2-S cells, introduction of either the K439E or S440K mutation in both hexamerization-enhanced CD20 and CD37 antibodies, completely abolished CDC activity (FIG. 5F). Combining Hx-CD20-11B8 and Hx-CD37-37.3 variants that each carried one of the complementary mutations K439E or S440K resulted in restored CDC activity in Daudi (FIG. 5E) and also in WIL2-S cells (FIG. 5F).

These data illustrate that hexamerization-enhanced CD20 antibody IgG1-CD20-11B8-E430G (Hx-CD20-11B) and hexamerization-enhanced CD37 antibody IgG1-CD37-37.3-E430G (Hx-CD37-37.3) can engage in intermolecular Fc-Fc interactions upon binding their cognate antigens CD20 and CD37, and form hetero-hexameric antibody complexes on the cell surface.

Example 7

Evaluating Antibody Hetero-Hexamer Formation between Hexamerization-Enhanced CD37 and CD20 Antibodies on the Cell Surface using FRET Analysis Example 6 described that by combining and neutralizing the K439E and S440K Fc-Fc interaction inhibiting mutations in hexamerization-enhanced CD20 antibody IgG1-CD20-11B8-E430G (Hx-CD20-11B8) and hexamerization-enhanced CD37 antibody IgG1-CD37-37.3-E430G (Hx-CD37-37.3), each containing either mutation K439E or S440K, the mixture of the two antibodies was able to induce CDC, whereas CDC by the single antibody variants was inhibited. These data indicated that in the antibody mixture, the antibodies were able to establish intermolecular Fc-Fc interactions and co-assemble into hetero-hexamers. To examine this further, the molecular proximity between the membrane-bound, hexamerization-enhanced CD20 and CD37 antibodies, with and without the K439E and S440K mutations, was analyzed by FRET analysis. FRET analysis was performed using Daudi cells with A555 (donor) and A647 (acceptor) conjugated antibodies as described in Example 5.

Figure 6:
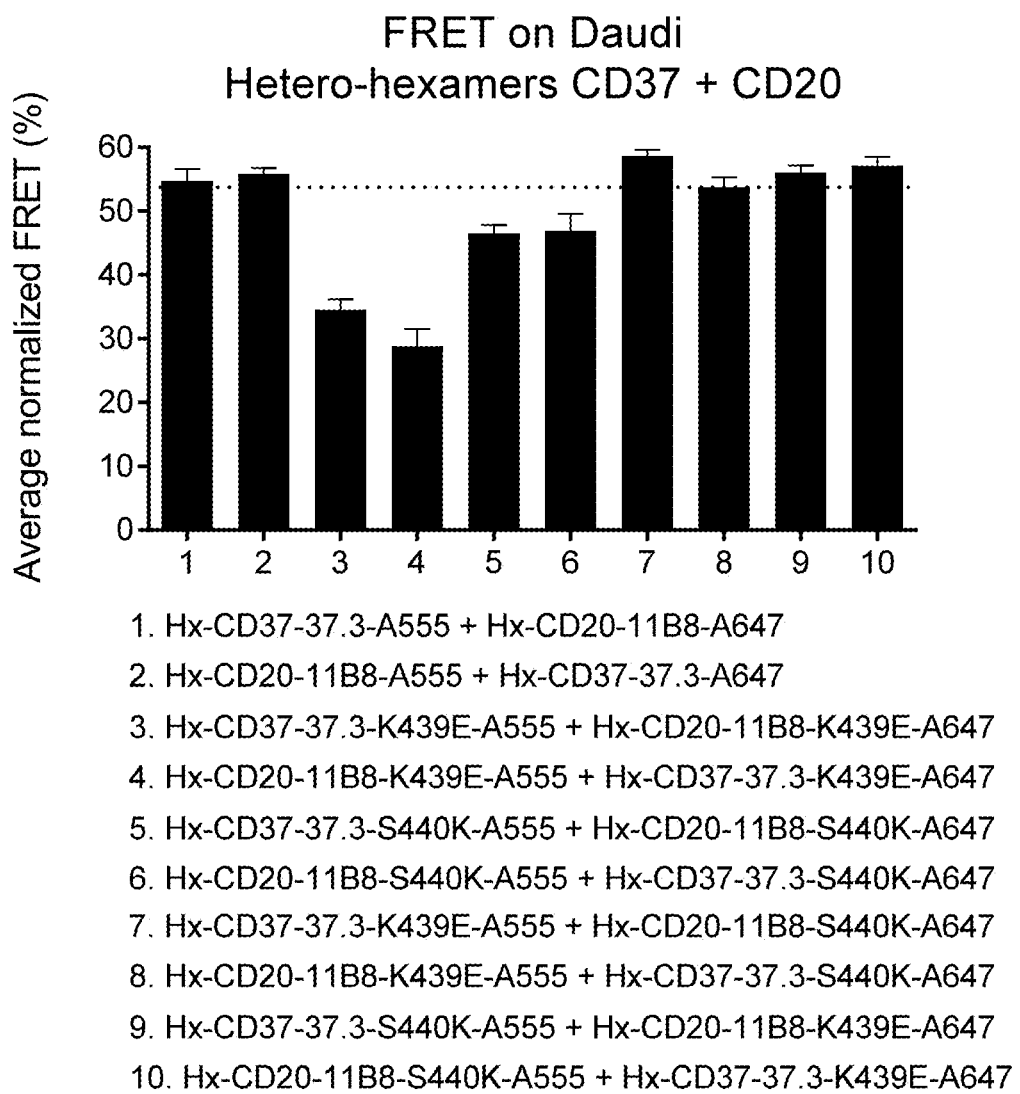
FIG. 6 shows FRET analysis for the hetero-hexameric antibody complexes formed by A555- or A647-conjugated hexamerization-enhanced IgG1-CD20-11B8-E430G (Hx-CD20-11B8) and IgG1-CD37-37.3-E430G (Hx-CD37-37.3) on the cell membrane of Daudi cells. Hetero-hexamer formation was controlled by introduction of the complementary mutations K439E and S440K. FRET was calculated from the mean fluorescence intensity (MFI) as determined by flow cytometry. Data shown are mean and standard deviation (SD) of six replicates collected from three experiments.

FRET efficiency by the antibody mixture Hx-CD20-11B8 and Hx-CD37-37.3 bound to Daudi cells was decreased by introduction of an Fc-Fc interaction inhibiting mutation (K439E or S440K) in both antibodies (FIG. 6). When Fc-Fc inhibition was neutralized by mixing Hx-CD20-11B8 and Hx-CD37-37.3 variants, each having one of the complementary mutations K439E or S440K, FRET levels were restored to the levels observed for the mixtures of the hexamerization-enhanced antibodies without an Fc-Fc inhibiting mutation. These data indicated that in the hetero-hexameric antibody complexes on the cell membrane of Daudi cells, the hexamerization-enhanced antibodies Hx-CD20-11B8 and Hx-CD37-37.3 were in close proximity of each other (<10 nm). The close proximity was reduced by introducing mutations that inhibit Fc-Fc interactions, indicating that close proximity between Hx-CD20-11B8 and Hx-CD37-37.3 was facilitated by intermolecular Fc-Fc interactions.

Example 8

Ex Vivo Evaluation of CDC Activity of Mixtures of Hexamerization-Enhanced CD37 and CD20 Antibodies in Various Non-Hodgkin Lymphoma Patient-Derived Primary Tumor Cells The CDC activity of the mixture of the hexamerization-enhanced CD37 antibody IgG1-CD37-37.3-E430G (Hx-CD37-37.3) with hexamerization-enhanced CD20 antibody IgG1-CD20-11B8-E430G (Hx-CD20-11B8) was analyzed on primary patient-derived tumor cells from four different Non-Hodgkin lymphoma (NHL) indications: B cell NHL (B-NHL), Follicular Lymphoma (FL), Mantle-Cell Lymphoma (MCL) and Marginal Zone Lymphoma (MZL). All patient samples were obtained after written informed consent and stored using protocols approved by the VUmc Medical Ethical Committee in accordance with the declaration of Helsinki. Patient bone marrow mononuclear cells (BMNCs) or peripheral blood mononuclear cells (PBMCs) were isolated by density-gradient centrifugation (Ficoll-Paque PLUS, GE Healthcare) from bone marrow aspirates or peripheral blood samples of lymphoma patients. Cells were either used directly or stored in liquid nitrogen until further use.

Patient lymph nodes were dissected into small fragments and collected in a-MEM medium (ThermoFischer Scientific) containing 1% Penicillin-Streptomycin, 0.2% heparin and 5% platelet lysate and left overnight at 37° C. After incubation, the supernatant (non-stromal cell compartment) was removed and cells were filtered using a 70 µM Easy Strainer (Greiner Bio-one). Cells were counted, resuspended in RPMI 1640 medium containing 25% heat-inactivated FBS and 10% DMSO, and frozen in liquid nitrogen until further use.

Figure 7A:
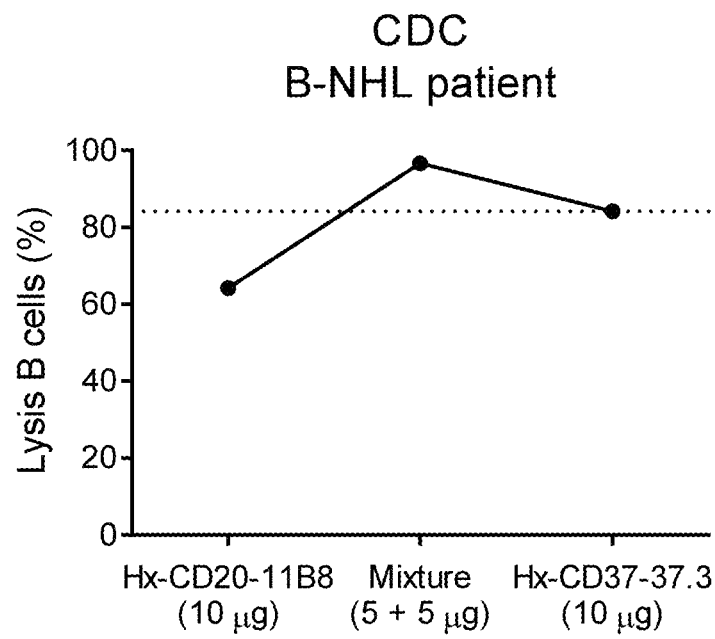
FIGS. 7A-7D show CDC activity of the mixture of hexamerization-enhanced IgG1-CD37-37.3 (Hx-CD37-37.3) and hexamerization-enhanced IgG1-CD20-11B8-E430G (Hx-CD20-11B8) on primary tumor B cells derived from patients with a Non-Hodgkin Lymphoma (NHL) indication.
Figure 7B:
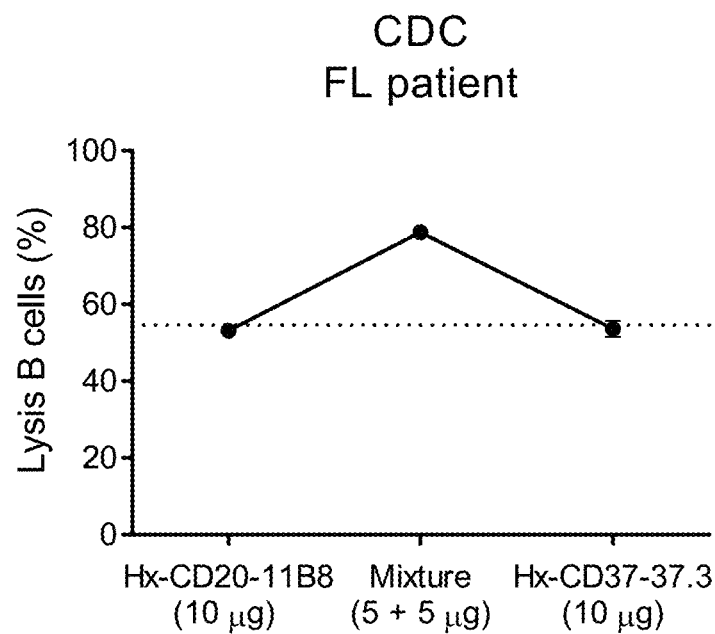
Figure 7C:
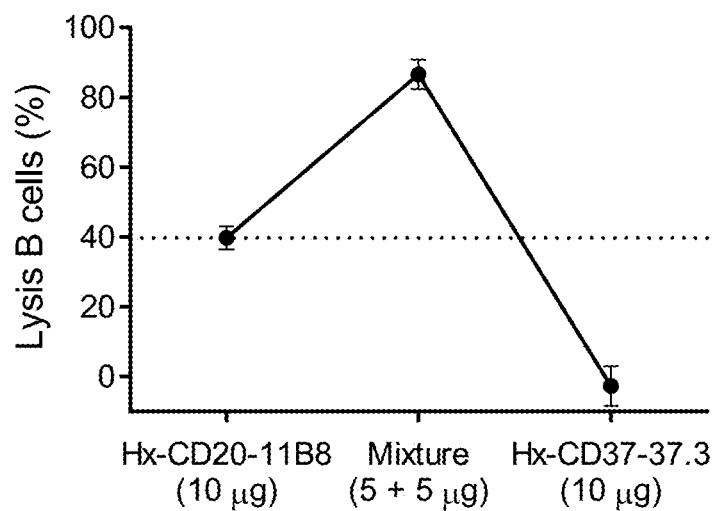
Figure 7D:
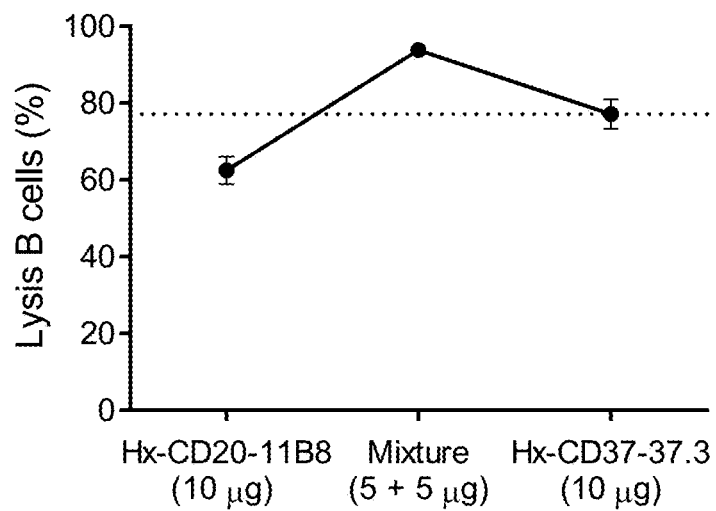
Figure 8A:
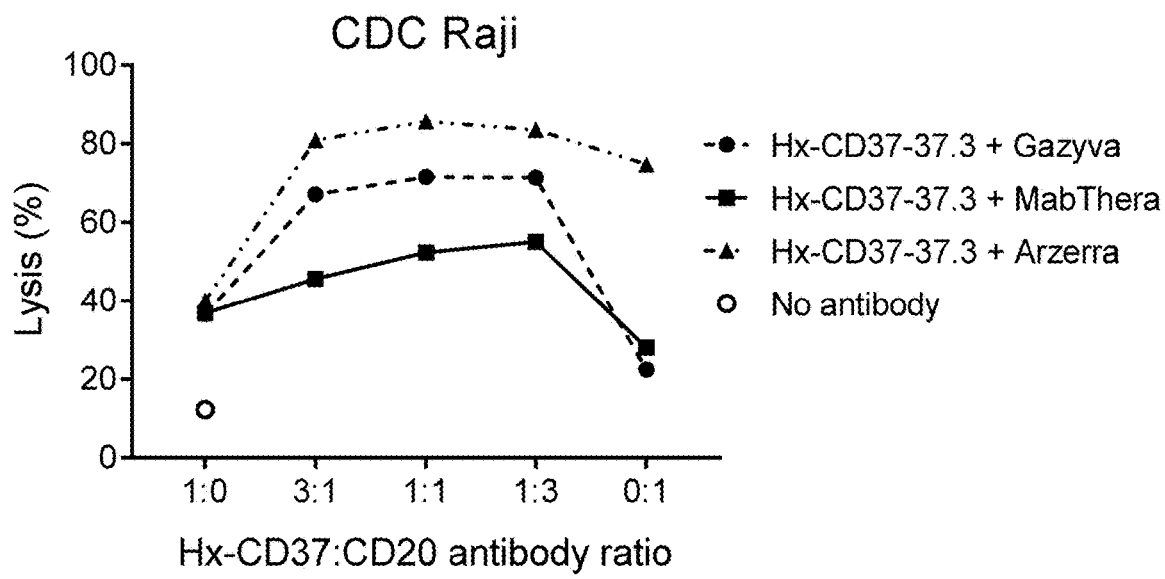
FIGS. 8A-8F show the in vitro CDC-mediated killing of Raji cells (% lysis expressed as the PI-positive cell fraction as determined by flow cytometry) for antibody concentration dilution series of 1:0, 3:1, 1:1, 3:1 and 0:1 antibody mixtures (10 µg/mL final concentration) of hexamerization-enhanced CD37 antibodies with standard of care (SOC) CD20 antibody products MabThera (rituximab), Arzerra (ofatumumab) and Gazyva (obinutuzumab, GA101)
Figure 8B:
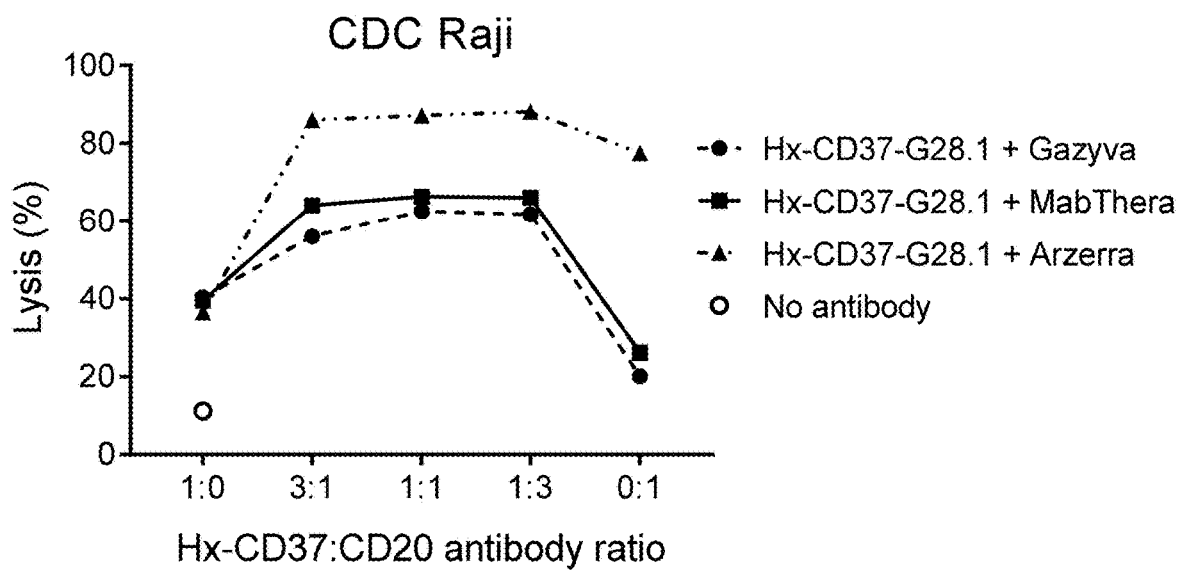
Figure 8C:
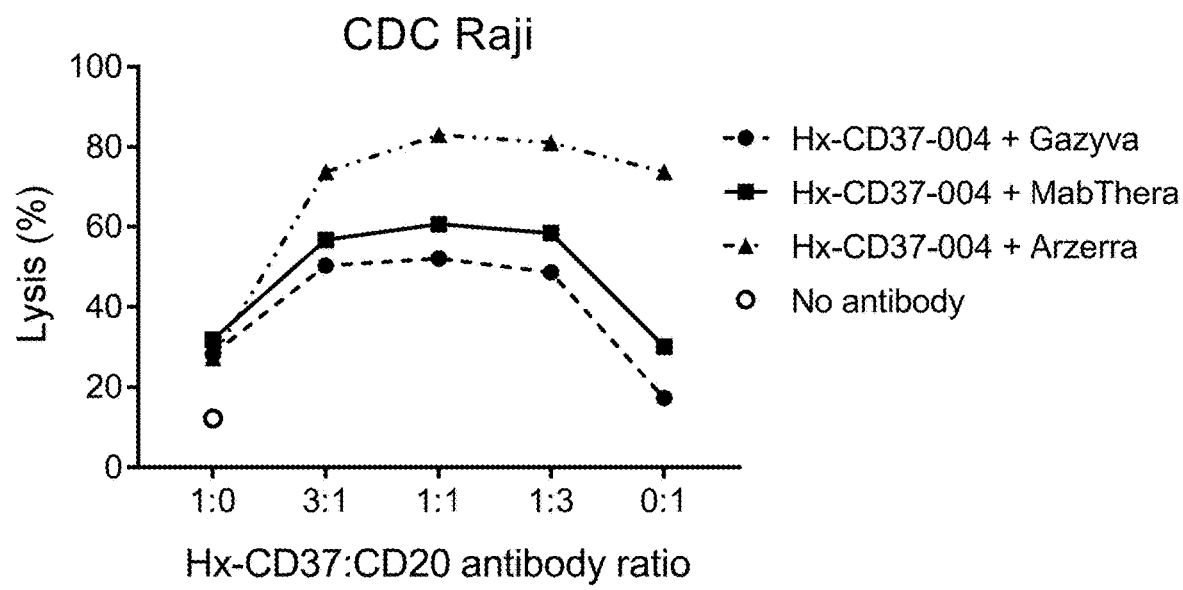
Figure 8D:
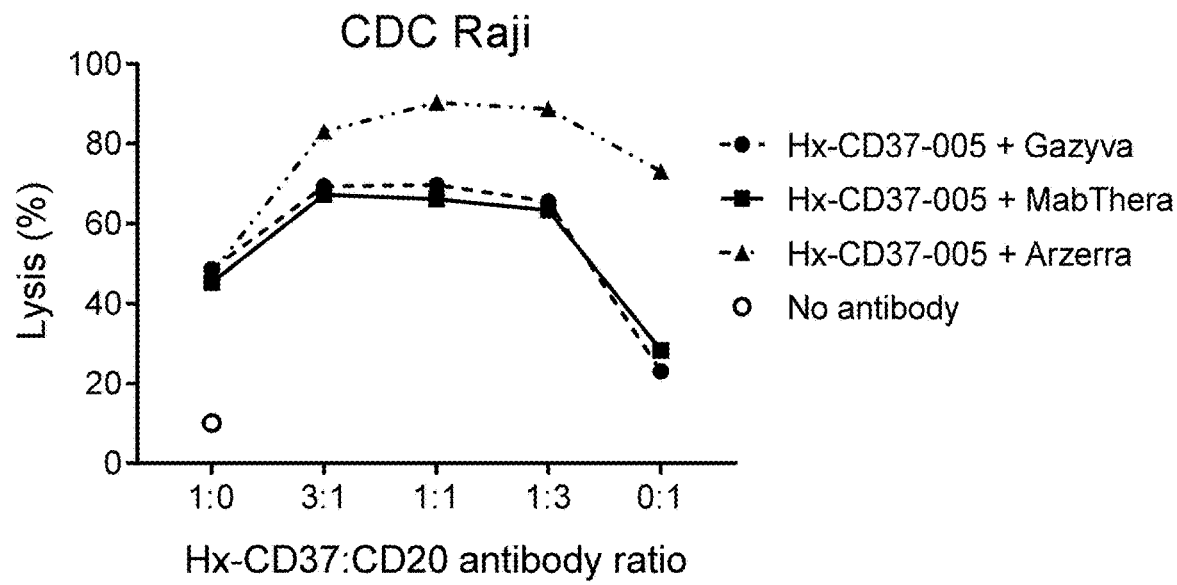
Figure 8E:
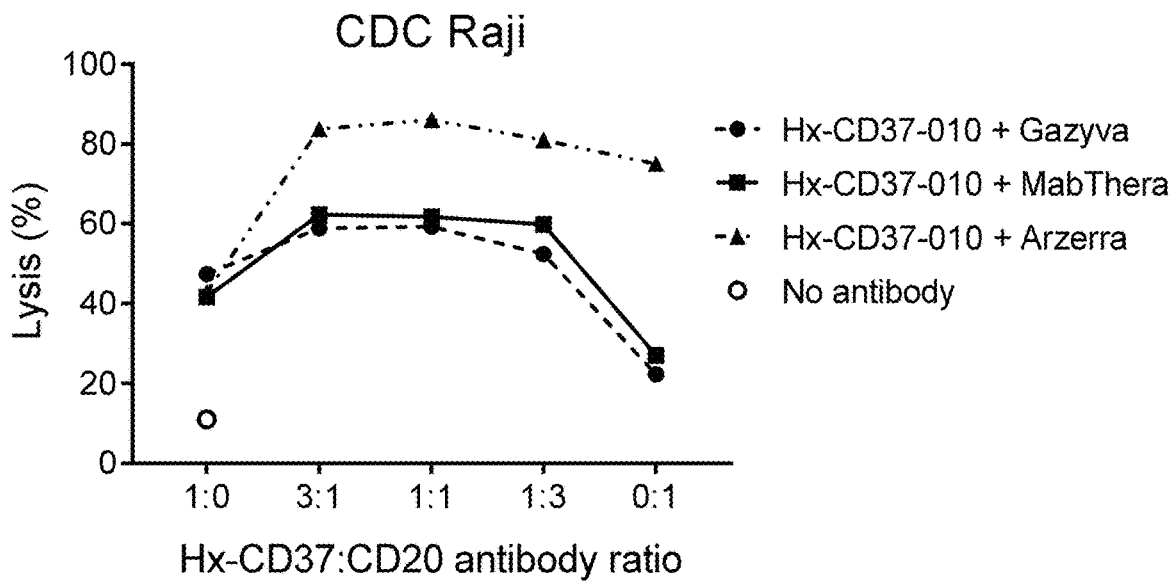
Figure 8F:
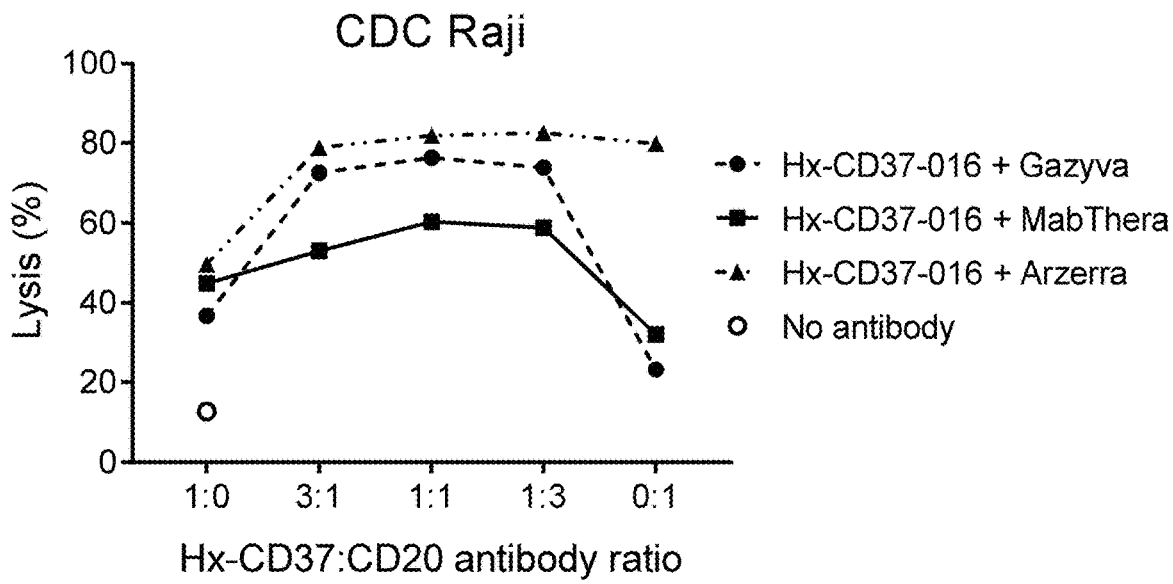

The patient-derived tumor cells were opsonized with 10 µg/mL Hx-CD20-11B8, Hx-CD37-37.3 or the mixture thereof (5+5 µg/mL) and CDC activity was assessed in the presence of 20% pooled NHS. The following cell markers were used to define different cell populations: CD45-KO (Beckman Coulter), CD19-PC7 (Beckman Coulter), CD3-V450 (BD), CD5-APC (BD), CD5-PE (DAKO), CD10-APC-H7 (BD), CD10-PE (DAKO) and CD23-FITC (Biolegend). Within the CD45+ cell population, B-lymphoma cells were defined by different markers depending on the lymphoma indication: CD3−/CD19+/CD5+ (CLL), CD3−/CD19+/CD10+ (FL, DLBCL), CD3−/CD19+/CD5+/CD23+ (MCL). Clonality of the malignant cells was detected using kappa/lambda staining. Dead cells were visualized by flow cytometry after incorporation of 7-amino actinomycin D (7-AAD), which is a membrane impermeable double-stranded DNA-intercalating fluorochrome. In all four tested samples, enhanced CDC activity was observed with the mixture of Hx-CD20-11B8 and Hx-CD37-37.3 compared to the single antibodies (FIG. 7), even when one of the antibodies did not induce any CDC by itself (FIG. 7C), consistently demonstrating synergy between the hexamerization-enhanced CD20 and CD37 antibodies.

Example 9

In Vitro Evaluation of CDC Activity of Mixtures of Novel Hexamerization-Enhanced CD37 Antibodies with Clinically Established CD20 Antibody Products on Raji Cells The CDC activity of mixtures the hexamerization-enhanced CD37 antibodies IgG1-CD37-37.3-E430G (Hx-CD37-37.3), IgG1-CD37-G28.1-E430G (Hx-CD37-G28.1) or novel chimeric rabbit/human IgG1-CD37 antibodies IgG1-CD37-004-E430G (Hx-CD37-004), IgG1-CD37-005-E430G (Hx-CD37-005), IgG1-CD37-010-E430G (Hx-CD37-010) and IgG1-CD37-016-E430G (Hx-CD37-016), with the clinically established CD20-targeting monoclonal antibody products MabThera (rituximab; Roche, H0124B08), Arzerra (ofatumumab; Novartis; C656294) and Gazyva (obinutuzumab, GA101; Roche, D287-41A GACD20) was tested in vitro using Burkitt's lymphoma Raji cells. Raji cells (ATCC, Cat No. CCL-86) were cultured in RPMI 1640 supplemented with 10% heat-inactivated FBS, 1 U/mL penicillin, 1 µg/mL streptomycin, and 4 mM L-glutamine. $0.1 \times 10^6$ Raji cells were pre-incubated with antibodies in a total volume of 80 µL RPMI/0.2% BSA per well for 15 min on a shaker at RT. Next, NHS was added to the pre-incubated cells to a final volume of 100 µL (final antibody concentrations 10 µg/mL; 20% NHS) and incubated for 45 minutes at 37° C. For all tested total antibody concentrations, different ratios of the two antibodies in the mixtures were tested (1:0-3:1-1:1-1:3-0:1). Plates were centrifuged and cells were resuspended in 30 µL PI (2 µg/mL). Killing was calculated as the fraction PI-positive cells (%) determined by flow cytometry on an iQue screener (Intellicyt). Data were analyzed and plotted using GraphPad Prism software.

The mixtures of the tested hexamerization-enhanced CD37 antibodies and clinically established CD20 antibody products showed enhanced dose-dependent CDC activity compared to the same concentration of the single antibodies on Raji cells (FIG. 8). There was little difference in CDC activity at the different tested ratios of the two antibodies in the mixtures (1:3, 1:1 or 3:1). These data illustrate that the mixture of a hexamerization-enhanced CD37 antibody with a clinically established CD20 antibody product, such as MabThera, Arzerra (type I CD20 antibodies) or Gazyva (type II CD20 antibody), may improve the therapeutic potential for patients with B cell malignancies, which frequently become refractory to standard CD20 targeted therapies alone.

The invention claimed is:

1. A composition comprising (a) a first antibody and a second antibody, wherein the first antibody comprises a first antigen-binding region capable of binding to human CD37 and a first Fc region of a human IgG, and the second antibody comprises a second antigen-binding region capable of binding to human CD20 and a second Fc region of a human IgG, wherein both the first Fc region and the second Fc region comprise a substitution of an amino acid at a position corresponding to E430, E345 or S440 in human IgG1 when using the EU numbering system, with the proviso that the substitution in S440, if present, is S440Y or S440W, and (b) a carrier,
  wherein the first antigen-binding region comprises a variable heavy chain (VH) region comprising CDR sequences HCDR1, HCDR2 and HCDR3 and a variable light chain (VL) region comprising CDR sequences LCDR1, LCDR2 and LCDR3 selected from the group consisting of:
  a. SEQ ID NOs: 22, 23, and 24, respectively, and SEQ ID NO: 26, the sequence EAS, and SEQ ID NO: 27, respectively,
  b. SEQ ID NOs: 29, 30, and 31, respectively, and SEQ ID NO: 33, the sequence AAS, and SEQ ID NO: 34, respectively,
  c. SEQ ID NOs: 36, 37, and 38, respectively, and SEQ ID NO: 40, the sequence KAS, and SEQ ID NO: 41, respectively,
  d. SEQ ID NOs: 43, 44, and 45, respectively, and SEQ ID NO: 47, the sequence YAS, and SEQ ID NO: 48, respectively,
  e. SEQ ID NOs: 43, 44, and 45, respectively, and SEQ ID NO: 47, the sequence YAS, and SEQ ID NO: 58, respectively,
  f. SEQ ID NOs: 8, 9, and 10, respectively, and SEQ ID NO: 12, the sequence VAT, and SEQ ID NO: 13, respectively, and
  g. SEQ ID NOs: 15, 16, and 17, respectively, and SEQ ID NO: 19, the sequence FAK, and SEQ ID NO: 20, respectively.

2. The composition according to claim 1, wherein the first Fc region and the second Fc region comprise a substitution selected from the group consisting of: E430G, E345K, E430S, E430F, E430T, E345Q, E345R, E345Y, S440Y and S440W.

3. The composition according to claim 1, wherein the first Fc region further comprises a K439E substitution and the second Fc region further comprises an S440K substitution, with the proviso that the second Fc region does not comprise a S440Y or S440W substitution.

4. The composition according to claim 1, wherein the first Fc region further comprises a S440K substitution and the second Fc region further comprises an K439E substitution, with the proviso that the first Fc region does not comprise a S440Y or S440W substitution.

5. The composition according to claim 1, wherein the first antigen-binding region comprises VH and VL region sequences selected from the group consisting of:
  a. SEQ ID NO: 49 and SEQ ID NO: 50, respectively,
  b. SEQ ID NO: 51 and SEQ ID NO: 52, respectively,
  c. SEQ ID NO: 53 and SEQ ID NO: 54, respectively,
  d. SEQ ID NO: 55 and SEQ ID NO: 56, respectively,
  e. SEQ ID NO: 55 and SEQ ID NO: 57, respectively,
  f. SEQ ID NO: 7 and SEQ ID NO: 11, respectively, and
  g. SEQ ID NO: 14 and SEQ ID NO: 18, respectively.

6. The composition according to claim 1, wherein the second antigen-binding region comprises a VH region comprising CDR sequences HCDR1, HCDR2 and HCDR3, and a VL region comprising CDR sequences LCDR1, LCDR2 and LCDR3, selected from the group consisting of:
- a. SEQ ID NOs: 60, 61, and 62, respectively, and SEQ ID NO: 64, the sequence DAS, and SEQ ID NO: 65, respectively,
- b. SEQ ID NOs: 67, 68, and 69, respectively, and SEQ ID NO: 64, the sequence DAS, and SEQ ID NO: 71, respectively,
- c. SEQ ID NOs: 73, 74, and 62, respectively, and SEQ ID NO: 64, the sequence DAS, and SEQ ID NO: 65, respectively,
- d. SEQ ID NOs: 76, 77, and 78, respectively, and SEQ ID NO: 80, the sequence ATS, and SEQ ID NO: 81, respectively, and
- e. SEQ ID NOs: 83, 84, and 85, respectively, and SEQ ID NO: 87, the sequence QMS, and SEQ ID NO: 88, respectively.

7. The composition according to claim 1, wherein the second antigen-binding region comprises VH and VL region sequences selected from the group consisting of:
- a. SEQ ID NO: 59 and SEQ ID NO: 63, respectively,
- b. SEQ ID NO: 66 and SEQ ID NO: 70, respectively,
- c. SEQ ID NO: 72 and SEQ ID NO: 63 respectively,
- d. SEQ ID NO: 75 and SEQ ID NO: 79, respectively, and
- e. SEQ ID NO: 82 and SEQ ID NO: 86, respectively.

8. The composition according to claim 1, wherein the first antigen binding region comprises a variable heavy chain (VH) VH region comprising the CDR sequences HCDR1, HCDR2 and HCDR3 and a variable light chain (VL) VL region comprising the CDR sequences LCDR1, LCDR2 and LCDR3 selected from the group consisting of:
- a. SEQ ID NOs: 22, 23, and 24, respectively, and SEQ ID NO: 26, the sequence EAS, and SEQ ID NO: 27, respectively,
- b. SEQ ID NOs: 29, 30, and 31, respectively, and SEQ ID NO: 33, the sequence AAS, and SEQ ID NO: 34 respectively,
- c. SEQ ID NOs: 36, 37, and 38, respectively, and SEQ ID NO: 40, the sequence KAS, and SEQ ID NO: 41, respectively,
- d. SEQ ID NOs: 43, 44, and 45, respectively, and SEQ ID NO: 47, the sequence YAS, and SEQ ID NO: 48 respectively,
- e. SEQ ID NOs: 43, 44, and 45, respectively, and SEQ ID NO: 47, the sequence YAS, and SEQ ID NO: 58 respectively,
- f. SEQ ID NOs: 8, 9, and 10, respectively, and SEQ ID NO: 12, the sequence VAT, and SEQ ID NO: 13 respectively, and
- g. SEQ ID NOs: 15, 16, and 17, respectively, and SEQ ID NO: 19, the sequence FAK, and SEQ ID NO: 20, respectively, and the second antigen-binding region comprises a VH region comprising the CDR sequences HCDR1, HCDR2 and HCDR3 and a VL region comprising the CDR sequences LCDR1, LCDR2 and LCDR3 selected from the group consisting of:
- h. SEQ ID NOs: 60, 61, and 62, respectively, and SEQ ID NO: 64, the sequence DAS, and SEQ ID NO: 65, respectively,
- i. SEQ ID NOs: 67, 68, and 69, respectively, and SEQ ID NO: 64, the sequence DAS, and SEQ ID NO: 71, respectively,
- j. SEQ ID NOs: 73, 74, and 62, respectively, and SEQ ID NO: 64, the sequence DAS, and SEQ ID NO: 65, respectively,
- k. SEQ ID NOs: 76, 77, and 78, respectively, and SEQ ID NO: 80, the sequence ATS, and SEQ ID NO: 81, respectively, and
- l. SEQ ID NOs: 83, 84, and 85, respectively, and SEQ ID NO: 87, the sequence QMS, and SEQ ID NO: 88 respectively.

9. The composition according to claim 1, wherein the first antigen binding region comprises the variable heavy chain (VI) VH and variable light chain (VL) VL region sequences selected from the group consisting of:
- a. SEQ ID NO: 49 and SEQ ID NO: 50, respectively,
- b. SEQ ID NO: 51 and SEQ ID NO: 52, respectively,
- c. SEQ ID NO: 53 and SEQ ID NO: 54, respectively,
- d. SEQ ID NO: 55 and SEQ ID NO: 56, respectively,
- e. SEQ ID NO: 55 and SEQ ID NO: 57, respectively,
- f. SEQ ID NO: 7 and SEQ ID NO: 11, respectively, and
- g. SEQ ID NO: 14 and EQ SEQ ID NO: 18, respectively, and the second antigen-binding region comprises the VH and VL region sequences selected from the group consisting of:
- h. SEQ ID NO: 59 and SEQ ID NO: 63, respectively,
- i. SEQ ID NO: 66 and SEQ ID NO: 70, respectively,
- j. SEQ ID NO: 72 and SEQ ID NO: 63, respectively,
- k. SEQ ID NO: 75 and SEQ ID NO: 79, respectively, and
- l. SEQ ID NO: 82 and SEQ ID NO: 86, respectively.

10. The composition according to claim 1, wherein the first and/or second antibody is human, humanized or chimeric.

11. The composition according to claim 1, wherein the first antibody is humanized and the second antibody is human.

12. The composition according to claim 1, wherein the first and/or second antibody is a monoclonal antibody.

13. The composition according to claim 1, wherein the first and/or second antibody is a human IgG1, IgG2, IgG3 or IgG4 isotype.

14. The composition according to claim 1, wherein the first and/or second antibody is an IgG1m (f), IgG1m (a), IgG1m (z), IgG1m (x) allotype or mixed allotype.

15. A method of inducing cell death, or inhibiting growth and/or proliferation of a tumor cell expressing CD37 and CD20, comprising administering to an individual in need thereof the composition according to claim 1.

16. The method according to claim 15, comprising administering a further therapeutic agent.

17. The method according to claim 16, wherein the further therapeutic agent is selected from the group consisting of: doxorubicin, cisplatin, bleomycin, carmustine, cyclophosphamide, chlorambucil, bendamustine, vincristine, fludarabine, ibrutinib and venetoclax.

18. A method of treating an individual having a solid tumor and/or hematological tumor, comprising administering to said individual an effective amount of the composition according to claim 1.

* * * * *